United States Patent
Olek

(10) Patent No.: US 10,273,545 B2
(45) Date of Patent: Apr. 30, 2019

(54) EPIGENETIC METHOD FOR THE IDENTIFICATION OF SUBPOPULATIONS OF CD8+ T LYMPHOCYTES, IN PARTICULAR CD8 ALPHA AND BETA T LYMPHOCYTES

(71) Applicant: EPIONTIS GMBH, Berlin (DE)

(72) Inventor: Sven Olek, Berlin (DE)

(73) Assignee: Epiontis GmbH, Berlin (DE)

( * ) Notice: Subject to any disclaimer, the term of this patent is extended or adjusted under 35 U.S.C. 154(b) by 0 days.

(21) Appl. No.: 14/443,223

(22) PCT Filed: Nov. 25, 2013

(86) PCT No.: PCT/EP2013/074642
§ 371 (c)(1),
(2) Date: May 15, 2015

(87) PCT Pub. No.: WO2014/080017
PCT Pub. Date: May 30, 2014

(65) Prior Publication Data
US 2015/0307946 A1 Oct. 29, 2015

(30) Foreign Application Priority Data
Nov. 23, 2012 (GB) .................................. 1221133.0

(51) Int. Cl.
*C12Q 1/68* (2018.01)
*C12Q 1/6886* (2018.01)
*C12Q 1/6881* (2018.01)

(52) U.S. Cl.
CPC ......... *C12Q 1/6886* (2013.01); *C12Q 1/6881* (2013.01); *C12Q 2600/154* (2013.01)

(58) Field of Classification Search
None
See application file for complete search history.

(56) References Cited

U.S. PATENT DOCUMENTS

| 2010/0047778 A1* | 2/2010 | Koehler | ............... C12Q 1/6858 435/6.12 |
| 2012/0107810 A1 | 5/2012 | Olek et al. | |
| 2013/0260378 A1* | 10/2013 | Olek | ..................... C12Q 1/6886 435/6.11 |

FOREIGN PATENT DOCUMENTS

| EP | 2 141 245 A1 | 1/2010 |
| EP | 2 199 411 A1 | 6/2010 |
| EP | 2 248 913 A1 | 11/2010 |
| WO | WO-2010-069499 A2 * | 6/2010 |
| WO | WO 2012/045888 A1 | 4/2012 |
| WO | WO 2012/158556 A1 | 11/2012 |

OTHER PUBLICATIONS

Ushijima et al. Nature Reviews. 2005. 5: 223-231.*
Bilic et al Nature Immunology. 2006. 7:392.*
Ehrlich et al. Oncogene 2002. 21: 5400-5413.*
Campbell, John P. et al., "Total lymphocyte CD8 expression is not a reliable marker of cytotoxic T-cell populations in human peripheral blood following an acute bout of high-intensity exercise," *Brain, Behavior, and Immunity*, 2008, 22:375-380.
Chetty, Runjan et al., "CD3: Structure, Function, and Role of Immunostaining in Clinical Practice," *Journal of Pathology*, 1994, 173:303-307.
Correa, Paula A. et al., "Bisulfite genomic sequencing to uncover variability in DNA methylation: Optimized protocol applied to human T cell differentiation genes," *Inmunologia*, 2012, 31(4):97-105.
Hamerman, Jessica A. et al., "Distinct Methylation States of the CD8β Gene in Peripheral T Cells and Intraepithelial Lymphocytes[1]," *The Journal of Immunology*, 1997, 159:1240-1246.
Hassan, Hammad et al., "Cd8 enhancer E8$_I$ and Runx factors regulate CD8α expression in activated CD8+ T cells," *PNAS*, 2011, 108(45):18330-18335.
Kioussis, Dimitris et al., "Chromatin and CD4, CD8A and CD8B Gene Expression During Thymic Differentiation," *Nature Reviews: Immunology*, 2002, 2:909-919.
Sehouli, Jalid et al., "Epigenetic quantification of tumor-infiltrating T-lymphocytes," *Epigenetics*, 2011, 6(2):236-246.
Wadsworth, Scott et al., "Origin and selection of peripheral CD4$^-$CD8$^-$ T cells bearing α/β T cell antigen receptors in autoimmune gld mice*," *Eur. J. Immunol.*, 1990, 20:723-730.
Watanabe, Nobukazu et al., "Long-Term Depletion of Naïve T Cells in Patients Treated for Hodgkin's Disease," *Blood*, 1997, 90:3662-3672.
Werwitzke, S. et al., "CD8α+β$^{low}$ Effector T Cells in Systemic Lupus Erythematosus," *Scandinavian Journal of Immunology*, 2008, 67:501-508.

* cited by examiner

*Primary Examiner* — Carla J Myers
(74) *Attorney, Agent, or Firm* — Baker & Hostetler LLP

(57) ABSTRACT

The present invention relates to a method, in particular an in vitro method, for identifying CD8 positive subpopulations of a mammal, wherein said method comprises analyzing the bisulfite convertibility of at least one CpG position in the CD8 beta and CD8 alpha cell specific bisulfite convertibility gene region according to SEQ ID No. 1 and 2, wherein a bisulfite convertibility of at least one CpG position in said gene regions is indicative for a CD3+CD8+ and/or CD3+/−CD8+ cell. The analyzes according to the invention can identify CD3+CD8+ and/or CD3+/−CD8+ cells on an epigenetic level and distinguish them from all other cells in complex samples, such as, for example, other blood cells.

20 Claims, 4 Drawing Sheets
Specification includes a Sequence Listing.

EPIGENETIC METHOD FOR THE IDENTIFICATION OF SUBPOPULATIONS OF CD8+ T LYMPHOCYTES, IN PARTICULAR CD8 ALPHA AND BETA T LYMPHOCYTES

CROSS REFERENCE TO A RELATED APPLICATION

This application is a National Stage Application of International Application Number PCT/EP2013/074642, filed Nov. 25, 2013; which claims priority to Great Britain Application No. 1221133.0, filed Nov. 23, 2012; both of which are incorporated herein by reference in their entirety.

The Sequence Listing for this application is labeled "SeqList-15May15.txt", which was created on May 15, 2015, and is 116 KB. The entire content is incorporated herein by reference in its entirety.

The present invention relates to a method, in particular an in vitro method, for identifying CD8 positive subpopulations of a mammal, wherein said method comprises analyzing the bisulfite convertibility of at least one CpG position in the CD8 beta and CD8 alpha cell specific bisulfite convertibility gene region according to SEQ ID No. 1 and 2, wherein a bisulfite convertibility of at least one CpG position in said gene regions is indicative for a CD3+CD8+ and/or CD3+/−CD8+ cell. The analyses according to the invention can identify CD3+CD8+ and/or CD3+/−CD8+ cells on an epigenetic level and distinguish them from all other cells in complex samples, such as, for example, other blood cells. The present invention furthermore provides an improved method for quantifying CD3+CD8+ and/or CD3+/−CD8+ cells in complex samples, in particular based on a comparison of the CD8 beta and alpha gene bisulfite convertibility with a bisulfite convertibility of at least one marker selected from the group of CD3, CD4, FOXP3, NKT, NK, T helper cells and/or GAPDH. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure particular subsets of CD8+ cells of the blood within any solid organs or tissue or any body fluid of a mammal. Employing this method, the inventors provide novel, not previously known means for determining, quantifying and routinely measuring CD8 alpha/beta and CD8 alpha/alpha cells.

BACKGROUND OF THE INVENTION

CD8 (cluster of differentiation 8) is a transmembrane glycoprotein expressed on the surface of cytotoxic T-cells, but also of natural killer cells, cortical thymocytes and dendritic cells. CD8 forms a homo- or heterodimer comprised of either CD8 alpha and/or CD8 beta chains. CD8 interacts with class I MHC receptors during antigen-specific activation, functions as a co-receptor which associates with protein tyrosine kinase p56lck, and participates in T-cell receptor-mediated activation. According to current research, homodimers only exist as alpha/alpha chains and are expressed by CD3+/−CD8+ cells (cytotoxic T cells, NKT cells), whereas the heterodimer alpha/beta is expressed by CD3+CD8+ cells only. In humans, the CD8 alpha and beta molecules are encoded by CD8 alpha gene and CD8 beta gene.

T-lymphocytes are a major component of the mammalian immune system. Cytotoxic CD3+CD8+ T-cells are an important part of the cell-mediated immunity and hence mediating the cytotoxic immune defense. CD8+ cytotoxic T-cells lyse cells displaying epitopes of foreign antigens on their surface in order to kill infected, cancerous or damaged cells to prevent cancer, autoimmunity or infection. Natural killer cells, cortical thymocytes, and dendritic cells do not belong to cytotoxic T cells but express CD8 protein as well.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics-heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5 hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5 hmC were found in CpG islands associated with transcriptional regulators and in long interspersed nuclear elements. It is suggested that these regions might undergo epigenetic reprogramming in embryonic stem cells.

It is commonly thought that immune cell quantification is relatively easy and fully standardized, since the non-adherent, non-matrixed cells in peripheral blood can be marked with antibodies and flow-cytometrically quantified. Providing that cells are non-adherent, single cell suspensions, intact and cell-type specific surface antigens are available, flow cytometry is indeed a highly accurate cell quantification tool.

However, for many applications in research and medical routine, the named prerequisites for such precise measurements are not given:

1. Often, the material/samples measured are not derived from peripheral blood and thus the solubility and single cell suspension property is not met. This is, for example, true for all biopsy analyzes, such as performed in the pathological routine.

2. Even if the analyte is peripheral blood, the prerequisite of having intact cells is difficult to meet, since—in order to maintain their structural integrity ("intactness")—these cells must not be frozen or stored as EDTA-blood for more than 6 hours, before subfractions, such as granulocytes start disintegrating.

3. In contrast to the common perception, there are not highly specific (surface) antigens for all immune cell types and hence the identification of cell types is not as unambiguous as may be hoped. Since antigen expression is not a digital process, thresholds must be defined to decide, whether cells belong to the positive or negative fraction. For T cells, this problem is particular apparent:

Hence, for many applications the current methodological approaches for a quantitative determination of immune cells remain problematic, such as for routine testing in clinical applications, which usually requires some lag times, and hence robustness and stability of the analyte. As said, the flow cytometric methods used for measurement of cells in peripheral blood are not adequate for immune cells infiltrating other tissues, including solid tissues during tumor development or at/after inflammation. Hence, flow cytometric methods are not applied in these areas and the surrogate methods (mostly immune histochemistry) are at most semi-quantitative methods.

Hamerman et al. (in: Hamerman J A, Page S T, Pullen A M. Distinct methylation states of the CD8 beta gene in peripheral T cells and intraepithelial lymphocytes. J Immunol. 1997 Aug. 1; 159(3):1240-6) describe the CD8 co-receptor as expressed on both immature and mature T cells as either an alpha-beta heterodimer or an alpha alpha homodimer. Thymocytes and peripheral T cells express CD8 alpha-beta, whereas TCR alpha-beta+ intraepithelial lymphocytes (IEL) express CD8 alpha alpha or CD8 alpha-beta, and the majority of TCR gamma-delta+ IEL bear CD8 alpha alpha. The presence of CD8 beta enhances the signaling and adhesion properties of the CD8 alpha-beta coreceptor and is necessary for efficient T cell development in the thymus, but is not required for the extrathymic maturation of CD8 alpha alpha+ IEL. To address whether CD8 alpha alpha+ IEL express CD8 beta during their development, Hamerman et al. examined the methylation state of cytosines in the CD8 beta gene 5' regulatory region to identify those for which the methylation state inversely correlates with expression of the CD8 beta protein. They identified four such cytosines that were demethylated in CD8 beta-expressing thymocytes and T cells. Interestingly, these cytosines were also demethylated in CD4+ lymph node T cells that had transiently expressed CD8 beta during their development. The methylation state of these cytosines was examined in DNA purified from TCR alpha-beta+ CD8 alpha alpha+ and TCR alpha-beta+ CD8 alpha-beta+ IEL, as well as from TCR gamma-delta+ CD8 alpha alpha+ and CD3− CD8 alpha alpha+ IEL. The methylation pattern for TCR alpha-beta+ CD8 alpha alpha+ IEL DNA was distinct from that seen for DNA from CD4+ lymph node cells, suggesting that TCR alpha-beta+ CD8 alpha alpha+ IEL have not previously expressed CD8 beta. Analysis of DNA from CD3− CD8 alpha alpha+ IEL indicated that the unique methylation pattern of the CD8 beta gene in TCR alpha-beta+ CD8 alpha alpha+ IEL DNA was not due to transcription of the CD8 alpha gene or the influence of the gut microenvironment.

EP 1 213 360 describes a method of identifying a cell, tissue or nucleus, comprising collecting information on the methylation pattern of DNA isolated from the cell, tissue or nucleus and analyzing the resultant information.

WO 2008/132755 describes a test kit method for estimating CD4+/CD8+ T-cells based on anti-CD4+, anti-CD8+ monoclonal antibody detection carried out on microscopic glass slide. Additional staining visualizes T-cells to further enumeration under a microscope.

WO 02/083162 describes a method to treat, inhibit or prevent immune-driven rejection of grafted tissue or cells in a recipient host by administering a pharmaceutically effective amount of CD8+ T cell inhibitory agent.

EP 2058399 describes methods and reagents for vaccination which generate a CD8 T cell immune response.

EP 1753452 describes a method for altering the CD4/CD8 ratio and the mononuclear cellular infiltrate into a tumor whereby CD8 T cell level strongly decreases.

EP 1616016 describes gene therapy vectors having reduced immunogenicity based on CD8 alpha-chain finding use in extending the survival of transplant allografts and treating graft versus host disease in transplant recipients.

The above mentioned inventions require precise quantification on CD8 and it s subpopulations, which the present invention provides by a new methodology to effectively detect and quantify CD3+CD8+ and/or CD3+/−CD8+ cells, in particular for the first time detect and quantify CD8+ beta cells. Moreover the present invention enables flexible preclinical time framing which is not dependent on quick sample processing but rather allows long term sample storage and individual coordination between sample collecting and sample processing.

Furthermore, the publications of Melvin et al. (Hypomethylation in IFN-Gamma Gen correlates with expression of IFN-G, including CD8 cells, Eur J Immunol. 1995 February; 25(2):426-30), Landolfi M M et al. (CD2−CD4−CD8− lymph node T lymphocytes in MRL lpr/lpr mice are derived from a CD2+CD4+CD8+ thymic precursor J Immunol. 1993 Jul. 15; 151(2):1086-96), and Carbone A M et al. (Demethylation in CD8 suggests that CD4+ derives from CD8+ cells. Role of methylation pattern during cell development. Science. 1988 Nov. 25; 242(4882):1174-6) disclose methylation in connection with expression and differentiation.

WO 2008/132755 describes the identification of CD8 using immune histological methods.

While the measurement and determination of CD8+ cells is generally easy and is usually achieved through analyzing the expression of CD8 on the cellular surface, clinically, it remains challenging to specifically detect, identify, discriminate, and quantify actual CD3+CD8+ alpha/beta cells from whole CD8+ cells. Currently, clinical routine application is limited to the detection of CD8+ cells via detection of CD8 alpha and therefore lacks an established method to differentiate between CD3+CD8+ and CD3+/−CD8+ as well as to detect CD8 beta.

In view of the above, it is an object of the present invention to provide an improved and in particular robust method based on cytosine bisulfite convertibility analysis as a superior tool in order to more conveniently and reliably detect, identify, discriminate, and quantify CD3+/− subpopulations of CD8+ cells.

The present invention solves the above object by providing method for identifying subpopulations of cytotoxic T cells, comprising analyzing the bisulfite convertibility of at least one CpG position in a gene selected from the group of CD8$^+$ alpha and CD8$^+$ beta, wherein a bisulfite convertibility of at least one CpG position in the CD8$^+$ beta gene is indicative for a CD3+CD8+ cytotoxic T cell, and a bisulfite convertibility of the CD8$^+$ alpha gene is indicative for a CD3+/−CD8+ cytotoxic T cell.

Currently, no data describing CD8+ beta/beta cells exists. However, in a preferred embodiment thereof, the present invention for the first time will allow detection of such cells. Moreover, it is expected that the novel marker for CD8 beta will reveal new scientific insight into cell origin and cell state of CD8 beta chain expressing cells.

Currently, it is described in the literature that CD3+CD8+ NKT cells express the CD8 beta chain. However, the results of the present inventors indicate that for a portion of these cells there may exist a different epigenetic regulation that does not simply reflect or correspond to the currently known protein expression pattern.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=a/b a=Σ(C and/or mC and/or hmC and/or fC and/or cC)
b=Σ(C and/or mC and/or hmC and/or fC and/or cC),
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

The present invention is based on the surprising identification of a region of the CD8 gene by the inventors, namely the CD8 beta and alpha gene region, as specific epigenetic markers, allowing for the first time the identification of CD8 subpopulations of CD8 beta and alpha chain bearing cells as well as the clinical routine application of said analysis.

In the context of the present invention, the genomic region according to SEQ ID No. 1 is herein designated "CD8 beta chain specific bisulfite convertible region", which allows the identification of CD3+CD8+ cytotoxic T cells (alpha/beta CD8+ cells), and the genomic region according to SEQ ID No. 2 is herein designated "CD8 alpha chain specific bisulfite convertible region", which allows the identification of CD3$^{+/-}$CD8$^+$ cells (alpha/alpha CD8+ cells). Surprisingly, the discriminatory pattern of bisulfite convertible and non-convertible cytosine is exclusively limited to the genomic region according to SEQ ID No. 1 for CD8 beta bearing CD8+ cells as shown using the amplicons according to SEQ ID No. 5 and/or SEQ ID No. 6, and to the genomic region according to SEQ ID No. 2 for CD8 alpha bearing CD8+ cells as shown using the amplicon according to SEQ ID No. 7.

In a preferred embodiment of the method according to the present invention, both genes for CD8$^+$ alpha and CD8$^+$ beta are analyzed, preferably by analyzing amplicons derived from SEQ ID No. 1 and SEQ ID No. 2, and/or the CD8alpha specific non-methylated region derived from SEQ ID No. 3 and/or the CD8beta specific non-methylated region derived from SEQ ID No. 4.

In a preferred embodiment of the method according to the present invention for identifying a subpopulation of cytotoxic T cells (identification of CD3+CD8+ cells), said at least one CpG position is selected from a CpG position in an amplicon according to SEQ ID No. 2 and 3, and is preferably selected from positions 67, 92, 116, 123, 133, 161, 199, 231, 255, 267, and 291 in the amplicon No. 2004 according to SEQ ID No. 7 (CD8 alpha Assay), and positions 40 63 95 135 142 169 194 213 216 232, 245, 273, 339, 345, and 393 in the amplicon No. 2007 according to SEQ ID No. 5, and positions 165, 196, 219, 267, 277, 307, 314, 341, and 410 in the amplicon No. 2008 according to SEQ ID No 6 (CD8 beta Assays).

The inventive concept is based on the specific bisulfite convertibility of the CD8 beta and CD8 alpha specific region in CD8 positive cells. Using a simple and precise quantitative PCR method, the inventors show that specific pattern of cytosine modification of the said gene regions represents a specific marker for CD3+CD8+ and CD3+/−CD8+ cell counts in blood or tissues. In one preferred embodiment, one highly discriminative region of the CD8 beta and CD8 alpha gene is designated by the nucleotide sequence according to SEQ ID No. 3, and SEQ ID No. 4, which displays differential bisulfite convertibility when alpha/beta and alpha/alpha CD8+ cells are compared with all other cells.

The inventors could demonstrate that in the CD8 beta bearing cells the CpG motifs are almost completely convertible by bisulfite (i.e. to more than 70%, preferably 80%, preferably, more than 90% and most preferred more than 95%), whereas the same motifs are completely methylated in all CD8⁻ and alpha/alpha CD8+ cells. In the same context, the inventors could demonstrate that in the CD8 alpha bearing cells the CpG motifs are almost completely convertible by bisulfite as well (i.e. to more than 70%, preferably 80%, preferably, more than 90% and most preferred more than 95%), whereas the same motifs are completely methylated in all CD8⁻ cells.

The differential methylation of the CpG motifs within the aforementioned regions correlates with expression of CD8 alpha and beta chains. Thus, determination of the bisulfite convertibility of the CD8 alpha and beta locus is a valuable tool to identify subpopulations of CD8+ cells, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of CD8+ subpopulations without purification or any staining procedures. It even reports in solid tumors or other solid tissues the number of cells bisulfite convertible in said region, thus showing the total amount of tumor infiltrating CD8+ subpopulations.

The inventors found a bisulfite convertibility at the human CD8 beta and alpha locus to be restricted to CD3+CD8+ and CD3+/−CD8 cells, respectively, when tested against all major peripheral blood cell types. These data indicated that epigenetic modifications in the CD8 beta and alpha locus serve as valuable markers for the identification CD8+ subpopulations, regardless of the expression of both, CD8 beta and alpha chain.

Another preferred aspect of the method according to the present invention then further comprising a quantification of the relative amount of CD3+CD8+ and/or CD3+/−CD8+ cells based on comparing the relative amount(s) of bisulfite convertible DNA in regions specific for CD8 alpha and/or beta with the relative amount(s) of non-bisulfite convertible DNA of cell-specific regions. Said quantification thus is achieved based on the ratio of the bisulfite convertible DNA to non-convertible DNA in the genetic regions of CD8 beta and alpha as described and analyzed herein. Most preferred is a quantification of the relative amount of CD3+CD8+ and/or CD3+/−CD8+ cells is based on an (preferably parallel or simultaneous) analysis of the relative amount of bisulfite convertible DNA of cell-specific regions for CD8 alpha and/or beta, and of the relative amount of bisulfite convertible DNA of cell-unspecific genes (preferably designated "control genes" or "control regions", such as, for example, the gene for GAPDH). The analysis preferably further comprises an analysis of the bisulfite convertibility of at least one CpG position in a gene selected from cell-specific genes of CD3 T cells, CD4 T cells, regulatory T cells, monocytes, granulocytes, B cells, GAPDH, Th1, Th2, Th9, Th17, Th22, Tfh, NKT, and NK. In some embodiments, ratios of markers and respective numbers and/or amounts of cells can be determined and established based on, at least in part, the present analysis, for example of CD8+ beta to CD8+ alpha, overall CD8+ (alpha+ beta) to overall CD3+, CD8+ beta to CD3+, CD8+ alpha to CD3+, and/or CD3+CD8+ to CD3+CD4+, and/or CD8+ beta or CD8+ alpha to Treg or overall CD8+ to Treg cells and/or markers, in a sample to be analyzed.

In a further preferred embodiment of the method according to the present invention, said analysis of bisulfite convertibility comprises amplification with at least one primer of suitable primer pairs that can be suitably designed based on SEQ ID No. 1 or SEQ ID 2, preferably oligomers according to any of SEQ ID No. 8 to 13.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the CD8 beta and alpha gene is produced that is a particularly preferred "tool" for performing the method(s) according to the present invention. Consequently, oligomers according to any of SEQ ID No. 8 to 13 or an amplicon as amplified by a primer pair based on SEQ ID No. 1 or 2 as mentioned above constitute preferred embodiments of the present invention.

The person of skill will furthermore be able to select specific subsets of CpG positions in order to minimize the amount of sites to be analyzed, for example at least one of CpG position 40, 63, 95, 135, 142, 169, 194, 213, 216, 232, 245, 273, 339, 345, 393, 165, 196, 219, 267, 277, 307, 314, 341, and 410 of the CD8⁺ beta specific bisulfite convertible region (SEQ ID No. 1 or 4), or all sites as present on the CD8⁺ beta specific bisulfite convertible region according to SEQ ID No 1 or 4. The positions are numerically counted from the 5'-end of an amplicon (e.g. positions 40, 63, 95, 135, 142, 169, 194, 213, 216, 232, 245, 273, 339, 345, and 393 in the amplicon No. 2007 according to SEQ ID No. 5, and positions 165, 196, 219, 267, 277, 307, 314, 341, and 410 in the amplicon No. 2008 according to SEQ ID No. 6) as generated and analyzed. Preferred are combinations of 3, 4, 5, 6, 7, 8, 9, or 10 positions, the analysis of which produces sufficient data and/or information in order to be informative in the context of the present invention, such as, for example, positions 142, 169, 194, 213, 216, 232, 245, 273, in the amplicon No. 2007 according to SEQ ID No. 5.

The person of skill will furthermore be able to select specific subsets of CpG positions in order to minimize the amount of sites to be analyzed, for example at least one of CpG position 67, 92, 116, 123, 133, 161, 199, 231, 255, 267, and 291 of the CD8$^+$ alpha specific bisulfite convertible region (SEQ ID No. 2 or 3), or all sites as present on the CD8$^+$ alpha specific bisulfite convertible region according to SEQ ID No 2 or 3. The positions are numerically counted from the 5'-end of an amplicon (e.g. positions 67, 92, 116, 123, 133, 161, 199, 231, 255, 267, and 291 in the amplicon No. 2004 according to SEQ ID No. 7) as generated and analyzed. Preferred are combinations of 3, 4, 5, 6, 7, 8, 9, or 10 positions, the analysis of which produces sufficient data and/or information in order to be informative in the context of the present invention, such as, for example, positions 116, 123, 133, 161, 199, 231, 255, 267 in the amplicon No. 2004 according to SEQ ID No. 7.

In order to analyze the bisulfite convertibility of CpG positions, any known method to analyze DNA modification can be used. In a preferred embodiment of the method according to the present invention, the analysis of the DNA modification comprises a method selected from single molecule real-time technology (SMRT), DNA-modification-dependent polymerase kinetics, DNA sequencing through nanopores, strand sequencing, exonuclease sequencing, DNA-modification-dependent DNA hybridization, methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said CD3+CD8$^+$ and CD3+/−CD8+ cells from all major peripheral blood cell types and/or non-blood cells, preferably, but not limited to, from CD19$^+$ B lymphocytes, CD3$^+$CD8$^+$ T-Cells, CD15$^+$ granulocytes, CD14$^+$ monocytes, CD56$^+$ Natural Killer Cells and CD3$^+$CD56$^+$ Natural Killer T-Cells, and CD3+CD4+ T helper cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, rat, monkey or human. The samples can be suitably pooled, if required.

Another preferred aspect of the method according to the present invention then further comprises the step of concluding on the immune status of said mammal based on said CD8+ subpopulations. The CD8$^+$ subpopulations can be quantified and be used as a benchmark to relatively quantify further detailed subpopulations (as but not limited to CD4, Th1, Th2, Th9, Th17, Th22, Treg, Tth), or it can be used as a predictive and/or screening and/or diagnostic and/or prognostic and/or adverse events detecting factor, or it can be used to finally detect this population to determine the overall immune activity status.

Another preferred aspect of the method according to the present invention is directed at the use of cytosine modification analysis of cell specific genes for CD3+, CD4+, regulatory T cells, Th1, Th2, Th9, Th17, Th22, Tfh, NKT, NK, monocytes, granulocytes and/or B cells for the detection and quality assurance and control of alpha/beta and/or alpha/alpha CD8+ cells.

In yet another preferred embodiment of the methods according to the present invention, the mammal suffers from or is likely to suffer from autoimmune diseases, transplant rejections, infection diseases, cancer, and/or allergy as but not limited to *Trypanosoma cruzi*-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of CD3+ CD8+ and/or CD3+/−CD8+ cells in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said subpopulations of CD8+ cells as e.g. a sample for cell transfer into a patient.

Another preferred aspect of the method according to the present invention then relates to a method as above, further comprising formulating said subpopulation of cells as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID No. 8 to 13, an oligomer designed based on SEQ ID No. 1 or 2, the CD8 alpha and/or beta gene specific non-methylated region according to SEQ ID No. 3 or 4 or an amplicon selected from any of SEQ ID No. 3 to 7.

Yet another preferred aspect of the present invention then relates to a kit for identifying and/or monitoring said CD8 subpopulations (CD3+CD8+ cells and/or CD3+/−CD8+ cells) in a mammal based on the analysis of the bisulfite convertibility of at least one CpG position in the CD8 beta and CD8 alpha cell specific bisulfite convertible gene regions according to SEQ ID No. 1 and 2, respectively, and/or at least one amplicon selected from any of SEQ ID No. 3 to 7, respectively, comprising materials for performing a method according the present invention as described herein. Preferably, said kit comprises a) a bisulfite reagent, and b) materials for the bisulfite convertibility analysis of at least one CpG position selected from the positions 67, 92, 116, 123, 133, 161, 199, 231, 255, 267, and 291 in the amplicon No. 2004 according to SEQ ID No. 7, and positions 40, 63, 95, 135, 142, 169, 194, 213, 216, 232, 245, 273, 339, 345, and 393 in the amplicon No. 2007 according to SEQ ID No. 5, and positions 165, 196, 219, 267, 277, 307, 314, 341, and 410 in the amplicon No. 2008 according to SEQ ID No. 6. Further preferred, the positions consist of all positions in the CD8+ cell specific non-methylated region according to SEQ ID No. 1 and 2, respectively, and/or said amplicons according to any of SEQ ID Nos. 3 to 7, or positions 142, 169, 194, 213, 216, 232, 245, 273, in the amplicon No. 2007 according to SEQ ID No. 5 and/or positions 116, 123, 133, 161, 199, 231, 255, 267 in the amplicon No. 2004 according to SEQ ID No. 7.

The present invention also encompasses the use of oligomers or amplicon or a kit according to the present invention for identifying and/or for monitoring CD3+CD8+ and/or CD3+/−CD8+ cells in a mammal as described herein.

In summary, using the CD8 beta and alpha marker, the inventors very specifically identified, quantified and particularly differentiated both CD8 positive cells as such and its subpopulations, and in their relation to other cell types in a sample, for example to overall T-lymphocytes using the epigenetic markers for CD3, or their association to the CD4 T helper cells using the marker CD4. By such means for example CD4 positive T-lymphocytes could then be further distinguished from CD8 lymphocytes. This was not possible before the invention, since the protein expression of the marker CD8 beta and alpha cannot be used to reliable identify and quantify CD8 positive alpha/beta and alpha/alpha cells, nor was it possible from a (fresh, embedded or frozen) whole blood or tissue sample without specific means of conservation to provide a routine technology for the quantification of these cell types. Additionally, up to now no marker for CD8+ alpha/beta cells was discovered to identify and quantify said cells.

The invention will now be further described based on the following examples and with reference to the accompanying figures and the sequence listing, without being limited thereto. For the purposes of the present invention, all references as cited herein are incorporated by reference in their entireties. In the Figures and Sequences,

SEQ ID No. 1 shows the CD8 beta chain specific bisulfite convertible region according to the present invention.

SEQ ID No. 2 shows the CD8 alpha chain specific bisulfite convertible region according to the present invention.

SEQ ID No. 3 shows the sequence of the CD8A specific non-methylated region (alpha); the sequence contains discriminatory amplicon 2004 (AMP2004), and is confined at the 5' and 3' end by the non-discriminatory AMP 2003 and AMP2005, respectively.

SEQ ID No. 4 shows the sequence of the CD8B specific non-methylated region; the sequence contains discriminatory overlapping amplicons AMP2007 and AMP2008. The sequence is confined at the 3' end by the non-discriminatory amplicons AMP2011 and AMP1479 (near the CD8alpha gene).

SEQ ID No. 5 and SEQ ID No. 6 show the sequences of amplicons Amp 2007 and Amp 2008 for CD8 beta (overlapping), respectively.

SEQ ID No. 7 shows the sequence of amplicon Amp 2004 for CD8 alpha.

SEQ ID No. 8 to SEQ ID No. 13 show the sequences of specific oligomers according to the present invention.

SEQ ID No. 14 to SEQ ID No. 25 show the sequences of specific oligomers according to the present invention; SEQ ID No. 14 shows the forward Primer (nmF1.3) for AMP 2007; SEQ ID No. 15 shows the reverse primer (nmR1.5) for AMP 2007; SEQ ID No. 16 shows the forward primer (mF1.3) for AMP 2007; SEQ ID No. 17 shows the reverse primer (mR1.9) for AMP 2007; SEQ ID No. 18 shows the probe (nmP1.2), and SEQ ID No. 19 shows the probe (mP1.2); SEQ ID No. 20 shows the genomic sequence/position forward primer (nmF1.3) for AMP 2007; SEQ ID No. 21 shows the genomic sequence/position of reverse primer (nmR1.5) for AMP 2007; SEQ ID No. 22 shows the genomic sequence/position of forward primer (mF1.3) for AMP 2007; SEQ ID No. 23 shows the genomic sequence/position of reverse primer (mR1.9) for AMP 2007; SEQ ID No. 24 shows the genomic sequence/position of probe (nmP1.2) for AMP 2007, and SEQ ID No. 25 shows the genomic sequence/position of probe (mP1.2) for AMP 2007.

EXAMPLES

Example 1

The inventors have purified various blood subsets by FACS sorting including B cells (CD3− CD8−)(BLC), cytotoxic T lymphocytes (CD3+CD8+)(CTL), CD3−CD8− granulocytes (GRC) and CD3−CD8− monocytes (MOC), NK cells (CD3−CD8+)(NKC), NKT cells (CD3+CD8+) (NKT11), CD3+CD8− NKT cells (NKT14), and T helper cells (CD3+CD8−) (THC). DNA from the purified cells was bisulfite-treated and analyzed at various CpG dinucleotide motifs within the CD8 alpha and the CD8 beta gene. The inventors then compared the bisulfite convertibility (T for cytosine that was not-methylated in the original sequence versus finding C as for Cytosine that was methylated in the original (genomic) sequence).

Figure 1:
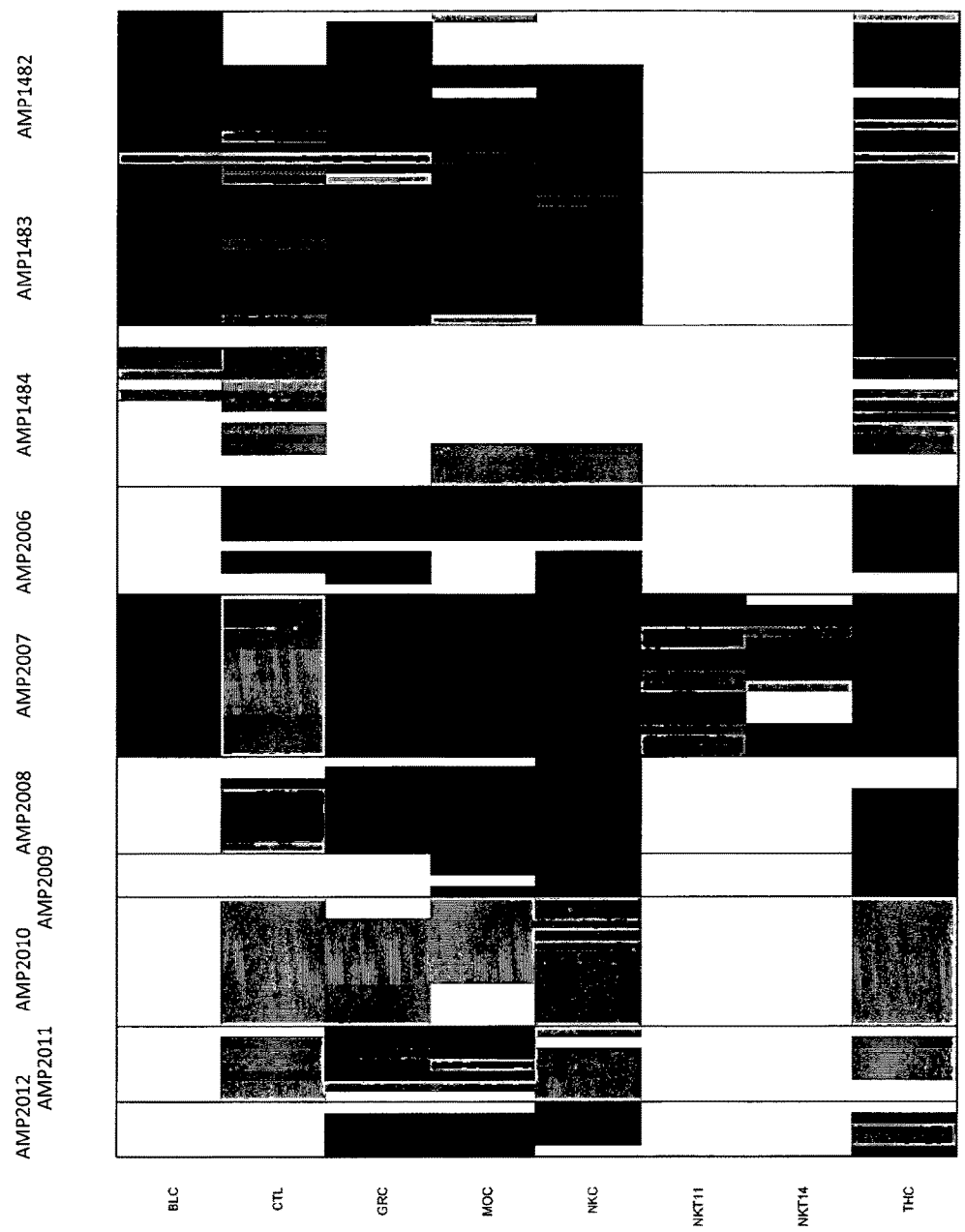
FIG. 1 shows the analysis of CpG sites on amplicons No. 1482, No. 1483, No. 1484, No. 2006, No. 2007 (SEQ ID No. 3), No. 2008, No. 2009, No. 2010, No. 2011, and No. 2012, respectively, within the CD8 beta gene. The numbers on the left indicate the respective CpG position on the respective amplicon. The abbreviations at the bottom indicate B cells (CD3− CD8−)(BLC), cytotoxic T lymphocytes (CD3+CD8+)(CTL), CD3−CD8− granulocytes (GRC) and CD3−CD8− monocytes (MOC), NK cells (CD3−CD8+)(NKC), NKT cells (CD3+CD8+)(NKT11), CD3+CD8− NKT cells (NKT14), and T helper cells (CD3+CD8−)(THC), respectively.

The CD8 beta data (FIG. 1) showed various CpG positions in the Amp 2007 of CD8 beta gene (see SEQ ID No. 1) that were non-methylated in CD3+CD8+ cytotoxic T-cells and partially non-methylated in CD3+CD8+ NKT cells while methylated in all other analyzed blood cell types. The differentially cytosine modified gene region Amp 2007 for CD8 beta is shown in SEQ ID No. 5.

Currently, it is described in the literature that CD3+CD8+ NKT cells express the CD8 beta chain. However, the results of the present inventors indicate that for a portion of these cells there may exist a different epigenetic regulation that does not simply reflect or correspond to the currently known protein expression pattern. This was also shown earlier for Treg cells and Th17 cells (see EP1826279 and PCT/EP2012/070676, both herewith incorporated by reference). Moreover, it is expected that the novel marker for CD8 beta will reveal new scientific insight into cell origin and cell state of CD8 beta chain expressing cells.

Figure 2:
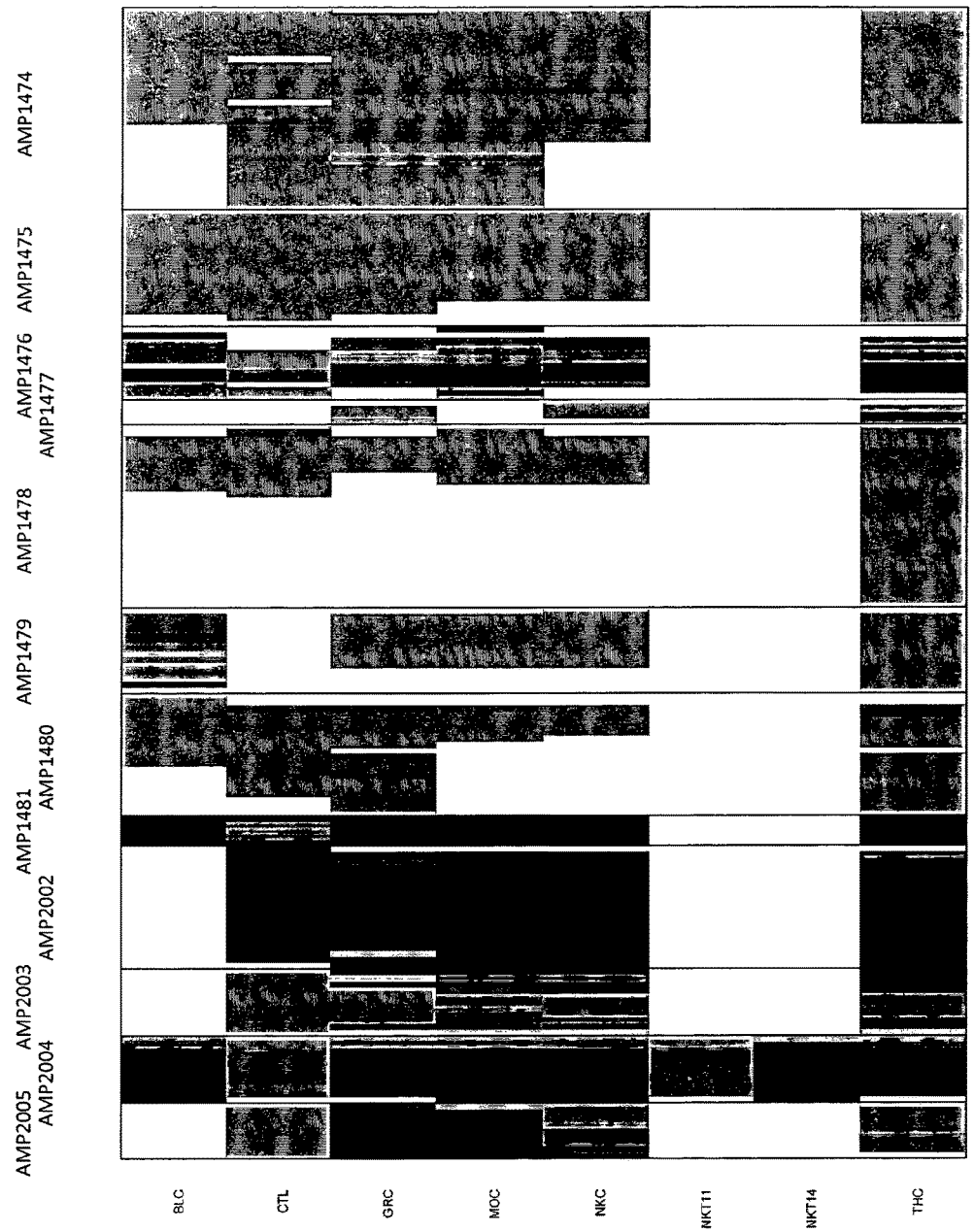
FIG. 2 shows the analysis of CpG sites on amplicons No. 1474, No. 1475, No. 1476, No. 1477, No. 1478 (SEQ ID No. 3), No. 1479, No. 1480, No. 1481, No. 2002, No. 2003, No. 2004, and No. 2005, respectively, within the CD8 alpha gene. The numbers on the left indicate the respective CpG position on the respective amplicon. The abbreviations at the bottom indicate B cells (CD3−CD8−)(BLC), cytotoxic T lymphocytes (CD3+CD8+)(CTL), CD3−CD8− granulocytes (GRC) and CD3−CD8− monocytes (MOC), NK cells (CD3− CD8+)(NKC), NKT cells (CD3+CD8+)(NKT11), CD3+CD8− NKT cells (NKT14), and T helper cells (CD3+CD8−)(THC), respectively.
Figure 3:
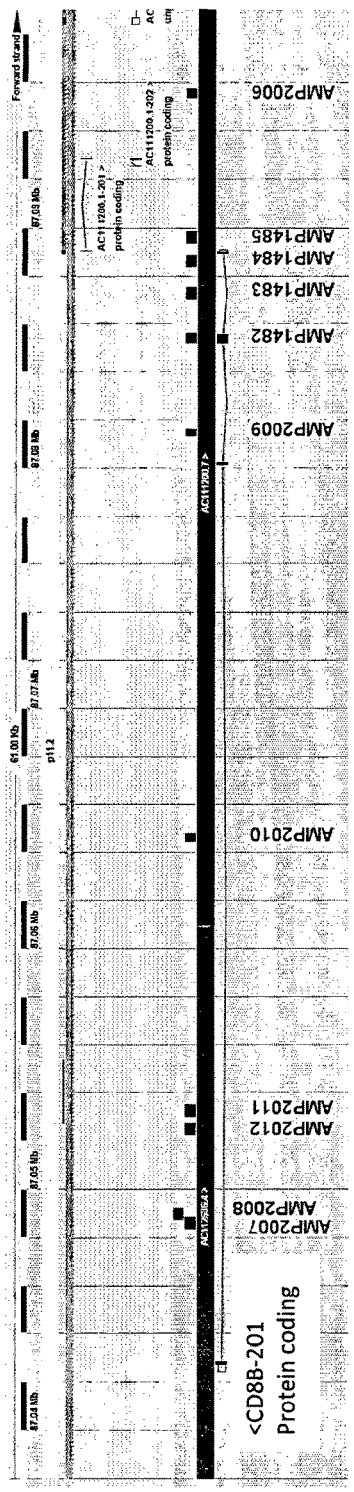
FIG. 3 shows the position of the specific bisulfite convertible regions within the CD8 beta gene according to the present invention, and the alignments of amplicons as analyzed (gray squares) against this region.
Figure 4:
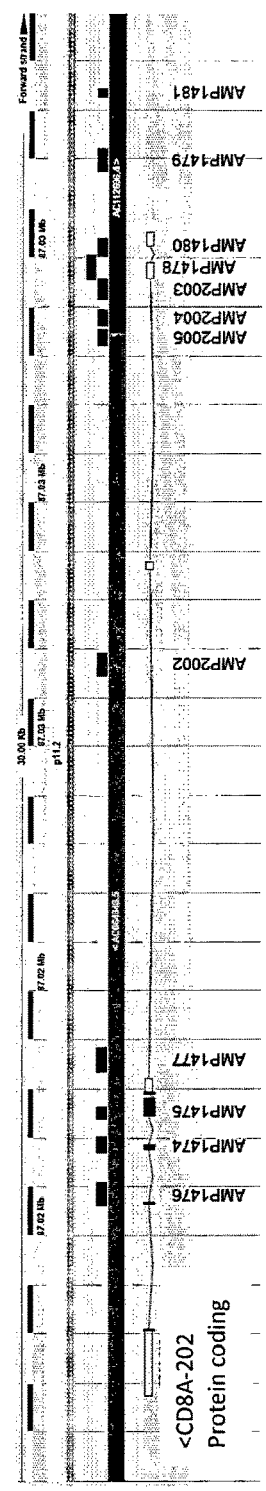
FIG. 4 shows the position of the specific bisulfite convertible regions within the CD8 alpha gene according to the present invention, and the alignments of amplicons as analyzed (gray squares) against this region.

The CD8 alpha data (FIG. 2) showed various CpG positions in the Amp 2004 of the CD8 alpha gene (see SEQ ID No. 2) that were non-methylated in CD3+CD8+ cytotoxic T-cells and in CD3+CD8+ NKT cells while methylated in all other analyzed blood cell types. The differentially cytosine modified gene region Amp 2004 for CD8 alpha is shown in SEQ ID No. 7. Similar to the bisulfite conversion pattern of CD8 beta, also for the CD8 alpha gene there was a partial methylation found for cells that in the literature are described as CD8 alpha protein expressing cells (NK cells). FACS sorting via protein expression does not reflect actual epigenetic regulation status. Future scientific studies on the epigenetic pattern in the CD8 alpha gene using the present epigenetic CD8 alpha marker will further deepen the understanding of e.g. origin and state of said cells.

Example 2: Assessment of CD8+ CD3+ T-Cells in Human Peripheral Blood

Novel epigenetic assays were compared with flow cytometry assays for the detection of CD8 and CD3 cells and ratios thereof. As both techniques determine the same biological variable, they should be essentially concordant.

Human peripheral blood was obtained from healthy volunteers. DNA from venous blood was purified using DNeasy Blood&Tissue Kit (Qiagen) according to manufacturer instructions. Additionally, capillary blood was spotted on FTA® Cards (Whatman) and dried at room temperature overnight. DNA was extracted from 6×6 mm spots using QIAamp DNA Kit (Qiagen). Following, DNA was bisulfite converted: Up to 1.5 µg genomic DNA were converted applying Epitect (Fast) Bisulfite Kits (Qiagen) according to manufacturer's protocol. Whole blood DNA was purified using a Microcon®-30 Centrifugal Filter (Millipore). qPCR: Highly cell-type specific methylation-dependent qPCRs for quantification of $CD3^+$ and $CD8^+$ T-cells were developed and performed as follows: One set of oligonucleotides (i.e., forward/reverse primer and hydrolysis probe) specific for TpG- or CpG-variant was used. Reactions were carried out in triplicates in 10 µl total volume using 2×Probe Mastermix (Roche), 15 pmol of each primer, 1.25-2.5 pmol probe, 25 ng λ-DNA (NEB) and up to 82 ng template DNA or plasmid at 1×95° C. 10 min, and 50 cycles 95° C. 15 sec and 61° C. 60 sec. For CD8B TpG, $MgCl_2$ was added to a final concentration of 4.7 mM. Amplification crossing points were determined using LightCycler480 software (Roche) deploying the second-derivative maximum method. Percental target cells were calculated as previously described (Sehouli, J. et al. 2011. Epigenetic quantification of tumor-infiltrating T-lymphocytes. *Epigenetics* 6:236-246). For blood samples, normalization of qPCR values $(x_N)$ was carried out as follows: $x_N = qPCR_x/qPCR_{Cal} * FCM_{Cal}$ using a calibrator (Cal) with a determined FCM value ($FCM_{Cal}$). Plasmids: Synthesized target regions for real-time qPCR assays were inserted into plasmid pUC57 or pJet1.2 (Genscript Inc.). Linearized plasmids were diluted in 10 ng/µl of λ-phage DNA (NEB) to obtain qPCR standards of 31250, 6250, 1250, 250, 50, and 30 copies per reaction.

Oligonucleotides: qPCR: The sequences of amplification primers are as follows:

```
                                       (SEQ ID No. 14)
   Forward Primer (nmF1.3) AMP 2007:
   GGT TAA GAA ATT AAT AGG AAA AAG AAT (SEQ ID No. 15)
   Reverse primer (nmR1.5) AMP 2007:
   CTT CCC CAC CAC AAT ACA ACA (SEQ ID No. 16)
   Forward primer (mF1.3) AMP 2007:
   GGT TAA GAA ATT AAT AGG AAA AAG AAC (SEQ ID No. 17)
   Reverse primer (mR1.9) AMP 2007:
   CCC CAT ATT ACT TCC CCG
```

The sequences of probes are as follows:

```
   Probe (nmP1.2):
                                       (SEQ ID No. 18)
   TGT TTG TGA GGT ATT TAG TTG ATG GGA GTT TTG Probe (mP1.2):
                                       (SEQ ID No. 19)
   CGT TTG TGA GGT ATT TAG TCG ACG GGA G
```

Genomic positions of amplification primers and probes are as follows:

```
   Genomic forward Primer (nmF1.3) AMP 2007
                                       (SEQ ID No. 20)
   GGTTAAGAAACCAACAGGAAAAGAAC
```

```
                                                   (SEQ ID No. 21)
Reverse primer (nmR1.5) AMP 2007:
CGTTGTATTGTGGCGGGGAAG (SEQ ID No. 22)
Forward primer (mF1.3) AMP 2007:
GGTTAAGAAACCAACAGGAAAAAGAAC (SEQ ID No. 23)
Reverse primer (mR1.9) AMP 2007:
CGGGGAAGCAACATGGGG (SEQ ID No. 24)
Probe (nmP1.2) AMP 2007:
CGCCTGTGAGGCACTCAGCCGACGGGAGCTTTG (SEQ ID No. 25)
Probe (mP1.2) AMP 2007:
CGCCTGTGAGGCACTCAGCCGACGGGAG
```

CD3- and GAPDH-qPCR positions of amplification primers and probes were described previously (Sehouli, J. et al. 2011. Epigenetic quantification of tumor-infiltrating T-lymphocytes. *Epigenetics* 6:236-246).

Flow cytometry: Cell sorting: Peripheral blood samples were fractionated in a MACS/FACS sorting protocol (Baron, U., Floess, S., Wieczorek, G., Baumann, K., Grützkau, A., Dong, J., Thiel, A., Boeld, T. J., Hoffmann, P., Edinger, M., et al. 2007. DNA demethylation in the human FOXP3 locus discriminates regulatory T cells from activated FOXP3(+) conventional T cells. *Eur J Immunol* 37:2378-2389.) for granulocytes ($CD15^+$), monocytes ($CD3^-$/$CD14^+$), NK cells ($CD56^+$/$CD16^+$), B cells ($CD19^+$), $CD8^+$ T-cells ($CD3^+$/$CD8^+$/$CD4^-$). Cell counting: 50 µl peripheral blood was stained in TruCount™ tubes (Becton-Dickinson) with anti-CD3 FITC, anti-CD4 PerCP and anti-CD8 APC. After staining and erythrocyte lysis, cells were analyzed on FACS-LSRII (Becton Dickinson). Absolute $CD3^+$ and $CD3^+$ $CD8^+$ T-cell counts per microliter of peripheral blood were calculated by the ratio between analyzed cells and fluorescent TruCount™ beads according to the manufacturer's instructions. Anti-CD45 PE staining was performed for assessment of relative cell counts.

Statistical analysis: For Bland-Altman plots, errors were given in percent (FCM-qPCR). Two-sided t-tests were performed to test if mean differences (bias) were significantly different from zero. Linear regression was performed to obtain slope and intercept. Shapiro-Wilk tests and Q-Q-Plots were used to assess normality assumptions of regression residuals. Residuals were visually inspected with respect to homogenous scattering. P-values <0.05 were considered significant. In ROC analysis optimal cutoff value and accuracy was determined as value minimizing the Euclidean distance to the coordinate point with optimal sensitivity and specificity. All p-values correspond to two-sided tests. Statistics software SPSS 21.0 (IBM) and R 2.14 were employed.

T-cell counts in peripheral blood. Randomly selected and blinded peripheral blood samples from 39 healthy and 86 $HIV^+$ donors were tested with epigenetic assays for CD3 and CD8B and compared with the according Flow-Cytometry (FCM)-based T-cell counting procedures. Healthy and $HIV^+$ subjects had a median age of 55 (range: 19-67) and 46 (range: 23-75) years, respectively. 87.2% of $HIV^+$ subjects were treated with anti-retroviral therapy and 17.4% had opportunistic infections.

Figure 5:
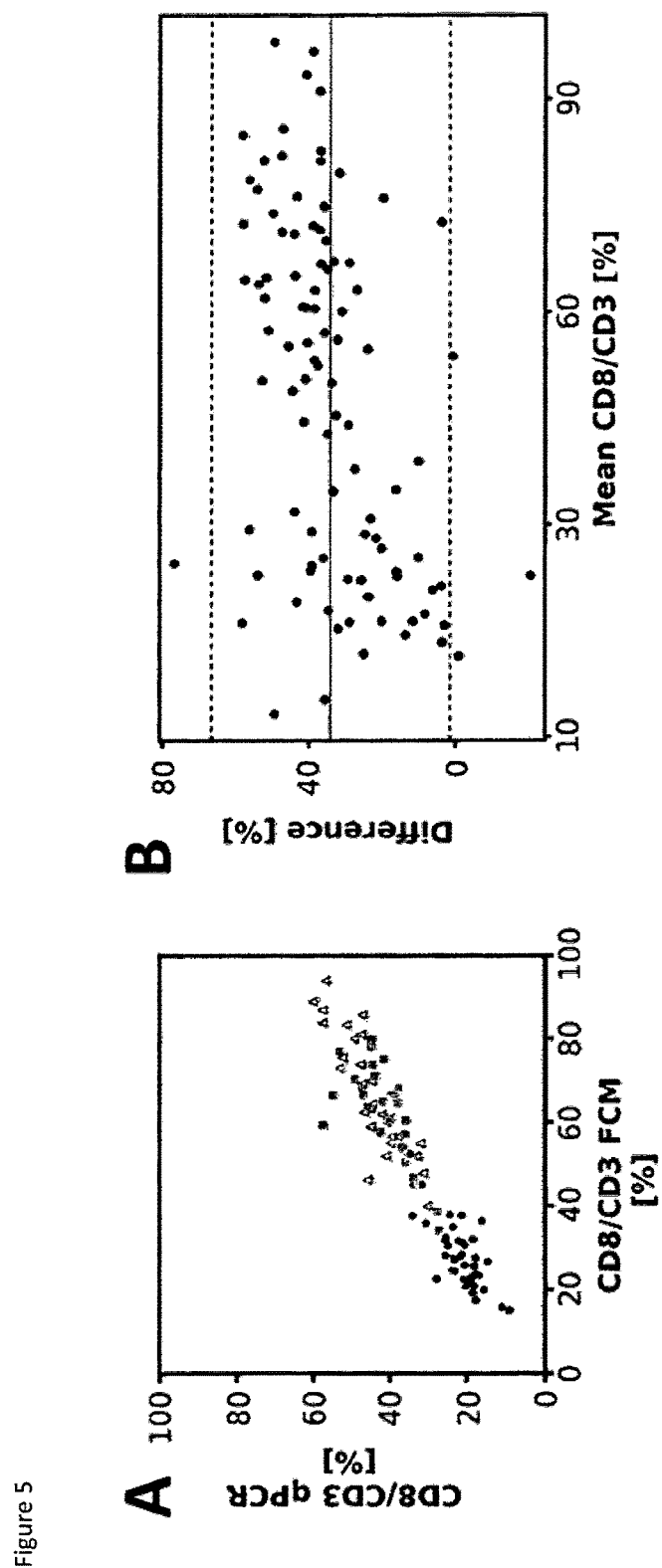
FIG. 5 shows the comparison of qPCR and FCM measurements. (A) Ratio of $CD8^+$ to $CD3^+$ T-cells in (%) as determined by FCM (x-axis) and epigenetic qPCR measurement (y-axis) in peripheral blood of healthy controls (black circles) and $HIV^+$ patients (grey squares; white triangles). (B) Bland-Altman-diagrams for method agreement of $CD8^+$ to $CD3^+$ T-cells. Plotted is the mean of the determined ratios by both methods (x-axis) and the corresponding percentaged differences (FCM-qPCR). The solid line represents the estimated mean difference, dotted lines the estimated upper and lower limits of agreement.

Method agreement for CD8/CD3 ratio. The median CD8/CD3 ratio in healthy subjects was 21.0% in qPCR tests (FCM: 27.6%) ranging from 9.1%-34.7% (FCM: 15.1%-52.6%) while $HIV^+$ patients exhibited a median of 41.5% (FCM: 64.6%) ranging from 25.1%-60.9% (FCM: 34.1%-94.0%, FIG. 5A). Pearson correlation between qPCR and FCM data was at 0.94 ($p<0.001$). The estimated mean difference in the Bland-Altman percent-difference diagram indicated a 34.1% smaller qPCR measurement compared to FCM (LoA: 66.6% and 1.6% (FIG. 5B)). The inventors also tested agreement of epigenetic qPCRs for CD8/CD3 ratio between venous blood and dried capillary blood from six healthy donors (see Table A).

When employing these assays on whole blood, good method agreement between cell ratios obtained by qPCR and FCM was observed. Also, concordance was observed for clinically used FCM- and experimentally determined qPCR-cutoffs. qPCRs were also performed from dried blood spots and showed data equivalent to those from venous blood.

TABLE A

Evaluation of qPCR performance from dried blood spots compared to fresh blood according to Bland-Altman method.

| | CD8/CD3 [%] | |
|---|---|---|
| | Venous blood | DBS |
| Donor 1 | 15.4 | 13.9 |
| Donor 2 | 25.1 | 23.7 |
| Donor 3 | 28.4 | 28.1 |
| Donor 4 | 22.5 | 20.5 |
| Donor 5 | 19.8 | 24.3 |
| Donor 6 | 21.6 | 22.3 |
| Mean | 22.1 | 22.1 |
| MD | | 0.00 |
| upper LoA | | 4.8 |
| lower LoA | | −4.8 |

MD—mean difference, LoA—limits of agreement.

The invention claimed is:

1. A method for identifying CD3+CD8+ cytotoxic T cells in a sample derived from a human, wherein said method comprises:
   i) providing the sample derived from the human comprising immune cells;
   ii) determining the methylation status of at least one CpG position in genomic regions for CD8+ beta consisting of the sequences of SEQ ID NO: 5 and 6, wherein said determining the methylation status comprises the steps of:
      a) isolating genomic DNA from said sample,
      b) treating the isolated genomic DNA with bisulfite,
      c) amplifying a first genomic region in the bisulfite treated genomic DNA with a first primer pair of SEQ ID NOs: 8 and 9 to produce a first amplicon, wherein the first genomic region in the bisulfite treated genomic DNA corresponds to the genomic region consisting of SEQ ID NO: 5, and amplifying a second genomic region in the bisulfite treated genomic DNA with a second primer pair of SEQ ID NOs: 10 and 11 to produce a second amplicon, wherein the second genomic region in the bisulfite treated genomic DNA corresponds to the genomic region consisting of SEQ ID NO: 6,
      d) performing a nucleic acid based assay on said first amplicon to determine the methylation status of the CpG positions 40, 63, 95, 135, 142, 169, 194, 213, 216, 232, 245, 273, 339, 345, and 393 in the first genomic region consisting of the sequence of SEQ ID NO: 5 and performing a nucleic acid based assay on said second amplicon to determine the methylation status of the CpG positions 165, 196, 219, 267, 277, 307, 314, 341, and 410 in the second genomic region consisting of the sequence of SEQ ID NO: 6; and
   iii) identifying the immune cells as CD3+CD8+ cytotoxic T cells when the CpG positions in the first genomic region and the second genomic region are less than 20% methylated.

2. The method according to claim 1, further comprising quantifying the relative amount of said CD3+CD8+ cytotoxic T cells, said quantifying comprising detecting the methylation status of a control gene and comparing said methylation status of the control gene with the methylation status of said CpG positions in SEQ ID NOs: 5 and 6.

3. The method according to claim 1, wherein said nucleic acid based assay is performed on a DNA-chip.

4. The method according to claim 1, wherein said CD3+ CD8+ cytotoxic T cells as identified are further distinguished from cell types selected from the group consisting of CD19+ B lymphocytes, CD15+ granulocytes, CD14+ monocytes, CD56+ natural killer Cells, CD3+CD56+ natural killer T-Cells, and CD3+CD4+ T helper cells by comparing the methylation status of the CpG positions in SEQ ID NOs: 5 and 6.

5. The method according to claim 1, wherein said sample is selected from a body fluid, tissue, organ or a blood lymphocyte or a fraction thereof.

6. The method according to claim 1, wherein said method is performed without a step of purifying and/or enriching the immune cells in the sample derived from the human.

7. The method according to claim 1, further comprising formulating said CD3+CD8+ cytotoxic T cells as identified for transplantation into a patient.

8. A method for monitoring the level of CD3+CD8+ cytotoxic T cells in a human, comprising performing the method according to claim 2, and comparing said relative amount of the CD3+CD8+ cytotoxic T cells to a sample taken earner or in parallel from the same human and/or to a control sample.

9. The method according to claim 8, further comprising treating said mammal with a chemical and/or biological substance, and measuring and/or monitoring the amount of said CD3+CD8+ cytotoxic T cells in response to said chemical and/or biological substance.

10. The method according to claim 1, wherein said human suffers from or is likely to suffer from an autoimmune disease, transplant rejection, infectious disease, cancer, and/or allergy.

11. A method for identifying CD3+CD8+ cytotoxic T cells in a sample derived from a human, wherein said method comprises:
   i) providing the sample derived from the human comprising immune cells;
   ii) determining the methylation status of at least one CpG position in a genomic region for CD8+ beta consisting of the sequence of SEQ ID NO: 5, wherein said determining the methylation status comprises the steps of:
      a) isolating genomic DNA from said sample,
      b) treating the isolated genomic DNA with bisulfite,
      c) amplifying a genomic region in the bisulfite treated genomic DNA with a primer pair of SEQ ID NOs: 8 and 9 to produce an amplicon, wherein the genomic region in the bisulfite treated genomic DNA corresponds to the genomic region consisting of SEQ ID NO: 5,
      d) performing a nucleic acid based assay on said amplicon to determine the methylation status of the CpG positions 40, 63, 95, 135, 142, 169, 194, 213, 216, 232, 245, 273, 339, 345, and 393 in the genomic region consisting of the sequence of SEQ ID NO: 5; and iii) identifying the cells as CD3⁺CD8⁺ cytotoxic T cells when the CpG positions in the genomic region are methylated less than 20%.

12. The method according to claim 11, further comprising quantifying the relative amount of said CD3⁺CD8⁺ cytotoxic T cells, said quantifying comprising detecting the methylation status of a control gene and comparing said methylation status of the control gene with the methylation status of said CpG positions in SEQ ID NOs: 5.

13. The method according to claim 11, wherein said nucleic acid based assay is performed on a DNA-chip.

14. The method according to claim 11, wherein said CD3⁺CD8⁺ cytotoxic T cells as identified are further distinguished from cell types selected from the group consisting of CD19⁺ B lymphocytes, CD15⁺ granulocytes, CD14⁺ monocytes, CD56⁺ natural killer Cells, CD3⁺CD56⁺ natural killer T-Cells, and CD3⁺CD4⁺ T helper cells by comparing the methylation status of the CpG positions in SEQ ID NOs: 5.

15. A method for monitoring the level of CD3⁺CD8⁺ cytotoxic T cells in a human, comprising performing the method according to claim 12, and comparing said relative amount of said CD3⁺CD8⁺ cytotoxic T cells to a sample taken earlier or in parallel from the same human, and/or to a control sample.

16. A method for identifying CD3⁺CD8⁺ cytotoxic T cells in a sample derived from a human, wherein said method comprises:
    i) providing the sample derived from the human comprising immune cells;
    ii) determining the methylation status of at least one CpG position in a genomic region for CD8⁺ beta consisting of the sequences of SEQ ID NO: 6, wherein said determining the methylation status comprises the steps of:
        a) isolating genomic DNA from said sample,
        b) treating the isolated genomic DNA with bisulfite,
        c) amplifying a genomic region in the bisulfite treated genomic DNA with a primer pair of SEQ ID NOs: 10 and 11 to produce an amplicon, wherein the genomic region in the bisulfite treated genomic DNA corresponds to the genomic region consisting of SEQ ID NO: 6,
        d) performing a nucleic acid based assay on said amplicon to determine the methylation status of the CpG positions 165, 196, 219, 267, 277, 307, 314, 341, and 410 in the genomic region consisting of the sequence of SEQ ID NO: 6; and
    iii) identifying the cells as CD3⁺CD8⁺ cytotoxic T cells when the CpG positions in the genomic region are less than 20% methylated.

17. The method according to claim 16, further comprising quantifying the relative amount of said CD3⁺CD8⁺ cytotoxic T cells, said quantifying comprising detecting the methylation status of a control gene and comparing said methylation status of the control gene with the methylation status of said CpG positions in SEQ ID NOs: 6.

18. The method according to claim 16, wherein said nucleic acid based assay is performed on a DNA-chip.

19. The method according to claim 16, wherein said CD3⁺CD8⁺ cytotoxic T cells as identified are further distinguished from cell types selected from the group consisting of CD19⁺ B lymphocytes, CD15⁺ granulocytes, CD14 monocytes, CD56⁺ natural killer Cells, CD3⁺CD56⁺ natural killer T-Cells, and CD3⁺CD4⁺ T helper cells by comparing the methylation status of the CpG positions in SEQ ID NOs: 6.

20. A method for monitoring the level of CD3⁺CD8⁺ cytotoxic T cells in a human, comprising performing the method according to claim 17, and comparing said relative amount of said CD3⁺CD8⁺ cytotoxic T cells to a sample taken earner or in parallel from the same human, and/or to a control sample.

* * * * *

SEQUENCE LISTING

```
<160> NUMBER OF SEQ ID NOS: 25

<210> SEQ ID NO 1
<211> LENGTH: 46586
<212> TYPE: DNA
<213> ORGANISM: Homo sapiens

<400> SEQUENCE: 1
gccaagctca atggttccct tttcccggtc tttaggattt tgggcaaatt tattcaagat      60
ggatacattt ggttccacaa gggggacact ttggggttca caaggatggg ggccacagct    120
```

```
caccagggca gaacttgagc cccctatgac ttggggggtt gatggtggca gagaagtctc    180
tgctgggtgt gtgggaggat ccctctgagc gagggaggaa tctggtaaaa gtagtaaaga    240
tccactcatc aggacctgtg cttcttgcct atgttttcag gatccatggg ttaagcagct    300
tctgtgaggt tgtagtattg ctgtagtatc catgcaggca ttgggggaca aaggttcctg    360
atataccttc cccttgaggc cttgcaaaaa gaaaaacaag agagtctcaa tacatgcacc    420
aagtcaaggt gttggttact tattaagtaa tgactgattt ttttctgtga ctcagtcgag    480
tcagatgttg tgtcaaattc aacacagaaa gagccaggca tatagcactt gataggccta    540
gggttaccac aggatccaac cacatttgat tcaggatctc aaagccagaa acctctgttt    600
ctgtttcttg tgatttcttc tcagaaagag gaaaccacac acagagaatt acctgctcag    660
ttattcccca aagttaatat catttgggaa agcgggtgag ggttttatcc ttccctcttg    720
ggcatcactg tcaattttat tgccatggtt aatcaaggtg aatttcaata gtgtctgacc    780
tgcaaattag ttttctgcca tttggaatca aggatgtacg ggtcaacagc tgcaggagac    840
ttcagagagg tccccatgct taaaaaattt ctctcaggag agtagtaagg tagggtggct    900
attgtcatca caggttggaa gacaagatgg tcacaaatgt tagagaattt attctgatgg    960
aaacttctcc tccggggtac tttataatgg acatgaagac tcaacttcag gaagatgtaa   1020
gttttcccca gttaatctac agatccagtg cattcaaaat gccaaccaga ttttgctcac   1080
aagctgatta tcaaattcat atggaagtat aaagggccaa aaatagctga ataattttgc   1140
tgaagggtaa ggggggggacc cattattcca catatcatga tttataaact ctagtaattt   1200
aaacacaaat agaacaatga aagagagtag ggggcctaga aaatacagat gtgaacatgt   1260
tggagatggc tgggcactcc tgtgggtaaa ggattcgatc attagtgctg tgacattggc   1320
ttcccatgtg ggaaaaacgt aaaacttgaa ctctatctca aaccattcac aaatgtatac   1380
tccagataga ataaatatga aaagcaaagt ttcaaaactt ttttaaaaaa tgtgttttta   1440
agacagagac atgataaggc acagaatttc ttggtcaaaa tataaaagga caagccataa   1500
aagtgtgatg ttaccattcg aacatttgtt taaagtatgc agggcaaaaa ccaatacaaa   1560
gttaaaggac aagtctcaaa ttagtagaag atatttgcag tgcataaaag caacagaaga   1620
tctttatcca taacatatca gactctcaca aagtaataag ttaaagacag cagaattaaa   1680
aatgggcaaa gtacgtgacc aagccaatat ccaaataaaa agatgccaaa cattacttga   1740
atcagtgaga tgcaaatgaa aacaaccaat atcattttat attcaaatta gcaaaatgaa   1800
caagaccaat aacatcaagc atgagggagg atatgaccaa ataactgtga tgcagtgttg   1860
atggggatgt aaattgttac aactgcagtg gagataattt gggatatcta gtaaaaatat   1920
ctattaaaaa tgaagatgct ctggccccag aacttccact tccagattca ttgctcagag   1980
aagttttgat gtataagagt gttcacagaa gcacaaacaa cagaaattgg aaaattgtaa   2040
taataattat aaactaatat ctaatagggg aatgaataaa attgtaatac attaataaaa   2100
tatgacacaa taaatgaact agatccacag gcatcaacac aggtaaatct caaaaatatg   2160
ttgaatgaaa taagcaaatt ttaaaagtgc atgtacactc tgacattatt tataaaaaat   2220
aaaagcacat gccatatatt attcattatt atgtcattgt ttatagatac ttacataata   2280
agagaatcac aagtataaaa aaagcctgga ggcagaaccc acaaatttca agatagggta   2340
tgcagtatgg aggatggaat aggggtgaag aaggggtctc aacacaaaca ttttattgct   2400
tgaaataaaa gactgaagca aatttggcaa aagttaaatt tgctaaatct gacagattta   2460
tttagcaaat ctgctaattt gctaaataaa cttgaagcta gtatgttacc ttcagtagtt   2520
```

```
ttctttatat ttggcataat tcataattca tgggaggagg taattacata ttaaaaatat    2580
atattcactg gctgggtgca gtggcttatg cctgtaatcc cagcactttg ggaggccaag    2640
atgggtagat cacctgagtt caggagttcg agaccagcct ggccaacatg atgaaaccct    2700
gtttctacta aaaatataaa aattagccgg gcgtggtggc gggcacctgt ggtcccagct    2760
actcaggagg ctgaggcagg agaattgctt gaactgggag atggaggttg ctgtgagccg    2820
agactgtacc actgcacttc agtctgggtg acagagcgag actccatctc aaaataaata    2880
aataaataaa aataaataaa taaagtatat attcataatt aacagagtaa ctgtatgtaa    2940
tgagtacctg ctgtgttcca ggcactgttt aaagtacagg catacctcat tttattgcac    3000 tttattttt tattgtgctg cacggatgtt gtattttag caaattgaaa gtttgtggca     3060
accctgcctg gagcaaatct atcaatgctg ttttcaata gcatgtgttg acttgtgcc     3120 tctggatcac cttttaataa ttcttgcaat acctcaaact ttttcattat tattgtgtct    3180
gttctggtga ctgtaatcag ttattttga tgttactatt ttaattgttt tagggcacca    3240
tgaaccatgc ccatttatga cagtgaactt gatccataaa tgttgggtgt gttctgactg    3300
ctccatgacc agccattctg tatctccttc tccttaggcc cccctatgcc ctgagccaca    3360
aaaatattaa aattaggcca attaataacc ctacaatggt ttctaagtgt tcaagggaaa    3420
ggaagaattg cgcatctctc actttaaatc aaaagctaga aatgattaag tttagtgagg    3480
aagggatgct gaaagtggag acaggctgaa agctaggtct cttgtgtcaa ataatgagcc    3540
aagttgagaa ggtagagaaa aagttcttga aggaaattaa aagtactaat ccagtgagca    3600
catgaatgat aagaaaacga aatagcctta ttgctgatat ggagagagtt ttagtggtct    3660
gggtaaatcg gaacagccac aaaattccct taagcaaaag cctaatccag agcaaagtcc    3720
caactctctt aaattttatg aaagctgaag tggtgaggaa gctgcagaag aaaagtttga    3780
agctaggaga ggttggttga ttcaagtggt ttaaggaag ataccatctc cttaacatca     3840
aaatgcaacg tgaagaagca ggtgctaata tagaaactaa taggtgctgc agcacagcag    3900
gttatccaaa agagctttct aagattattg acaaaggtgg ctacactaaa caacagattt    3960
tcaatgtaga caaaacagcc ttatattgga agaagatgct actaggtctt tcatagctag    4020
agagaagtca atgcctggct tcaaaggaca gcctgcctct cttgttaggg ctaatgcag    4080 ctggtgactt taagttgaag ccaatgctca tttaccattc taaaaaccct aagtccctta    4140
agaattatgc taagtctact ctacttatac tctgtaaatg aatagcaaa gcctggatga    4200 cagcacatct gtttagagca tggtttactg aatatttaaa gcccactgtt gagactcgct    4260
caggaaaaaa gattcctttc aaaatattac tgctcattga aaatgtgcct ggtcacccaa    4320
gagatctgat ggagatgtac aaggagatta atattgtttt tcatgactgg taaaacaaca    4380
ttgattttac atggaccaag gagtaattt gactttcaat tcttattaag aaatacattt     4440
cgtaaggcta gagctgccac agatgatgat tcctctgata gatctgggtg aaaccttctg    4500
gaaaggattc accattctag atgcaacaaa gaacatttgt gattcatggg agcaggtata    4560
aataccaaca ttaggaggag tttggaagca ggtgattcca attctcctgg atgagttgga    4620
ggagttcaag acttcagtgg aggaagtaac tgcaagtatg gtagaaatag caagagaact    4680
agagatagaa gtggagtctg aagacgtggc tgaattgttg caatcccgtg atcaaactta    4740
acacatgagg agtttattct ctctgatgag caaagaaggt ggtttcttga aatggaatct    4800
actcctggtg aagatggtgt gaacattgtt gaaatgacaa cagaagatag agaatgttac    4860
```

```
ataaacttag ttgagaaaga ggcgtcagta tttgagagga gtgactccaa tttgaatgc   4920 tgttctactg taggtaaaat gctatcaaac agcatcgcat gctacagata aatcttttgt   4980
gaaaggaaga gtcaatcaat gtggcaagat tgttgttgt cctattttac gaaattggca    5040
cagccacgcc agcctttggc aaccaccatt ctgatcagtc agcagccatt gacatcaagg   5100
caagatgccc tccatcagca aagaaattat gactcactga aagctcaggt gattttagca   5160
tgtatttggt aataaattat ttttttgatta agacgtactt ttttttttcag acataatgtc  5220 tttgtacact tagtagacta ccttataggg taaacataac ttttatgtac actgggaaac   5280
caaaaaatga atgtaactgg ctttattgtg atatttgctt tattgtggtg gtctggaact   5340
gaacctgaga tatctctgag gtttgcctat actggaattt ccaaggttag tgaaacatcc   5400
tttctgcagc ctgagtggtg agatttaggc tagtctcaaa aatataaaaa ataactagaa   5460
tataatgtaa taacagtgat cattaagata acaatgctag cagctaccat tgactgagta   5520
gtatgtgcca tgcactctgc aagcactatt ttattaatgc tcatgtgtga ggtagatatt   5580
atcattattc ttgttttata ttcaaggttc agagaggtta attcacttgc tcagagtcac   5640
acaggtagcc cagatctgct atgtgccagc cctaattact gagccatcct gtctgtccca   5700 cctttctga cccaactccc cacttctgaa ccacaggcgg tgtagctggc tttgaatata    5760
ggtgctcttt ttataggt actcttgaaa ggatcaactt tacttttttt ttttttttca     5820
aataatccaa taactttgac ttttttattag gttacactgg cattctccca agttttcat    5880 caaactcatg aagcctgctg ctccttcaat tctcaaggcg ttggagtgag gccgcctggg   5940
gtgaatcgaa gctttcggat ttatcaaatg tggtgtgatt tctaagacgc cattgagccc   6000
tgctaaagga gttgctaata tccacctcgt tctgcggtta agaaaccaac aggaaaaga    6060 acgcacaact cccagcacag tgctggcgcc tgtgaggcac tcagccgacg ggagctttgt   6120
tcttcgttgt attgtggcgg ggaagcaaca tggggccttg tcctgcggac acacttgagt   6180
taagatcaca ctggggctcc ttcaggccct gggccaagtt ggggcacagg ccgagttcgg   6240
ttgttgctgt agcctcagaa ccacccagag ttgactgaag acactcgggg gcctccataa   6300
ctgagagcag gcagaggcat tgtttttaac ccagtgtgga cccccaaatg gaacattttc   6360
cttccctagg tgaacgcctt cggaaccctc cgaaaatcgc agtttcactt ttagcaaaga   6420
gccccgctgc agcaggggaa agccccccaca aaccccgtcc tctccaaagg gaatgttccg  6480
agccccctgc ttcctccacc cttctcttcc ccctggttaa ttccttcgct ccagctcgtt   6540
ctgccttctt tctttctttg cctttttcgag gcccgctctt ctctgatttt gaagggctgg   6600
cgcaggcttg ggcacttctt tcaggttctg tattgtatgt ctgccctgtg gcttctcctt   6660
ttgcaactcc gagcaactct gtgcttggat tgcagctccc aacagtcctg ccctgacttg    6720
ccccagtcac agggcagaga tgaaccaggg actgtaccca gggttttgag ttcctgccat   6780
atttatagca tcaactctcc tttagctctt gggaaaaagg gttttaaagt gctgcaatct    6840
tctaacacaa aattatatca gtgctgaaaa tgtgttttcc acttataccc cagcaggaaa    6900
aaaaaaaaag atgatatctg tttcaggtaa gagtcatgat gacctcagaa agcaatatca    6960
gaagctatca aaatgtttat acctgtatat tcagtagtcc attctggaac atttctccag   7020
tggatgtaat cttagtcttg gcacaataga gtatgaacag agatgttaaa tgttaaaagc   7080
aatggaaatg ttcagaaata aagcaatatt taagtaaaca atgataatgc attcaatata   7140
attttaggca ttaacatgat gatgtttag aattatgaaa cctatggaaa ggttgacaag    7200
gaaaacgcag acagcatgct tgatataaac atacattcag catgattata actatgtaaa   7260
```

```
atgtaaaaaa tgttttaaa acattagaag aaaatacacc aagatgcgtt tcccttgctg      7320
ttgtttctag tggctaattt ttgcaatgtg tattactgca gttatatcac ctttacaaat      7380
ggaaagctta aaataactc acttccttc ccagagagca atgttcagtg caaagccaca       7440
ctccactcca gggatggcct tcagcactgg actttttggg agccagaatc aagcagtatg      7500
tgtcacttct tatctcatgt tgttggtgcc acttactcat atgttgtctc atcattctgc      7560
agttgtttaa tgtgtttata tcttctcta caaccatttt ttaaaagcta ttttaaaat       7620 tgtggcaaaa tgtatgcata acataaattt accatttag tcatttctaa gtatacactc      7680
cactggcatt aagtatattt atatttttgt gcaatcatta ccaccatgca tccacagaac      7740
tttttcatct tcctaaacta aaactctgta cccactaagc accaactccc cattcccct      7800 ccccagttc caggtaaccg ctatgatatt ttcagtttct ctgacgaatt cagagacacc      7860
actcttggta cctcctgcaa gtagaatcat actgtattta ccttttgca caatcatttt      7920 ttaaaactta aaaaaattt ttaattaatt ttttgagac agtctcactc tgtcacccag       7980
gctggttggt gtttgcagtg gcacgatcat ggctcactgt agccttcacc tcgtgggctc      8040
aagtgatctt cacatctcag actcccgagt atttgggact acaggcaccc accacggtgc      8100
ccggctaatt ttttaatttt ttgtggagat gaggtcttac tatgttgccc aggctggtct      8160
caaactccta ggcccaaggg atcctcctac ttcagccttt caaagtgctg agattacaaa      8220
gcgagccaca agcctcggcc tgcacaatca ttataaaaag ctctctgagg ataaggacca      8280
aggccctgat ttgttttcat tgtaaacata atgttcattt gctcattgat ttgatattga      8340
ctgtgcaccc acacgtgtgc tgggcactgt tcgaggcagg gtttaagaaa cgctcaagaa      8400
gcacatgtgg tctctcaagg ggacggtgta gtggacagag ataacaaaga aaaacacaga      8460
gaagaaagaa tgacggagag tgagaagtgc tgtaagtgca gtgacagaca ccgccccagg      8520
gcctcctgga caggctgcat gtttgtagga tgatggggag tggtcctgga aagactgag       8580 gaggagccct gggggtccca ggcagagaga ggaggggcac agagctggag gacggaaggg      8640
cctttgtaca gcatgtgtgt gtgtgtgtgt atgctggggg acacgcaggg agatggcagg      8700
cctcagcact ggggagagct ggagtgcatt ctagatgcag cagggagctg gagcagggac      8760
cctcttctcc ctgcctggcc tgagagcagg aaggaggcc ctgggctgtg gctgattgca       8820
gtcaacactg aggaacaagt gccaatgctt catgcagggc acaacctctg ccacacttt       8880 acctatgtga ccttctgggc caggtactgt gaggtgcttc atttctcaga tagcaaggct      8940
gaggctcaga tcaatgctgc tttgcacaca gctggaagtg gccaaatcag cccgaaaccc      9000
ccatttttgt ctgcatcttt gtgcagggct gggtggctgt gtgtgcaatg tctgttgtgc      9060
tggacatgca acaggaaagc aattgttacc tctaattttt aggaggccaa agggcaagaa      9120
gccacgtgct ccaggccaaa gagcagctaa gggaatgaag agtaaatctg tgattgaatg      9180
aatgagcaga tgaaaagaga aaagcctcc ccctgcacaa acctgcaacc cattcccttc       9240
ctggggtcct gtggggaggg ggcttttcat cagtgccctg ggtcagggaa gagagaggga      9300
ggccttgtgg tggagggaag gggaggagag ctcaccatca gaggtggaaa gaaggttcta      9360
gtccctccag agcacactca gggatgcttt cttgtgcttc tgtcccaagg ccttgtctcg      9420
accttgctta ctataaacac agtgctacat cctgcttttc ctttacttca ttgcataaac      9480
cttccctgaa tcgcttccag aatctttaga accaccgttt ttaaggtttg aatacttgta      9540
taccaagtaa atgaccacag cttattgaaa ctcctcttta tagtcaacca cttaggttgt      9600
```

| | | | | | |
|---|---|---|---|---|---|
| tctattgtta | tttctagaac | acataactaa | tgccaataaa | taatgatgat | ggcacagatt | 9660 |
| agtatttcct | gaggatggat | ctcttgcgtg | ggttccaaag | ctctaagcaa | tttatatggg | 9720 |
| ccctggagtt | tcctccacag | ctcctaaggc | agctctggca | catgaggagg | ctgggaaaag | 9780 |
| agcaggggtg | atgggtgcat | ctgccttggt | aagtgaactt | gttggttctg | tcccacgcag | 9840 |
| cttgggtgtc | ggtgtggggg | gtgtgctgct | ggggttggag | aggggccgcc | ctacataacg | 9900 |
| tccccacata | aaaggggcag | gtgtgcaggt | ggtcccaggg | atggcggcag | ctctgtctga | 9960 |
| ctcccccta | ctgggggct | atgggggctg | tgggagtgga | gggtgaggat | caccgtcctc | 10020 |
| caggatcccc | caaccctcc | ttggccattc | cctttgactt | ccttgggaaa | gagtccaggc | 10080 |
| ttcagaggat | tctttgctca | tttcaatctg | accccatttg | aatccccaag | ggtcgcagta | 10140 |
| aaccccaggc | acacaaagac | agaggcttgt | ggctggcttg | cggttgctgt | gatcacgatg | 10200 |
| gaatcagaca | acggctgccc | tggcaggcag | cacccaggca | cctctcaggt | gggaaaagac | 10260 |
| tgagccaggt | gaatgtccca | gagctccagc | cagctcaggc | tcctatgggt | gataactgca | 10320 |
| ctagacacct | ctccgaagaa | gccaacagaa | actgcatgca | gcggcaacat | gagcaaagat | 10380 |
| aagtgttggg | acccgttctt | cgctgccacc | tccaagtctg | aacagcaggc | tctaaggggg | 10440 |
| gcatgggagc | ccctcagaaa | gggccactgc | ccatgcctca | cctcctgccc | gccactccac | 10500 |
| tctttattgt | cctacctgac | tgtaacaggc | tgcatgctca | acatggtgtc | agctgcccca | 10560 |
| aagagcacca | ggaggagaca | ggggtgccat | tcggacatga | acaggagctc | ctacctgaat | 10620 |
| gtgcagacct | ccgccactgg | agctctcggg | gggaaaacat | ccatgacagc | ctccctgagc | 10680 |
| cttgaaacat | ttgcagacca | agcaggctca | ggtgcccgtg | tttgcaggcg | gttttttaga | 10740 |
| acgtatcatt | tgtcttatat | tgatgtaccc | ttcaaagccc | gggaggaagt | gtggtcttgt | 10800 |
| ggggagctct | gtgcaggcaa | catgagagtc | tgtattgtct | tcctagctct | gccccggttg | 10860 |
| tcagaggagt | ccatctgggc | cacaggggtg | aggagccgtc | acccctgcct | tttgtttagc | 10920 |
| cggtgacacc | tccccagttg | tgtggcgggt | gatgcagcaa | taatgcccac | gagctcctct | 10980 |
| caacaatcaa | acaaaacag | agagccactc | taaaacagtg | gctttcttgc | aaatggaata | 11040 |
| tgctgagaat | ctgtgacatg | tgcaggtcgg | taagtgagaa | ggaaacagga | accaccaatc | 11100 |
| gattctgaca | atgtagaaag | cagtggaggt | ttggggccag | gagaacaaaa | gacctatggg | 11160 |
| agaggcggtg | acccaggaag | ggtggccatg | gacttgggtg | catcacctga | gccctgtcac | 11220 |
| ttggaaagaa | ccctaacgac | catcttaatc | ctgcctgtat | agatacctta | ctgtgccgct | 11280 |
| gctgggtgtg | aagcgtggct | actaaaaatg | ttcacttcat | ttttaagaag | tagaacaggt | 11340 |
| tcaaggttat | tcctgtagac | gacagtgtcg | ctctcgccca | agtacactgt | gggaggcttc | 11400 |
| cttagcagga | tcgaaagggg | tggaattaca | gtgggcactg | gaattggctg | tggttcacac | 11460 |
| atgtagacat | gactgtgaat | tcttgtttt | ttttttttt | tgagacgggg | tctcactctg | 11520 |
| tcacccaggc | tggagtgcag | tggcatgatc | tcggctcact | gcaacctctg | cctctcgggt | 11580 |
| tcaagcgatt | ctcctgcttc | agtctcctga | gtagctggaa | ttataggcac | ctgccaccac | 11640 |
| acccagcaat | ttttgtattt | ttagtagaga | gagggtttca | ccatgttggc | caggctggtc | 11700 |
| tccaactcct | gacctcaggt | gatccactcg | cctcggcctc | ccagagtgtg | aggattacag | 11760 |
| gcatgagcca | ctgtgcctgg | ctgactgtgg | attttgtggc | agcaaagagt | tcatcttggt | 11820 |
| tcatcagcta | agactgtgct | caagtgtaag | ccactgagta | gacttgttta | tgagtgattc | 11880 |
| ttggaagctt | gcaaggactt | cttttgagtt | aaaaaaaaaa | aaaccttctg | gtagagttaa | 11940 |
| acatgaattg | gcttgccctg | agagttcggg | ttttatgtca | cgagaggtag | ttaaatgtgg | 12000 |

```
gctgggggcc tggtgtggtg gctaatgcct gtaatcccaa cacattggta gactgaggtg    12060
ggtggattgc ttgagcccag attgagacca gcctggccaa catggtgaaa ccccatctcc    12120
acaaaagtta aaaaaattag ccaggcatgg tggcatgtgc ctgtggtccc agctactcac    12180
gagctaagtg ggaagatcac tggagcccag gaggcagaga ttgcagtgag ccgagagggc    12240
accactgcac tccagcctgg gtcacagagc aagaccctat ctcaaaaaaa aaaaaaaaaa    12300
tgtggggtag acaaatatgg ggcagggttg ctgtaaaggg tgttcacgtt ttattttgga    12360
agctgaataa tgtagacttt aaattgtttt tgcaacatag agatctacag ctctggacta    12420
atggatcaga ttttgctagt tgcaaagatt tttgaatttt aattgcagtt tgctgctgtt    12480
tcacccacaa caaaagtaga ggaagaactc atagcttata tgcagtgatc atgaactctg    12540
gggctttgta gatgagacta ggaaaacttg tgcaggacct gaagttgaac tgccttggct    12600
cttgttccca tgtgctgggg gatggggcaa ggacatctca ccaggtatca gtgggtggtc    12660
tacactattt gagtaaagtc ctatccttat agtgttgctt tcctgcctgg tgacttgact    12720
gagtttaggc ttagcgacct gcttataaaa tggcaagagt acgtacttgc ataagcggtt    12780
aattgacata atgcaggtaa atggaacagt accaaacgct taataacaaa tgcttaataa    12840
atgaagatgg tggctggcaa gtgggggcga atgtcaataa acaacatgta aaaatatgga    12900
tcatctggtc actttaaact tttagtgaga tcaaatgtgg gcaaaatttc tctacaaata    12960 actgaattg tgtgtgtgtg tgtgtgtgtg tgtgtgtgtg cgtgtctgga cccacagaga     13020 agttttaat gtagatatat aaagtagata atctcattta tattttggaa aatttttaatt    13080 tttaaaatt tttgttattt gatgatgatg atttgtttcc ccttcagagg aggttttcca    13140
gctctaggag atgctgttga caatctctct tctgaagtta agggggcctt tgagtggctc    13200
tggccactga gaagtgaaac cctgggagca gctagagatg gccagcctat gatattcaca    13260
gccaatgtgt taagtgtgaa gttctgtgca agtaggtttt aaataggtac agcctaaaat    13320
acataatttt cttattatca aaatcatgtg ccttttttaag gaaaaatcta agaaacacag    13380
aaaagcaaag agaagaggaa aataaagtat tcatatgggc ctacctccaa agatgcaacc    13440
agcaacctct actttattat cttctggatt ccttactct cttaaaaatg gggtcctact      13500
ctagttgttc taataactct tcatcacttt ttaaaaacag taatttgttt cttgtcatta    13560
tatcttctcc atatatacat acacactctt ttttttttttc aaaatggaga ttgcattgtt   13620
gttttgcctg gctgtcagtg taatactcag atggaagtac tgcacatgca taaacaagac    13680
gataaagatc acttgtaatc tgccccacac caacccctgt cacatttgga gttaccattt    13740
tggcatatgc tctttacttt ttttttttt tttttttttg agacggagtc ttgctctgtt     13800
gcccaggctg gagtgcagtg gtgtgatctt agctcactgc aacctccgcc tcctgggttt    13860
aagcgatttc ccccgcctta gcctcagcct cctgagtagc tgggactaca ggtgcatgcc    13920
accatgcccg gctaattttt tgcattttag tagagacagg gtttcaccac attggcaagg    13980
atggtcttga tctcctgacc tcgtgatctg cctgtctcag cctctcaaag tgctggaatt    14040
acaggcgtga gccaccgcgc ctggctggca tatgatcttt ctgaatattt tgtttactgt    14100
ggattcctaa ttagggaaaa aggagtcagg ctgggggag tcaggcgggt gggagcaagg    14160
gaaaataaaa agagaaagca gataagcaac aagtctgcct ttctttatgg tccaggacac    14220
acagccctcc tgagcaagta actctcacca gacacgtgca agttagctca ctgcaacctt    14280
ggcgttatta atactacaca aagccctctt caacagatag cataaacgct accctgtaaa    14340
```

```
atcaccagca agcctttgtc tccttgcagt cagtttctct ctgctgcctg cctattgtcc   14400
ctctggcaat gtattttcta ataaatcttc tgccttcttt tacctgcaac tgtttcggta   14460
aatcttttac ctccacacca ccggctgtca ttcccccatg acatttaaca catgtttctt   14520
acacacagat aatttctctc ctcttctgcc gagagctggg ttcatagaat atctaacgtt   14580
tgataatctg cttttaaat ttaataatgc attgtgaaca tctttccact tattaaacat   14640
tcttgcacag cattatttta atgtcattta ttaccttgca tggatgtatt ctcatttatt   14700
tcactggtag atatgtagtt tttagcatgt ttttctttt tttgagacaa ggtctcgctc   14760
tgtcacctag gctggagtgc agtggtacga tcctggcaca ctgcagcctc agcctcctgg   14820
gctcaagtga tcctcccacc tcagcctcct aaagtgctgg gattacaggc atgagccaca   14880
ggtcccagcc agtttttagc atgttttcaa tatgcttaca atactctgat gcatgtcttt   14940
gccactaata attcttgtgg ggccaggcat ggtggctcac acctgtaatc acagcacttt   15000
ggcgagtcag ttgaggccag cagttcgaga ccagcctagc caacgtggcg aaaccctatc   15060
tctactaaaa atacaaaatt tagccaggtg tggtagcata tgcctgtaat cccagctact   15120
tgggaggctg aggcatgaga attgcttgaa cctggcaggc agaagttgca gtgagccaag   15180
atcgtgccac tgcactccag cctagggac agagtgagac tctgtctcca aaaaaaaaaa   15240
attattatta ttattgtgca taaccaataa tatcatgaat attttcgtga tatattcata   15300
gaagtgaaat tgctggttca aaaaaaaata cacaaatttg aggctctaga tatgtattgc   15360
caaattgccc ctcagaatgg tgggaccagc ctggactccc agcagtggat tatgaatggg   15420
cccgtttatc agcactctta tctatctgaa atgctatatt atggtacaat ctggtaaaat   15480
ccatttaaaa atgcattcct tttgtttatt attttaataa ttccaattta tattagaaac   15540
cagtttgcat ttaattttat tagattttgt tattaattaa attactaaat ttctggtttc   15600
tgtcctttta agaaacgtta tttatttaaa tcatttagaa tttctttttgg tgtcagatat   15660 gaagggctaa aactccattt tttccaaata tttaaccaat tgtctcggca ctctttatta   15720
taatctatta ttttttgttg tttgttttg agacggagtc ttgctgtgtt gtccaggctg   15780
gagtgcagtg gtgcgatctt ggctcactgc aacctccacc tcttgggttc aagagattct   15840
cctgcctcag acttccaatc gctgggatta taggcacctg ccatcatgcc cggctaattt   15900
ttgtgttttt gtagaaacgg gtttcaccat attggccagg ctggtcttga actcctgacc   15960
tcaggttatc tgcctgcctc gacctcccga aatgctagga ttacaggcat gagccaccat   16020
gcctggcttc tataatctat tcttcccca tgtatgtgac tgctacattt gtcatgtaat   16080
ccacatgttc aaatggagtc tattcatgca tcacttcagt gattgaaatc agcaatttaa   16140
aattgatcag taaatatcta gcagctgata atcccatgag gagagagaaa cttcttttgc   16200
ctttgagaaa gaaatgttt tccttctgat tctaaaagaa taggtgagtt gctttcctct   16260
atctctgcaa ttttccctc tgctgggacc cacagatggg gaaatgaga cctctgatga   16320 ggcagcagaa acccagaagc cagaacaccg ctaaccagta atgaagctgt gggatcactg   16380
aagctcccct gccccaggga gacacgggtg gtcaaagtag aaactgaaga tcagcctcag   16440
agactcccag actgaggagt cagcctaatt ttctgataag aaattaaaga ctaggggctg   16500
ggggagtgag agaagtatta ttctcaaact tttaggaaaa aaacaaaat gaaacaaaac   16560 agtgaaaaga atgatcagga agtcagtaac ttcattgtgc ctgtgcttac aatgccatct   16620
ttttaactgt aggaattggc cattgtaata acaaatgcca ctgctgtaag gaaggtatca   16680
gtgagtggga aagggtctta attgtgctgt ctcatctgac gagcttgagt gttcacacca   16740
```

```
cgcagccaca gccagagcag cacactctat ctggggtggt gaattgtaat tttaggcaaa    16800
tatcagagga gaaaataaat taccttgagt gattataaaa ctaaaaatag taagagaagg    16860
ataggtgcag tggctcacgc ctgtaatccc agcactttgg gaggctgagg agggtggatc    16920
acctgaggtt aggagttcaa gaccagcctg gccaacatgg tgaaacctcg tctctactaa    16980
aaatacaaaa ttagccaggc atggtggtgt gtgcctgtaa tcccagctac tcaagaggct    17040
gaggcgggag aatcgcatga acccgggagg cagaggcttc agtgagccaa gatcatgcca    17100
ctgtactcca gcctgggtga cagagtgaga ctcgatctca aaaaattaaa aaaaaaaaa     17160 gagatatcat atcaaataag aggaagggca cggtcacatg aggtttttat gcagcaccaa    17220
ataacctgct cgagtgggga ataaatgccg acacttcagg ttgtgagcca ctatgatacc    17280 cactttcct gcccccaccc tcccttctgt tgttggtttg cccccaatt tactgctccc      17340 tgtgtgggtt gagctttgta agctgcccca atccttttt gggaattaga caatgcaagg     17400
ataaataaaa acattgattc ttaggagctt ttcaatgtat tataaaattg aattttaaca    17460
gacaggttaa taaaaataaa aagaggaata cttttgtttt gatctcttgt tatttaaatg    17520
aaatttatcc cttttccagg ggaaagtttt tgttttgaca ctcatggtca gcactggtct    17580
cctctcctct cctctcctct cctcccctct cctccccctcc cctctcctcc cctccccctcc  17640 cctcccctct tctctcctct cctcttctct ctctccctct ttccctcca cccttcctct    17700 tgctgcagcc tcctcacagg gtcataggca caggaacaca gctacagaca tgaagatgct    17760
ttcctgtgtt acaaaaaagg atagtttaaa taattccctg catcctgctt ttcctcctta    17820
atagtacact ctggcagtgt tgccaagtta atctgtcttt ttttttttt ttttgagatg     17880 gagtctcact ctgttgccca ggctggagtg cagtggtgtg atcttggctc actgcaacct    17940
ctgcctccta ggttcaagtg attctctgcc tcagcctccc gagtagctgg gattacatgc    18000
ccggctaatt tttgtatttt tagtagagac agaattttgc catgttggcc aggctggtct    18060
caagctcctg acctcaggtg atggcccacc ttggcctccc gaagtactga aattacaggt    18120
gtgaggcacc gcacccggcc ctctcctctc ctctcctccc ctcccctccg ctctcctccc    18180
ctcccctccg ctctcctccc ctcccgtccg ctctcctccc ctccccctctc tctccctccc   18240 tttctctctc acccttttccc ctccgcccat ttctccctct ttttccctcc ctccctccct   18300
cccttccttc cttccttcct tccttttctt gggggggcagt ggggacagag ccttgctctg   18360
ttgccctggc tggagtgcag tggcttgctg taacctcaaa cttctggact aaagtgaccc    18420
tcttgcctca gccttcctag tagccgggac tataggcatc caccaccatg cctggctaaa    18480
ttttgtattt ttaatagaga tggggtttca ccatcttgac caggctggtc tcaaactcct    18540
gacctcgtga tccgcccacc tcagcctccc aaagtgctgg ggttacaggg gtgagccacc    18600
gtgcccggcc aaatcattct ttttaagtca ttcttttgat ggctacacga tattttggg     18660 tatagataga cagcaactta ttaaatgatt ccctattgat tatctgggg ttgtttccca     18720 ttttatttt gcccaaacaa tatggataga atcatctttg tatatttatt ctgatgcaat    18780
gatgcttcta ctttcccggg gacccattcc caggagtgct gagtgacagt ccctaattca    18840
tattaaacac tactagatgg tgcccacctg ttttccacaa agctgtagcg ctcgcttatt    18900
ccagcatcag caacacctgt gtgcccttgg ccacaagctt tccagcagtg agcagcatca    18960
ctgttttaca ttttttactca gtgacatttg tatgcaaatg acagattatt atttttctgg   19020
aaaatgtatg cttaaccatg ccagggtcat aactcatgct atgaaaaaga ttttggtgta    19080
```

```
gaggtcatgg cagaagaaat gagaacgtgt gaatcagctt tcttctctta cacacacaca    19140
cacacacaca aaagtcttaa ctgagcttgg atattaaaag cagtgtgggg gagagggtgg    19200
ggaggtttgg agttaccatc aggagcgtct gaccaggctc aaacgtggga tagctgtcca    19260
ttgaacagcc ctgtatgtca caatgactag gaaaaattta taagacagac gttccaggcc    19320
gggcacagtg gctcacgcct gaaatctcag cactttggga ggccaaggca ggaggatcat    19380
gaggtcagga gttcgagacc agcctgacca acatggtgaa accccgtctc tactaaaaaa    19440
tacaaaaatt agctgggcat gatggcgcgc acctggaatc ccagctactt gggaggctga    19500
ggcaggagaa tcgcttgaac ccgggaggcg gaggttgcag tgagccaaga tcgtgccact    19560
gcactccagc ctgggcaaca gagcaaaact ctgtctcaaa aaaaaaaaaa aaaaaaaaa    19620 aagacaagcg ttccctgca cccgcccac caaatcgcct gccacacaca gaagcacgca    19680
caggcgcact ctgaaattac acagataaaa ggccgacagt attactccct ctcccactga    19740
taagctcctt tctgtgctgg gtggggctgg cggactttct gatggaggaa gatggaactg    19800
ccagagtgag cactggctct ggtctgagcc actgtgagcc tttcttctct cctccttcat    19860
cccctacacc acaagataga ccacccaaca tggctttctg agtttctagg gagctgggct    19920
ttgagcaggg cccacaaaag gacttcaacc aaagcctgct tgtcttgtgg aagccaccct    19980
acctccctgt ttccaaacca gaagcatcag tgtggctgca gggtaggtac tcggatagag    20040
gcagggacga cccaaactcc atcttctgcc ctggcccagc tagagccttc gtgatccgaa    20100
ggcaggcccg ccttttgtgc tgatcacgtt tactgttgct ctcccctccc tatgtccccc    20160
aaacttggct gaggctgagg taagggtgga ggggtgggag tcatggcctc cctttttgcct    20220 ggtctggtct tgcccagaca gcaggcctag cccagcaggc agcttcaggc ttgcaggatg    20280
ctgaaggggt gctggggagg ggtgtgtggg gaagaggagc ctccacccct ccaccaacac    20340
cacctcacat cttccccctcg taactttgcc ctcacccaac cgcagagacc tccacaaaat    20400
ctgtaagagg ctgtgaacaa cactcccagc caaacataac tttttttgaga aggcaatcca    20460 tgccctctgc ttgtgttggt atcacccggg tctttctctg gtctgtccgg ggctggcatg    20520
aggctgcagc cagtgaggca ctgaggccac tcactcttgg agccacgcaa gtgccagcct    20580
tgagcctgtg tccccccggt catgagaatg aaagcccgtg gggttaggga catcttctga    20640
gccaaatctt tagtgtctga aacacatgcc tgattgagat ctgagttgtt gaacttggtt    20700
ctctaagggg attgtccatt gtacttggca gagtaaacat cccgagtggt cctcacagcc    20760
ttgaggagca cagaaaggtg ggtgggtgga tgggtggggg agccagcagg ggaggtgctg    20820
ggaggggcag tggagaggga gggctgtgct cccagcttgt gggggcctaa ggactttcta    20880
tctgagcctt ttgctttgtt cattcattca tttcagttct ggcctcaggc ttaggagtga    20940
tttgtacagg tggcaggaaa gagccagagg accccacag gcctcggccc tgggctacta    21000
gggagggaac tgaggcctag aggctgtaag caagactgcg agccctgggg gccaactat    21060 gtccatcctg gccatgccgc acccctagtc ccagcacagg gctggctggg cacacagaag    21120 tttcccccaaa tagatatatt tgaaccagca tcaagaaact taagggattg ggcatggtgg    21180
ctcatgcctg taatcccaac actttgagag gctaaggtgg gaggatcgct tgagctcagg    21240
agtttgagac cagcctgggc aacatagcga gacctcatct ctaccaaaaa taaaaaaaaa    21300
ttagctgggc atgctggtgc gcacctgtag tcccagctac ttgcttgagt cagggaggtc    21360
aaggctgcag tgagccatga tggcgccact gcacactagc ctgggcaaca gagcactgta    21420
cacacacacg cacaccccca aggaagagga gaattgagtg cagagttgtg ggtattagtt    21480
```

```
cagtcataaa tggggacagg agtggaaatg gtctacaatt aaaaatgcat gaaaaggcca   21540
ggtgctgtgg ctcattcctg taatcccagg actttgggag gccgagatgg atggattgct   21600
tgagcccagg agttcaagac cagcctgggt gacatgggga aaccccatct ctaccagaaa   21660
tataaaaaat tagccaggtg tggtagtgca tgcccatagt cccagaaact caggaggctg   21720
aggtgcaagg atcgcttgag cctgggagac agagcctgca gtgagctata agtgcgccac   21780
tacactccac cctgggtgac agagcaacac cctgtctcaa acaacaacaa aattatgtag   21840
aagaatggac atggtttcct ttcaaattta gaagtctaag caaagctctt aaaagggtac   21900
tcgcttgtga aaggcagtaa actaatggga aaagcaggat ccaggagagc caacagtact   21960
gtggaggttg taagtgtctt tttcagcgcc tctgctttca gctttacagg aatcacacgt   22020
gtcgtgcata tttctgtgaa tctcaaaccg acgcagggct gggggaatatg gtttccttct   22080 gtttgagtta tgtaactggg aggactccag gaaccagtga ctcacagttc cccgggagtg   22140
tcagtgacgc atcgaaggag gtttcccaag aagcgacaga ggaaatatct tttggaaggc   22200
ctctgaagac agggctcttt ctgtcttttcc ctttgactgg gtggtagatt cggatcagct   22260
ttgcagccca cgcggggtcg gggatcactt tctgaaaaca agttgcccac ttcctacagg   22320
tagagacaca agctgcgggg cggggtggg gatgagtaag gatgaaaggg aggggtggt   22380 gtaggacccc ccttcttctt ttgaacaggc cggggtgggc tccacacctg caggctactt   22440
cccactgaaa ggaagggggc gggggagg gggaacacca gtgctgctcc cagacccatt   22500
aaggtccaca gaaaacaca gaaaaggaag tactatagat gttctccttc agggcagaga   22560
acccaggctc acctaaggtt gctggagtgc agcccacccc tgccacgagc ccagcccat   22620 gtgaacttcc agacaagtaa atgcaattgc aaatgtagct cgcccaaagt ctacagctgg   22680
taaagaccca ggctgtgctg tctggccacc tcggacctgc ctcaccgtga tttccatggt   22740
tcagattttt ttaatttatg aataaatctt tcgtttgtgg atattttat tgattccaat   22800 ttcttattat aacaatggcc agaggttctt ttttttccaaa ctttttaattg ctttttcccc   22860 aactacaaaa gtaatacatg atgtaaaaat tcacacaagg aactgtacaa agcagaagtg   22920
gaaattccgc agagtaactg caattaacag ctgaaagtaa atccttacag acctttttcct   22980 gtacatatac aaacaaatat acccggaggc cttgatttat tattagagaa aaaagatcaa   23040
atctgcagaa caatattaga agatgtaatt ttctatattc tctattttat gtattatatt   23100 ctcaagatttt caatttatg ttttaaaaaa tatgggaaga aaaaaaaaca agaaactttt   23160
tagaaaaaat ttattttga gacaaggtct gtctgtgttg cccaggctgg agtgcagtgg   23220
cgtgatcaca gctcactgca gtctgaaact cctggggtca ggagatcctc ccacctcatc   23280
ctccctaata gctgggacta caggcaagca ccaccatgcc cagaaaaaaa tttaaaaatt   23340
ttttgtagag tcgaggtctt gctatgttgc ctaggctgct ctcaaactcc tgagctcaag   23400
tgatcattct gtgtgggcct cccaaagtac tgggattaca ggcgtgagct gtaatccat   23460 gtgcttgctg aagaaacttc caaataccaa ttttacacat ttctacaatg ttctgtactt   23520
ggattttaaa aagtctcttt cttgaagtat aatttacatc tatatccata gctctaaagt   23580
caacatatct gagtgtacag cttgatgact tttactaatg aaacacactc ataaagtga   23640 ttcccagatt gagaagcaga aatgctcacc ttcaaacctc atgctccctc ctaatgacca   23700
ccactggacc aagggtaact gtatcctaac ttctaacaac atatatttgt tttgcttgtt   23760
ttcttttgtg cttgaatttt aacagtgact acatattgtg ccatatattg tattaagaat   23820
```

```
aatctataca gatgttttaa aaatatatgc atttgtcata accatcattt gatatcagca   23880
tatatggatc tagctcattc cttagcagcc gcctaaaccc ccttattaga ctgtgtctga   23940
atttatctga ccagtcccct ttgatggaca tttggattat ttcccatttt tagctagtaa   24000
gcaacactag aaggaacaat ctgatgcgta tttctttgtg catgccactt tttgatgtat   24060
ttctttcaga taaatgccaa caagtggaat tgctagtcaa aagatagctg gatggagttt   24120
gggggggcata tttcatcata atggcccctat agagtgtagt agcagctcag ctccttcttc   24180
aaacaaaggt caggtgctgg gtgcagacct tctcaccgca gcccccacca ttggcagccc   24240
agcctgctcc agctccctgg gcagccgag ctgagcccgc tcggcaggt gcctgctgca   24300
cagaaaactg acagaggagc gcaaaccacc cctgccccca gcccaacccc atgagaactt   24360
gtgaacaagt acatgcaatt gcaaagacag cagcagggag acggtcaaat ttcaaagcct   24420
gcagtgggac aagaggcctt gtggcctgtt cttacttccg ctgtgcactg ggtgtgagcc   24480
ttcaaggagg gcagaccatg tgcactgcag gccttaatct cttatttgtt tgtgatgggc   24540
cgggtgaggg gcccacctga aacacgaacc ctagaggagt ctggtccagc tgaccccaat   24600
tctttcaccc ctcccctcag ccttggaagg cagcctgtcc cttgtcctca gagctgatgg   24660
gcagagcttt tgtttctttt gaacacctct tgctgaggca ggagtctagg gtctgggggc   24720
agggaatcta aggccaattc gtgctgaatc aaggagaaac atctatgtcc gggggcaggg   24780
aatctgaggc caatttgtgc tgacttctca aagctggatc aaatggaaaa cacctgggtc   24840
tgggggcagg gcatctaagg ccaattcgtg ctgaatgaag gagaaacacc tacgtctggg   24900
ggcagggaat ctgaggccaa tttgtgctga cttctcaaag ctggagcaaa cggaaaacac   24960
ctgggtctgg gggcagggca tctaaggcca attaacatac accaaaagga aaaccccat    25020
ctccccacac tgagtaacca aggatcaaag gctactctcc ctacaaccct ccccccttcca   25080
ctgcatctca gatggaaagg gagacggccc tggattgacc acagaccaag cacgggccat   25140
cccttcatcc gcatagggcg tcaattcacc tcagcctttc attagccatg gaccaaatcc   25200
ttcacccaga taaggggtag ccaacaggta cctcaaaagg ggtacttaaa acccagaaaa   25260
ctttgcaatt gggcccatgg gctatctgct tagggtccac tcctaccatg tggagtgctt   25320
tctcacttca ataaattctt ccttttgctg cttttattcc tttattactt tgtatgtttt   25380
gttcagttct ttgttcaaaa tgccaaggac ctggacaact tacactcaag gccctccttc   25440
cggtaacact gcatctatgc cttctaact ccacccacca cacctcattc tgctgcggcc    25500
gcaccccaga tgccaggaga aggtcacact gcccttccc cagagtcgtc tttcctttcc    25560
tgtttttttt gtaacatttc ttacattctg tggttgtcac aggtaactga acataacctg   25620
atttgtcaat gtccttcttt gagctggcca ggaaaagcag gtgaggctgg attctccctg   25680
gacctggacg tggtgcttct gttaatgcag cctcaggttg cagtgtttta tggtgcaata   25740
gctcctaggc tgctaaagct caggtagggg cggctaagat gggtctcagg cacttttca    25800
aacccaggca cgaggtcctg ctcttcactc tccactcctg ctcagcactt tctccttgct   25860
ttttccttct ccaactgtca aggctaagaa tcaataagaa aatgaagaga catgtgacag   25920
aaccctcat gcctcctacc ttctgtttgg tgcctgactt gaagccaggg atccctgcgg    25980
ttcaacccgc ggtagaaatg aacacgtgct agttcagctt gggagtgggc tgggagaggg   26040
gcctgaggca cctgcagcct ggctctgggt gccctgggcg cttcctagcc tctctaggac   26100
tctccacacc tacaacgtcg ggcaaatgag gatctcaggt gcaaaggag gatgtacaaa    26160
ttttctcctt ctggtttctg ttccacggag cactgatgtc tttgctgtag atgggctttc   26220
```

```
gcacgtttat gtcacaggag ccgtttgtta tctttaacct gggactttat ttgtacaact   26280
aagacatttg tataaaacaa acagaaaatg aaagaagcat taagccatgg gagagtagaa   26340
atgggagctg agaaacttaa gagtagaaat gggagctgag aagatgaagt gaactcctat   26400
cctcaaaccc gcaagttccc ggccccaaag gaagccctca gagactgata tgccttctgg   26460
gaactggaca gcccctctca gcaagcctca ttcccaacct gcacctggcc tctctgcgag   26520
gaaggtcagc cccagcctgg gaagaccaag agggagccag cccagcatca ccccatgaaa   26580
gacccaggac ccaatgttac tgccctacca gggcaaagca acctgcaaag atggtggcta   26640
aatggccacc actaaaggtc ccagttcagg gaaagcacag gagccggaag cggtggcatg   26700
ggcagcattt cttactcagt cctccagcac actctgtgaa gtgccctggg ggcaatgaaa   26760
ccttctccct agtattcccg atgacccacg aacaagttgc tcccatgcac atcacacaca   26820
gaaaggcctt gcagcagtga aaagcaggca gcttcagcag ccattgaact ctccagggtt   26880
gaatgtgtcc cttctctcat ttttccacat cgtgctcgtt actgaccgat gtcttttgt    26940 agcaggacac caaaaccgta ttctctgctc atttgtaaaa tctgaaaaca acagcaagtt   27000
gtgaaaccac ttattttcag gcaaacgata ttgaatttcc tgtaacgagg acaaatggca   27060
aatgagaatg cagagttcta ctccaagtag cctggggccg agagttttt gttagtatgt    27120 ttctagggcc catcttagtc attaaaaaga ttgttaaggc taaaaaacaa aacaaaacaa   27180
aactgcagct caaagaacgg tagctttgaa ttgggttact tcctgtagta cctctaagat   27240
aatctaagag aatcacaaat ttatatcaag gggccagaag aaattagcct gcagatggga   27300
tgattttcta aggacagtta gaggctgggg aacaactacc tcaaatcgca actcagatct   27360
gtgagcacca caggctattt cctccatgcc tggatcatga gagcaaaacc agaggtggtt   27420
ttcaagcttt tttgaagcca caaacccttt tgttcaaatg acatgttaca ggtaagtgta   27480
aacccagaca atagaagaga gtacgtctgt tcaaaatgaa gagagtgagg aggtctcagg   27540 gtcccccac gaccacccag agcccttcc ctgcctcaag ctgatcctgg gcttgcaaaa      27600
gcatgaggtc ctgcatccag cctccccaaa actggcatca gatcactggg gagcaagtta   27660 aaaatgaaggg gtggggacag acccagacca cagttagtac cagagaggga cttactttcc   27720
atgaaaggtc atcatgggag acattttgaa aggaactttc tttttttttt tgagacagag   27780
tttcactctt gttgcccagg ctgcagcgga atggtgtgat ctctgctcat tgcaacctct   27840
gcctccgggg ttcaagtgat tctcttacct cagcctctcg agtagctggg attacatagg   27900
cgcctgccac cacgtccagt taattttttg tattttagt agagatgggg tttcaccatg     27960
ttggccaggc tggtctcaaa ctcctgacct caggcgatct acctgccttg gcctcccaa    28020 agtgctggga ttacaggctt gagccactgc acccggcctt gaatgaaact ttctagaggt   28080
ctggcctgag acagctacac tcaagttatt atctcttggg taggggcag cttctaaatc    28140 caacacacaa ggtgaaaatt gtacacaatt aaaatatcat tgaaaattgc cataaaatc    28200 cagcaggcat gtttaagcca ctctcgatat aaatataatg tgtacaacaa tgcagagcat   28260 atagtaaatat gaatttatat ggctatttac aattttagag tattcaaaaa tacatttgt   28320 ttgtccattg ctgcacttgc agagtggaat ttactgaagt gacttgagct tgtgctctga   28380
ctccggggtc ctggggccac atgctttaag gataatcccc cagtgagtcc tcacactgac   28440
tgtgagattg gcactgttag ctcatttaac agacgagaaa tccgagactt ggagacgtga   28500
agtgacttgc tggctgtcac atggtgattg gcagacggga ttcaaaccca gccctgtctc   28560
```

```
cacctaaagc tggagctttt gagcaggaga acctgttgcc ctcttcaatt tagagttgtg    28620
tacttttgct cccccaaaca tttctgtata gaggggttg ttctaaggat caaatgtaat      28680
taactggata ggcagatgtg aaacagtctc tgttgtgagg aacaaaaatc aaatgcagga    28740
atgctgccct ggcccaggat ggcttccaac agcctcatga aagacccagg acctaatgtc    28800
actgccctac cagggcaaag caacttgcaa aggtggtgac taaatggcca ccactaaagg    28860
tcccagccca gcccagggta agtacaggct ctttctcagc ttagtgggcc caagagtgc     28920 tatgtgactc tgtcaactcc tgggacccag atggggtcga gggcagcagg tgggacaaag    28980
gcagctccta gggaaggaaa gcaatggctg gtagaagagg ctggtcttca aatccgattc    29040
cagtagtctc tccactgatc tgtcaaatga gggtgataac cccttatctc acacagtacc    29100
aaggggatga ataataggt gggatgaaat aacggatggg atgagtttgg gatactctgc     29160
ggtattctgt gcatgcaaag cctgattgct ctcctcagga gagctaagaa tgttcttgaa    29220
atacatttaa cttactggtc aggtttttgt ttgtttaggt tatctcttag gttcctgaac    29280
tctatcaccc catctatttta tacagtctgt aattttttt tttagatgga gtctcactct     29340
gttgcccagg ctggagtgca gtggtaccat catagctcac tgcagccttg aactcctggg    29400
ctcaagtgat cctcctgctt cagcctcccg agtagctgtg actacaggtg tgcactacta    29460
tgcccggccg agtctatgat ctttggaaga tgaggtctga ctttggctcc tcgctgcagt    29520
tagaggctgc aagctgcagc aggggctgag gaacccaagg ccacacccag gttatacact    29580
tactgtttca tgaaacgaag ccgggctctc ctccgccggc ctggaagagg aaagcaaggg    29640
cgccagtcag tgtgggctgt gggtcactgc gctgagcccc agaggccaag gaggattgtc    29700
acaggggcag ctgacaccctc agcccacctc cctggtccca daccctggcc caaacacttt   29760
acacatttta atccccttaa tgctcactga aaacctgagt tggatactac ttttaagatc    29820
tccattttat atgtgggaaa ctgagacaca gagtgagtga attactggat aacatgccca    29880
aagtcatgca gctagtaagt gggaaagcca gaattcaaac tcaattagtc agctgcagag    29940
tctgtgtcct taaacacacc tgcttgccct tcacagcagg tcagacatga aaggtcccag    30000
agacaggcag tctcaggcta gggcaattgc attcagaggg tgagcgagat ttcccactgg    30060
gagttaggaa gaaaataaaa gcatgtctat tgacatttgt atttcagcct ttattacttt    30120 tgatttcat ttattttttt aggaatgggg tcttattatg ttgtctaggc tagacttgaa      30180
ctcctgggct caagtgatcc tccctcctca gcctctcgag tacgggcact tgccactaca    30240
cccaacttac ttttcatttt gaagcacatt taataacata cataaaatat taaataagta    30300
aatacagcca actgctgcat ttactttata atattcaatt agctgtattc gcttatttaa    30360
tattttatgc atgttattaa atgtgtttca aaatatttta ccaatgagtt ccttccttga    30420
tcgagagagt ttgcaaacca ctgaaattta tgggtttctt agaatggggt acatgggccc    30480
ctctgtgggg aacaattgta ggcaaaagta tgctcctggg tgcatttctg tggggagagg    30540
tccgttattt tcatcgtatg ttcaaagggg tctgtgacct acaaaagtta agagccactg    30600
atctagttca tgcccttgct gtccacctg cccatttcat agatgcgcag agagggaag     30660 gggcttgctc gaggtggcac aggtgagcag aagaaccggg gtagagtctg ggctctgggc    30720
tctagggcag ccatgcaggc ctcccctctg gctccccgtc tttcttgtga acccagtgct    30780
gtgcagagct ggggtgggg gccatagaag gagacagtcc cgtctctggg gtggctggga    30840
gcagcagtca tttctgtttc ccacagcctc atcaatatcg gtgtcgtgga gaggatttct    30900
agcttctagg aacacaacac aaaccccata ggcaaacttt tctggacact gggctttggt    30960
```

```
ctcaactgct cacgtgagtt cccactcact gacacgtgcc gggtgccagg catttggggt  31020
aggaatttac aaacagcaac tctgggaggt agctaatgtc ctaccccat ctgaggcagc  31080 cgaggctcag agagaccggg gcactggatc aggaaacagc cacgttgcac tcaaacccag  31140
gtttgcctga ctccagggac agggtagtct ttggttttgg ctgcgtagcc ccaggccaag  31200
aactacctct ggaaataccg taggttctct gaggcaaatt cccaccaggc tgccatctgc  31260
tctgctcccc tagagaagaa aatatcccag ggacacttca aacagcaaac agggacaccc  31320
aacaacccaa gaggagacaa ctcacagcac aggtggatgg ccactcccag ggaaaccagc  31380
agaaccagga cgccagccac cagcaggcca agggtgatgg ggctacaaag tgggcctgga  31440
aaacacacat gtgacatgtg ttcaacacgg aacattttc tgcatgagac acgcagaaaa  31500
atacaaggag cgaaaaattc aactggaagc cccacctccc agagaatacc accatttgta  31560
tttcgatgta atgtattttt cctcaagtat tttttttttt tttttttttt tttttttgag  31620
acagagtctt gctctgtcac ccaggccgga gtgcagtggt gcattctcag cttactgcaa  31680
cttccgcctc ctgggttcaa gggattctcg ttcttagcct cccgagtagc tgggactaca  31740
ggcatgtgcc accatgcctg gctaattttt gtatctttag tagagagagg gttttatcat  31800
gttggccagg ctggtctcaa actcctggcc tcaagcaatc cgcccacctt ggcctcccaa  31860
agtgctggga ttacaggcct gagccaccat gtccggccat cgtctagtct ttgtaagcac  31920
tttaaacatt attgaaatca ttttattata aaatttcatg tcccacattc aaattttaa  31980 gaagtagaca attttcatgc ctggtaatga gtcttttact atttattttt aaaactttta  32040
atttcacaag aaatagctga atatatttc attgtaagac atttaaatat aggattagag  32100
tgctccctga catctttgct ccttcacaga attaatcacc actgataatt tagtaacttt  32160
ctctttccat gcctatgtaa tttttatata tacatatagg gtttgttcgt ttgtttgttt  32220
gttttgacac agagtctcgc tctgtcacac acagtctcgc tctgtcgccc aggctggagt  32280
gcagtggcgc aatcttggct cactgcaacc tccgccttct gggttcaagc gattctcctg  32340
cctcagcctc tcaagtagct gggattacag gcgtccgccg tcatgcctgg ctaattttg  32400 tatttttagt agagacgggg tttcaccacg ttggccagga tggtctcaat ctcctggcct  32460
caagtgatcc acccgcctca gcctcccaaa gtgctgggat tacaggtgtg agctaccgca  32520
actggcctta aatacatata gttttaaaaa atatatagag tggattatac tgtacaaatt  32580 gttctttttgt acctttattt tttcaacgtg ccttttttcc ttcacttagt caatgtgttc  32640
tttcttccag cagagtaaca tctgacagca tggatgtacc atgagttact tgtcatcagt  32700
gggccttttg attgtttcct gtgttttact tttacaaata actctgcaga aaacaacctg  32760
tatatttcct tacaaaggca ccttcctgag gtaaatactg agaacgggaa ctactaaacc  32820
acagactttg cccatttaa attgtgacag atgctgtcaa atgcctccct aaaaggcggc  32880
actgacttcc gtccccaccc accaatagtg caccttgctg acccttgata tcatcaaaat  32940
gttttagttt ttgccagtca agtggggaaa aatgttattt cacttaaatt ccctaatttc  33000
ttataagctt tggcctattt tcatatattg gaacttgta tgattttct tctacgagtt  33060 gactatctgt tcctttgtcc attttgtgtg ctatttaaac agcagacttt acactatcaa  33120
tgtcccaaat cctcctctga caccttcag gcccctgtgg ctggtcccett gagtagctga  33180 ggggcagagc agggcccatg ggtgaaaggg caaggctgca gatttgggct tgaggttcgg  33240
aaaattggaa agcattgtgg atgtcaagga agagagagaa tttttactga atacatatgt  33300
```

```
gctaagtaca tactaaatgc aaactcccat cttgtgagga agaaaggtat tggtattttt  33360
aaattattta tttatttatt tatttattta tttttgagac ggagttttgc tgttgttgcc  33420
caggctggag tgcaatggca agatctggac tcaccgcaac ctctgcctcc tgggttcaag  33480
cgattctcct ttctcagcct ccttagtagc tgggattaca ggcatctgtc accacacctg  33540
gctgattttt gtgtttttag tagagatggg ttttcaccat gttggccagg ctggtctcga  33600
gctcctgacc ttatgtgatc cacctgcctt ggcctcccaa agtgctggga ttacaggtgt  33660
gagccaccgt gcctggcttg ccattatttt tacctctcat ttcacagttc aaaaaacaaa  33720
aacaacaaga ttcaaagagg ttaaattata taaccaaggt cacccagcta ctaaaaggca  33780
ggaccagggt gtggacacag atcctccgag ttccaagccc ctgtgggtcc cacctcagct  33840
gcatgagggc atgagaggta caggagggaa gggagtgggc tgctacatgg gtggcagccc  33900
actgtcacta gaggggaaca agccaaggct ggatggctgg ggtgtggaga ggagattcat  33960
acacggacag ggaggctgga tgaggggccc ctctgagatg ctgagggcat ctgctgggct  34020
ccctctcacc tcctatttgt tctcccaacc tggatgaacc tcaaaacatg gtgctaagtg  34080
aaagaagcca agcatgaaag accccatggt gtgtgattcc acttctatga gatgccctgg  34140
ggaggcaaat ctgcagaggt agacggtaga ttagtggctg ccaggggctg gaacagaga  34200 tgagctgtga acaagcacag ggaatcttac tggggtgatg gaaaccttct aaaactagat  34260
tacggtaacg gtcgcccaac ttggtaaatt tacccaaaat cattgaattt gtatgcttaa  34320
aatgggtgaa ctttgcggta tgcaaattat atctcaacta aggtgttttt ttttttttt   34380 tttgagacag ggtcttgctc tgtcgcccag gctggagtgc aatggcgtga tctcggctca  34440
ccacaacctc cgcctcctgg gttcaagcga ttctccttcc tcagcctcct aagtcgttgg  34500
gattacaggt gcccaccaca atgcccagct aattttttgta ttttttagtgg agacggggtt  34560 tcgccatgtt gatcaggctg gtctcgaact cctgacctca ggttatccac cagctttggc  34620
ctcccaaagt gctgggatta taggtgtgag ccaccatgcc tagctcaact aagtttttaa  34680
aaactgtaat ggaggtgggt gcaggtcaca gggatgtaca gggcggcacg ctccttcct  34740 gaggagaggt catggttaag accactgtgg aggccagcaa tgtagctaca ggtctcctct  34800
ggagcactgt ctcccatcca aaatttgact ctccgggaaa agctgctgct gcaaataacg  34860
tgcttgggta aggggccatt tgccagagcc acaccaacga cacccccagc ccagccttcc  34920
tcatcttacc ggggcctcag ggtctcctga gctctggatc tgcactctgc tcctgagtct  34980
atggtttaga aatggtcccc cagcacctaa gggtgttgtc ttaggaacag acctaagcct  35040
caaggggcag tgccttctca gtgaccccat gggtttcatt catgataaca ggctttgagg  35100
tctgtgtgga cgccccacaa gctctgagtg cctggtgtat aatagcatct catttagccc  35160
tgcatccccc attttacaga caaggaaact gaggttcata gaggctgaat cacctattca  35220
gtgtctcata gtacaggcag tggtagacag agattcagac ctaggcctga ctgacttgcc  35280
actaggctac actgacccag ggccactctc ctcagtgtaa cctccaccta ctttccccac  35340
acccatcccc agccttactc cactaggtca ccttcacaca catccgggtt attcttaata  35400
acctattaat gtttggtttg catttttgccc tgggaattta ctgagggtta gtacaagaaa  35460
tgatgcaaga ggccaggcgt agtggctcac gcctgtaatc ccagcacttt gggaggccaa  35520
ggcaggtgga tcacctgaag tcaggagctc aagaccagct tggccaacat ggtgaaaccc  35580
tgcctctact aaaaatataa aaattagcca agcgtggtgg tgggcacctg taatcccagc  35640
tactctggag gctgaggcag gagaatcact tgaacctggg aggcggaggt tgcaatgagc  35700
```

```
tgagatcacg ccactgcact ccagcctggg caacacagtg agactccatt tcaaaaaaaa    35760
aaaaaaagaa agaaagaaaa gaaattatgc aagaaatctg aagacctttg tttttgccat    35820
catttataaa agtatgactg agtttgccgt cattcagctg tccttacatg aagatgaatg    35880
ggcagattgc ttctcgaatt tagtgctagg atgaaggttt cttcttttgg tggcaggttg    35940 tttcttttcta tcactggggt tggggtgcca tacaacttgg ggtcttccct ttgtttaaac    36000
tgatgttgcc gggttctcca cagccgtagc acacaaccgg ttcttgcgcc ctcatcttag    36060
tggctctatt gtatttgcct tttatatcct ttttatggta gtctgcctga aatcgtttag    36120
gtgaaggggt cagggcatgg gactttataa aataaggtta ctcttaagct ccttaagact    36180
ttactcttct gtacattggt tctgattttc ttttactgt gacctcatgt gacggcagct    36240
tcccaccctg gtctcccaga tcctattcag tgccgtcctc aataatttct ggtgcttaaa    36300
atatttaaga caaagcaaac tgagcagtgc gaggcagtgc tccaggggct gcttgtggtt    36360
tgttttctgg gtagcagcag atggcacttt ctgtttgtca ccagtgactt ttgctgggct    36420
gaggtcagta tttttccaga aacacgtttg ggctgatggg tttaaggaaa acgtgtgcat    36480
gggcatgtgt gtctgtgtgt gtgtgtatgt ggcatacact ccagctgagg tgtctggtgt    36540
agcatagaga agcaaatgtg ttcatttgca aacaaacatg tattcatgaa ctagcacata    36600
ctgtgtatta ggtcctctgt taggtattaa aactggaaac tttttttga gacagggtct    36660 ggctctatca cccaggctgg agtgcagtgg caggatctca gctcacttca atctccacct    36720
cccaggctca aggcatccac ctcagcctcc tgagtagctg ggactacagg catgtgccac    36780
cacgcccagc taattttttt acattttcgt agagacagag tttcaccgtg ttgcccaggc    36840
tggtctctaa ctcctgagct caaggcgatc cacccatctg ggcctcccaa agtgctggga    36900
ttacaggtgt gagccaccac atctggccaa aactggaaaa gtttaaagtg ctggtccttt    36960
gagtggattt tttgtttgtt aacagcttta ttgagttata atttacgtat aaagtcccct    37020
tgtttaaagt gtacaatgtc atggttttta gtgtattcat ggagttgtgc aaccattatc    37080
ataatgtaat ttcagaacat ttaaattccc ctaaaaagaa accttatacc cattaggaat    37140
cactccccat ttctttccca gccccccagc cttaggcagc aaccaatcta cattctgtct    37200
ctacagagga tcatatgctg gatattccat aatcatggaa tcatatagta tatggatttt    37260
tgtgactggc tccttcatt ttattcttta ttatggccaa acaatattcc acgataataa    37320
ataagccaca ttttgttaat cagctcatta gctggtggat gtttgggtag tttctgcttt    37380
tggctagtat gaataatgaa gctatggaca tttgtgtgca ggggtgtggg tggagatctc    37440
ctccattaag ctttgtccag taacaattta tgagtctgtc tcccacgaga ctgtgagttg    37500
ctggcacact cagcatcctt tctgacccta gcttaggccg gggagatagg ctctagagtt    37560
gacacttgga aagtgcctgg ggaaggaagg aggggaggga gggagggcaa gggatgtct    37620 gccttgtttc tgagggtgca gagggatagg gaactcaccc ttctgggtct ctggcctggg    37680
taaccggcac actctcttct tgagggtgga cttcttggtg ggctgggcag tggtgggaag    37740
gaaatcaact acagaaagaa agcaagacac atatcttagc caagtgaaca ccacgtggac    37800
tcaaagacaa aactttgtct tatggcgggt gcggtggctc atgcctggaa tcccaacact    37860
tccggaggcc aaggcaggag atcatttgag ctcaggaggt tgagaccagc ctgggcaaca    37920
tggtgaaacc ccctctctac aaaaaatataa aagtttagcc aggcgtggtg gcatatgcct    37980
acagtcccag ctacccagga ggctgaggtg agaggatcac ctgagcttgg gaagtcaagg    38040
```

```
ctgaagtgag ccatgatcat gcaactgcac tctggcctgg acgacagagc aagaccctgt   38100
ctcaagagca aataaatgaa caaatgaaca aaatttgtct tacatccaag tactgaagtc   38160
cttatgactg ttccccaggc tgctacaggg cttgaaggtc acagagcaat agaatgtttg   38220
atctgctttc tgaattctca gatgttggga aaggggtgag ggcctagaga tggggttcag   38280
cttggtgtcc tggagagagg aaggctctgg agccacacag aactgagcag agcctacacc   38340
tctgatttat ttattttat ttatttattt atttatttat tttttgagac aaagtctcgc   38400
tctgtagccc aggctggagg gcagtggcac gatctcggct cactgcaacc tttgcctccc   38460
aggttcaagc aattatcctg cctcagcctc cagagtagct gggattacag gcacgtacca   38520
ctgcattcgt cgtgccactg cattcgtcgt gccactgcat tcgtctaatt ttttgtattt   38580
ttagtagaga cggggtttca ccatgttggc caggctggtc ttgaactcct gatctcaggt   38640
aatccactca cctcggcctc caaaagtgct agtattacag gtacgagcca ccgcacccgg   38700
ccgacctaca cccctgatta accgctgtgt gacttgggac aagtcatagc atttttctgt   38760
gccttgattt cctatctgc tgaaataatg ataactgcca cctccttctt gggattatct   38820
gagaatgaaa gggacagtgt gtccaaaaaa agtttcagta gatgtggctc cacctggctg   38880
aagaccttga gccccagggc tggatcgccc agcctttggc acaacgagcc cctccgccca   38940
actcggcatt ccctaagcac atggaggaag ctcatggaag aggggtgc cctttctgc   39000 atgtagagta ccacacaggt gtcatatttg gggattggtt ttccttctca gatggcccta   39060
aaatatatat ataataccag agctaaggga agttcagtct caaactttaa tttcaaaggt   39120
gaacgccaga gatgagggga gctggcccct gcagccccaa gtggtgagtg ctgtgttggg   39180
accccaaacc cctgtcctga ctcctggatg ggtcacccct ctccttcatt tttacccagt   39240 gaccctgct gaagtgttgg gaggggcagt gggccagcac ccagagcaaa ggaagacagc   39300
tgtggctctg atgcctactg gggatgaagg gggcactgct ggccacagag tccaaccctt   39360
gcctttgtgg gttaaggaaa cagatctctc tgcactgatt ttctccaaaa tggtaggaga   39420
gggagtaagg agacaccatg aacctaaact ctagagtcag ggggacagaa aaaaaaaaa   39480 gaaaagaaaa gaaatattaa ggctgggcgc ggtgactcac gcctgtaatc ccagcacttt   39540
gggaggccga ggcaggcaga tcacctgagg tcaggagtcc aagaccagcc tggccaacat   39600
ggcaaaaccc tgtgcctact aaaaatacaa aaattagttg ggcgtggtgg cacgtgcctg   39660
taatcccagc tactcaggag gctgaggcag cagagtcgtt tgaacctgtg aggcagaggt   39720
tgcagtcagc caagatcctg ccactaaact ccagcctggg tgacagtgac tccgtctcaa   39780
aaaaaaaaaa ggttttgggg ggttgtaagg gggaacaggc aggggaagcc cacagatcag   39840
tcattttggg gctggcatct tctatataaa agtagacatt ttaaccctc acctctctga   39900 gcctcctctg gaaagcggag agaacacgat ctgtttgtct gcttcaagac attgatggga   39960
agaagcaact aggatgaaag tgcactaagc tccaaccatg tgtggggagc agtgctgagc   40020
ctttcagcat aagtttactg gacacaacaa cttttggggc aggcactgtt gtccccattt   40080
tatccaggag gaagcctagg ctcagagagc tgaaataatg tgtccaaagt tagacagcca   40140
ctggctgcag agccagtatc tgcaccaaaa gaccttgatt ctagaacctg tgcttctcgt   40200
tctgccacac tacctcacgt gcaaagattt tctgacaaaa gttgaacact ttaggtccac   40260
ccaaggccct gggtcatcat agtgctgagg gcaactattg taagaggaaa ctgtcatcag   40320
cagggtcgga gagcgtgcaa cgagcctggc cctctcctgg gagtgttgcc tccttcaatc   40380
ctcatggccc tagaagtagt tctgtttgac ttattttcta cccgaggaag cagggacgtc   40440
```

```
tttcagatgg tcagtggtga gcccagaggg gagccaactc tttgggccct cagtgccttg    40500
gctgggcacc gccgcctggg tctagtggga gactcaggtt gggggactgt tctgttttaa    40560
attcttcttg cctagagcca ggtcccctg gattcctcct gagcacccag tttaatctct     40620
ccctctctgt tcttaaaagg aataaaactt cgagcccatg atatacttaa gggcctgaaa    40680
aaggccctgt ctttccccaa acactttctc aaccatccca gctttgtcct ctaaaaggcc    40740
tttcttgggt gagaaggtgg ggttcggctc cgaagaaggt ctggttgcaa gccctgggga    40800
gaagcaggtt tggctgcaag ccagagctgg agagaggcat tgacattcct atagtgctgg    40860
gaggggtttg gggtttggaa acacggaagt caggagtgag tgcggttggg atggaggcgg    40920
tgggaagctc tggaaactag ctgtgtttat tgtaccctcc accttctcag actctgaaat    40980
ctcatgagtg gaaggtgtg gggcttacag agacaaaaac aataagctaa agccaaaccc     41040
caaaccccaa accccaaact cccaaagtcc attttcaat acgaaaatca gtggaccccc      41100
acgtgaaggg atgcctcagc ttcttgcctg caatacaccc tcccaggcta gcaagaggtg    41160
gcggggcatc actttggttt gtgtcttcct aattgtgctg ctgtcccag ctgcccctgc      41220 acttcctcac gctgagtggt ctaatttctg ggtcccttg tggcttttag tgccctcaag      41280
tgagcaggaa gcagggcagt gggagccctg gaggggttg gctccagcct tgggccaagc     41340
tggaggtggg gctagagcca gagccaggct gtgagagtta ccacccataa ctaaatgcct    41400
tctgtccaat atgccacagg tgctgctgag cacatgaaat gtggccagtc tgaatcgaga    41460
tgagccatat gttttatgta aaatgctcat cgaacactta gtatgaaaaa tgaatgtaaa    41520
atatttcagc aatacttttt atattgatta catgttgaga tgaaaatata gttaataaat    41580
tgagttaaat ataacattat ttaaattaat tttacttgct tcttttgct tttttaaaca      41640 agactttaaa aatttagaat ttcatctgtg gcttgaaatg tgcgtctgct ggacttgctg    41700
acttaagtca gaggtctgca gcttctctgg gattaagtgg gtcatggagg ccatcagcac    41760
ccccgtgtga cacagaagag aacactgagg cccaggggag aaagcatggc aagtttgcaa    41820
gcagagctgg gcctggctca gtctccttac taacttcgac tcaggtatga attcgagctg    41880
taggccctca cagagaacat aagggcacct gcccctagaa atgccctcac tgggtatatc    41940
agggcagtga gggcctcctt tccctgtgtg cacactctgg ggatttctaa caccactata   42000
aggccaaggg gctcagccca atccagccgt agctttgaat gtccctgatg tggcctgaag    42060
gacagcactg ccctgtcccc ataagaagaa taatgcctgg ccaggcatgg tggctcacgc    42120
ctgtaatcct agcgctttgg gaggctaagg tgggtggatc acttgaggtc aggagttcaa    42180
gacccacctg gccaacatgg tgaaatctcg tctccactaa aaatacaaaa aattagccag    42240
gtgtggtggc tcatgcctgt aatcccagct actcgggaag ctgaggcagg agaatcactt    42300
gaacccggga agcagaggct gcagtgagcc aagatcgcac cactgcaccc cagcctgggc    42360
aacacagtga ggctctgtct caaaaaaaat aataataata aataaataaa aagagaagc     42420 acaatgctca tctctgactc tggcccgtct cttctagttt catcttattc ccacctaaag    42480
tggttaggta atagacctac cttccagggt ggttggcagc attaagcaag ctaactatgt    42540
aaacacttgg aggggcttgg cctgggtaag tctccacatg ttctttctgt tactattagc    42600
agcagtgcca ttagtcacgg ctgcagagtg gggcacactg aagcctggtg gtcccagtgc    42660
ctggcacgtg cctggcacac aatcggtgct cactgatagc attgagcctg cttcttaccc    42720
acactcagct gagttccctt cccgaaggtc agctcggggc tcccgacgat catgcagaag    42780
```

```
tagatgccac tgtcttccgg cttcacgctt gtgagattga aatgaaccg gcttgcatcc    42840
cgaaacacag ctatcttctc ctgttccacc tcttcaccgt ggatagtccc ttttgcggaa    42900
tcccagaggg ccaggaactc gtggtgactg tcactgctcg gtgcctggcg ctgtctcagc    42960
cagtagatgc gcatgttact gagggagatt ttagcctcgc aggacagcat caccatcttg    43020
ttggtttgca cctttatgta tgcaggggtc tgctggagga ctgagttgcc atggagaact    43080
aggaaaagcc aagaacagag acatcacaca ttttcctagc cacagctgtg ggaccttgca    43140
gtcacactga gtcaagtgtc aaaggaaaag ccatggaagg acctgcccag ttactgggtc    43200
cagggagtgt gttgagcgca gctgttggct cctggactca gagttcacat accccacctc    43260
ccaggagatc atctggaagg gaggtgtttg ctaagttcag ctttacaaag gtacagggga    43320
gagagctgcc atttgtttat tgtgtactta tatgcctggc ccttgcataa aggaactcaa    43380
tcaagcctca aactggcttt ggaattttt aaaagacatg gggtcttgtt atgttgccca     43440
ggttggagtg gagtggctac tcacaggcac tatcatagta cacttcagcc ttgacctcct    43500
gggctcaatc tatcttccca cctcagcctc ccaagtagct gagagtatag gcatgtacca    43560
ccacaaaagg atagatccag gattttaat cctcattaca cagatgagga aactgaggca     43620
tgaagttact tgttcaaagt cccacttaca gtatgtaagt ggcctaggag tcaaactcaa    43680
ggatttgaag tctgaagcca aagctggttg cctttcacct cccctggctg ccactggatg    43740
tacagcccctt cggtaggctc caaactgccg aaggagaccc aggacaggct gggagaggag   43800
cccagaatca cagcagagca tgtggctggt ctgtccgttg ctggacagac cctggtaggt    43860
acaattacag cccatgaccc ccgagcccag caactgatgg gtcactggat ccctattccc    43920
cagtggaagg acagacacca cagaagcagg gctgggagtt catcttagac tctgacgaga    43980
agcacccggc aagcaggggc ttattcatga ggagctagag caggactcac agacctggcc    44040
ctgaacccag cctctggccg tgccagctgt gagacctcag gccagtcacc gagcctctgt    44100
cttcttatga acgaggaca gcttgggct gttgtcctgc ctgcctctga gggttggaaa       44160
taaatgaaat gctgtccaaa aaagcacact gtaaactgta tggccatgta cacaggtaaa    44220
tactgtccct gtgtctcata tcacagggtt gttactggag gtaaattaaa tctcaaggag    44280
aaggatcaga acaggttcca tacacaccaa ggctgcacag cttccaacaa acacaatctg    44340
acctggtgag ccccttcattt tggctgtgga gcaaagggag acattgcagg ccagggcaga   44400
gatgcaggag ttgggaggca cagagaggac acagacctgg gtaggcagag ggggccagag    44460
ggcatgtgtg tgtgcccaag aggagccagc ttactgagca cctcatgttt aaaatcctgc    44520
ctgcacttgc agctcaggct ccgtggcccc ataatggcct tctccaacac tgatgaaatg    44580
aacttcgact ttttgacttc gctcctggac cactcttagc tttcgctcgc atcaagaatg    44640
aaatgatggg gccgggtgtg gtggctcatg tttgtaatca cagcactttg ggagatcgag    44700
gcaggaggat cacttgggct caggatatcg agaccagcct gggcaacata gtgagacctt    44760
gtctctacta agaatacaaa aattatccag gcatgatggc gcgtgcctct aatcccagct    44820
actagggagg ctgaggcagg agaatcgctt gaacccggga ggcggagatt gcagtgagcc    44880
aagattcgcg cactgcactc cagcctgggc gacagagcaa gactccatct tggaaaagaa    44940
aaaattatta aaaaataaaa ataaaaataa aaacaagaag gaaatgatgc ctggggcaca    45000
agtggctgct ggacttcctc ttgtttcccc aaacaccaca ctgcggttcc agcagagcag    45060
aggttttttcc ttgctttggg tcactcactt cttgggggag ttaataagaa ccaataatgc   45120
cagtttattg agctgtgcct ggcatggcgc atacattatc tcatttgatc ctcaccaaat    45180
```

```
cctgtggggg agatactgtt ttgcacctac tttacccatg aggaaagaga gactcaggag    45240
ggttaaagat gtgctcaagg tcacacagtg atccagatta aacccagct tgtgggaccc     45300 caaaacctga ctttgaacca ctgaattgaa gaaacctgca atcctctccc tgatggtggt    45360
tatgtgctca cgagcacaca gtggggctgc aagtacacag gtgcccgaag cccttccggg    45420
aaaacccaga agcgactcct gtaagagcaa ggcctgggct gtgagtgtgc atttcctctc    45480
ctggctgaga cacaccccgg ctcttcccgg ggcccacttg cttttttgtcc cctaggaact    45540 gaatactccg ggctgtggcc aaggccctgc tgtgtgctgg acatggagcc aggcctcact    45600
gcatgttccc ctcggtaacc caggaattcc attctcagag ggacctgatg tttctagatc    45660
catcagtaat gactttagtg ctctgaacgg cctgggctgt ttctatttat gatgttgcac    45720
tcactgggcc agaaccccg gcgggcaggc cttgtcaccc cctggcaaga tgaccagctt     45780
tgggcttttt gggcacgaga gcaaatcgac cagtttgggt agttttccgg gtgtgtggag    45840
gcttcttcca aaaggcagtc tggctgggct tattcagaag acaatccag atgcccatc      45900 caactccaac aacccaacct ccaggctgct tcctagggag ccacgctacc catgacaccc    45960
aacaccagcg acatcaggga gaacgggagc cagagggatc accctgccct agccctccga    46020
gaactgagaa cgcccgatgt ttgtctgatt gtactacaaa cacttccccg gaagtaataa    46080
aaatgtgtcc acaggaccca tggcctggcc aaccttcctc cgagcacatc ctgcggggac    46140
cctgggcagg gacctgtttc cttcccctgg tgacctccag cgaccctctc tttccttccc    46200
tcactcgctc ccctttttcac tgcctcccct tctcctgcgt ccaggctttt gaggggaggt    46260
ggcctcagtc caggggctct ccggtcccc ggggtaatgc gatatggggg tattttattt      46320
ccacccttag ggaccgtgcc tgccaagctg cctcccgggc gccccgccac cgcgggctcg    46380
acgctgcacc ctgccaggac cagggccagg acagccactt atcacctccc cgctcaggcc    46440
ccgggagcgc agaccttgg gtagcccgcg cgccgccgcc ttacctgtca gctgcgcggc      46500
caagaggagc cacagccgcg gccgcatcgt ggcgcgcccg ggacacctgg ccccgggggc    46560
tcggcggaga cagtcgcggc tggggt                                          46586
```

<210> SEQ ID NO 2
<211> LENGTH: 23791
<212> TYPE: DNA
<213> ORGANISM: Homo sapiens
<400> SEQUENCE: 2

```
cggatgctgt ttacccatta aagaggatgc tacaaatgtt tattcattaa agccactcat      60
aacagcatag tacaacccta tttaaaaaag aaagacatat tttacatgta tgtgtagaaa     120
ataatcagga agaatgtaca ccatattaac aggagattat tcctaaggtg aagaattatg     180
agtggttctt atttccttat ctacttaagt ttttttctctc caatgggcag gcattgcttg    240
taccatacct taagcaagga agtgcatgtt tgggacagca gtttgggctc tcagcctcct    300
taagagagtc aggtctgcct catccctgta tctgctagtt gagcagaggc cagggctgtg    360
tgaggggctc tccaacaatt gtctttacaa agtataaaaa gtcatcagtg atcccaggaa    420
catgtttgta tctcaaattc agagattcaa gagggcctta gtttaacctc actgatgctc    480
aaattctatt tgtaaagggg tagcctgtcc tctttcatgg gccctctgc aatgcaaggg      540 ctgggagagc aattccgcct ccacataggg gtttcacaga gattttcttt agagatagag    600
ggattcattt tccagggtta agctcaccac ttcatttat tttaggtcta tacaatttta      660
```

```
ggcttgatta taaaaaaaaa aagtctgata ttgtttacat tatagaactc tgccaaaggc      720
agttctcttc tttaattcat tacctcctcg aggctctggg cacagtatcc caggtatcaa      780
gaagtacttg ttcccttgcc gttggagact caagcacctc accctgagac aggggcctcg      840
gaaagaaaga cctgaatggt gtggaggaaa gagccctgag ctgggagaca aggtccctcc      900
agctactgct ccaaccctga cttgctgtgt gcctttgatc aagctgtctc tgggctttag      960 cctcccccctt tgtaaaacgg gcggggaaga ggttgagatg gcatgggtgc ctccagctct     1020
ctcagcatga ttctgagaac tctgcgggta gctctggcct gccccttttcc acgccctacc    1080 gcgatgtgcg cacaacagta ttgtgaccct tgtggtgtac tgtagatttt acctagtttt     1140
gtttcccgtc aaacacataa agaaaaagta atctttccca ccccgccccc actaaaataa     1200
taatcatgag aatgaataca cagggaggaa gactggaaaa aatgaaaggg aaggacttgc     1260
tccctcaaaa ggaaggatct cagtttgaag taatgtagtg gctgttgcac agggttagac     1320
gtatctcgcc gaaaggctgg gcttgtctcc cgatttgacc acaggcctga aagagaggaa     1380
agcgaccatc attgtagcca gaaccccgcc agtgcagcat ccatccagcc acgtccagcc     1440
tcccaatccc ccagcctttg aaaggtctga aacctgttc ctggggcacc agcatgggac      1500
tgggtgaatg acgtcagcac agcacccgtg ctaaatgcct tacttgcacc atctcatgta     1560
atcctcacag cagccttaag ggtgggcact gagattgaga agttaaactt gcccaaggtc     1620
acacatctag gaggtggctg agccaggatc taaaccgagt tagtctagct tcctggagcc     1680
cctgtcaagg tctccacaga ggtgtgagag tgagactgat aaccaaagtc attagctgac     1740
ctgattctca gccccggagg atgacaggga gagaggagga tgtgagcaaa tcaccaccat     1800
cagccaaatg atgttacgct aaaaacgtgt taattcagca ccaggctagc accttgtaaa     1860
catgctaatt catcatgagc gtcatgtctg cactctcagc cctctaaaac ctctctgttg     1920
aagctgagcg gcccaccatc atcactgagt atattaactc gggtgttgga atttcccagg     1980
tgtgtttaat ctgtatagct ttgtatttta aggcagaact ttattctcag ttattcatct     2040
caaaatgaga gttttcagaa aagatcgaga aaagggatgg tccttctgca aaagttccaa     2100
agtgcaccct gaataataaa aatgctaaaa actggccggg tgcggtagct cacgcctata    2160
atcccagcac tttgggaggc caaggcgggc ggatcacgag gtcaggagat cgagaccatc     2220
ctggctaaca cggtgaaacc ccgtctctac taaaaataca aaaaattagc cgggtgttgt     2280
ggcgggtgcc tgtagtccca gctacttggg aggttgaggc aggagaatgg cgtgaacccg     2340
ggaggcggag cttgcagtga gccgagatcg caccactgca ctcaagcctg gcgacatag     2400 cgagactccg tctcaaaaaa aaaaaaaaaa aaaagaaaa gaaagaaaa gaaaagctaa       2460 aaacttcccc ccccactttt tttttttttt tttgtgagat ggaatcttgc tctgttaccc     2520
aggctggagt gcagtggtac gatctcagct cactgcaacc tccgcctccc acgttcaagc     2580
gattctcctg cctcagcctc ctgagtagcc cggattatag gcatgcacca caatacccgg    2640
ctcattttca aagtctttat ccccttggta tatcacctgt aacatatgca ttggaaatcc     2700
attgcatttc cattgctaaa acaacaatg tgtaaagtcc tgaacttgga ttccctcaga      2760
aaaatgtaaa ggagtataaa atgcaaactc caggtataaa atgtaaaata tttcatctac     2820
tgaaaagaac tggtgtacac agtcggttat ccttaacact tcagcctgca gccatgggga    2880
aggtgtctga gctttggatg gaagttgcag ctcccgggca gtatgacctt ggacaaatca     2940
ctaaatgttc taagcctcag tttccttatc tgtaaaatgc aggtaatcat gactacttta     3000
aaagttgtca taaaacttaa aattaaaaaa aatctataaa gcaagtaacg tgcgttgtag     3060
```

```
gctttcatca aatggttatt actattgata atctgagttt aatgtgcctt tgccacttta    3120
ctaatccctg agccatgaga tggcacaaag ttgctgtgag gattaagaga gatggggagt    3180
attaccccta tcacagtgcc tgactagagc aggcacttgt tagatgctac cacagggatg    3240
cctcagccaa cgggtggaga gaggttttta acagagaggg agagagagag agtgtgtg     3300 tgtgtgtgtg tgtgtgtgtg tgatcatggg ctgaaactgg atgaggcagt cacttgagct    3360
gccagatagc caattgtccc tgcatctcgt tcccctttt  tctactccag tccttggcag    3420
caaaccaagg tcctacatga cacagagaag ttagcaacca aagccattat tattttggtt    3480
cagctgataa aagattggct ctccctcaaa aaactagacc agccaagtag gaaaaaaat     3540 tgttttctta agaaaacaac aaaacccaga tggaataatc agaataaaga ggaggtcagg    3600
tcctacgagg agctaggata aattggggga atccctcagg tttttttttt ttttttttgg    3660
aagtgccagg tcaaataaga tggagattta ctggagtcac actgctgttg gcacccgcct    3720
aacccgggcc tcctttttct caaagacaca ggccagatgc cagccttggc ctctctttgc    3780
tcaggaactg gctgactccc tgccccagga tttcacggcc atgacctctc tctgggaaaa    3840
gttcccacta tttgctgctg gggaaaccag gaccccaccc cagggctggc caaggtgagc    3900
aggctgagtt caaaagagac tcaccgggga catttgcaaa cacgtcttcg gttccctgga    3960
taaggaaaaa gaagggaaaa agtgagtgcc cctatccatc aatagtcccc aaagacagtg    4020 tatttttgt tgttgctgtt gttgttgctg ctgtttttg gttttacaaa aaatcatttc      4080
agaacgatca tgggctgaaa ttggatgagg caaatagga attgcctcta cgaattctcc     4140
ttcctttccc ctatttcttt gaggattata actcttgaga gccgggtaag ggcttcttat    4200
ccatccttcg tctcaagcat caattaaaaa aaattgcaac tacagacgcg ggcgaaagcg    4260
gggagcctgc agacctgatc cggcacctct cttgcatggg acccaaagca gggtgggcgg    4320
ttcgccgaag agggccaagg acgaacctca aactgatggt ggttttgact aaccctcctg    4380
ggcacttgac tcggccacag cggccccctc ccggcgggcg tttgtcatgt gtccagacat    4440
gtgcgcgcgc gctgcgggct tcgtcgacga acacacccg ctgcagcggc tctgggaacg     4500
cggctttgtc tcccaaaacc tctccgagag cgcaaggagc gggaagggct ttctcgcatt    4560
ctatctccca gaaagaagtg cctgtacctg cggggcagct cgggagtccc agaaaactca    4620
accccaagct cccccctcgc aaggtccgcc tggagctagc agagccaagg gcaggagcgg    4680
ggccgactcc ttcccgccgc gattcctcgg gacttactgt ggttgcagta aagggtgata    4740
accagtgaca ggagaaggac cccacaagtc ccggccaagg gcgcccagat gtagatatca    4800
caggcgaagt ccagccccct cgtgtgcact gacgacacca aagacgccga catttaggag    4860
agggcccggg acctcccaac cgccccaccg tcccgggaac gtctctccgc ctcagatctc    4920
ggtttcccac cacttggaca gcccttgact ctacctacag tatcagggct gtccctggca    4980
tgggctctcc ccgcggtgcg tgccgccccc gccccgggcc ccgcacgccc tcacctgcgc    5040
cccccgccgc tggccggcac gcctctgggc gcagggacag gggctgcgac gcgatggtgg    5100
gcgccggtgt tggtggtcgc ggcgctggcg tcgtggtggg cttcgctgca agagcaacag    5160
agcgtggttg ggggccaggc tggggttatg gaggcgcccc agccccggcc tcgcgcacct    5220
ttccccacgg ggacgcctcc ccccggtttt cctgggagaa gggatagcag aggagacagg    5280
atggggaccc cggatgcgcg gcggacccct gtgctcggc  ctcggctcag cccagcgcac    5340
ccggcgccca gagccggagc gcaggagcca gctcccctgc acctggcctc tctcccgggc    5400
```

```
tgaaccagca accctggagc gcgggttgat tgctgtccgc attttaccca cgagcaaacg    5460
gaggcgcaga taatttaagt catttgccca gaatcacaca agaatccgaa ctcgagtcca    5520
gatcggccgg acgtaaaaag ccatccccag tccctactca gcctcgcgtt agcctcagtt    5580
tgctgtgtct gtgaaatggg aacagtatct aagtcgcttc caggtgcgct aagaggcttg    5640
aaagcagggc ccaggtgtgg aaaacaggtt gaggtgaacc ccaagcccca cgcggagagg    5700
tgccgcaacc cggcgcgcgg acctggcagg aagaccggca cgaagtggct gaagtacatg    5760
atggagttgc tcagggccga gcagaaatag tagccctcgt tctctcggcg gaagtcgctc    5820
agggtgagga cgaaggtgtc ccccaacctc ttgcccgaga accgctgggt gtccagcccc    5880
tcggccgcct tgggcttgtt ttgggagagg tataggagga aggtgggact ggcggcggcg    5940
ccgcgcggct ggaagagcca cgagcagccc gacgtcgggt tggacagcag cacctggcac    6000
ttcagctcca ctgtctcgcc caggttccag gtccgatcca gcggcgacac ccggaactgg    6060
ctcggcctgg cggcgtctgc aggcggcaag cagcgaggct gagcccgcag tcccgcgccc    6120 cccgccccccc gcccgcccca tccctgcct tcccgggcgt ctcaaactca cggagcagca    6180
aggccagcgg caggagcaag gcggtcactg gtaaggccat gacgcgctcc ccaggacgct    6240
gcttggctcg aagctcgggc gcgaggggag gcgcgcggga ccggtgggg cgccgagggg    6300 ggaaagttgc gcccttcggc cggcccggag cctgatttcg catttggagg atgtgatgtc    6360
acccgaagcc cccgccgagg agagtcaccc tccttttcgc ggttgtcgcc ttccagcccg    6420
gcgaggaggc tggggcccgt gaataggggc gtcgaggcag cctggccagg caactggggg    6480
cagctgaaaa ctgcgggttt ggggatgagg aaaaggcctt ggaaatagtc cttggaaatg    6540
gttgtcttgt gagagtgaca gagtgggtga agggagacca agatttcaa gaagtgaggg    6600 cgagagtagg cagcaaagga ggggagtgtc ccttcctttg ccttcactaa aggcgtctct    6660
tgtactgtca ccttgggact ttttattggc aaaatgggca ctgagggctg aaaaggaaga    6720
ggaactagcg acctgcccgc ttctgaggaa ctcgctagag cagccccagt tttcaccgag    6780
gaaggaccct ctcccttccc ccaggagatt tccatgagag cggcagcagc cgaagctttg    6840
ggtgtcggtg tcagtgcgct gctgacctca ttcttccggc cttttcatcca gcggctaaac    6900 tcaccacaca gcctcatctc ttcttggagc cattgcaaca gccttcaatt cacaccagtc    6960
tctctcctga tcagtcctcc agccacgttg ttataaaaat tattattctc acaaggggga    7020
tctgacagcg tcactgctgc agcctcccat ggcctgcatt gctggatgga aattcaaccc    7080
ccagcttggt tgaccagccc ttgggtgctg gctcctccca gcctccgcac agccccctgc    7140
cctgcctttc ccatacacct gcagctgcag cttcacaggc ttgaagtcat tcaacccctg    7200
cgctctgtgc tttcacgccc ttgcacttgc ggtccctcgg cctggaatgc tggtctgttt    7260
aagccctgga ggcagctcct gtgctgtctc atttggacct catttctttc accccccagct    7320 ctgggtgctc tgcagggagg tgtgggtgat gtgggtgaat gcttgggtag aggcggtttt    7380
ctcttttctg tccctaacac atgtgtgtcc ccttcctttt tgtttcttta aaaaataaaa    7440
taaaataaaa aagactggag tctcgctgtt ttgctcaggc tggccttggg actcctgagc    7500
tccagtgatc ctcccacccc agccccctga gtagctggga ctacaggctc atctttcctt    7560
tttgactgtt gctgtcctga aaccttccag ctccagtggc atgccctctt cccatttctt    7620
cagggtttct gagtctttcc actttgaatc ccatagtggc tgcacctcac attgctactg    7680
cttgatccta gagacaagac acctggcatt ctgtgttcca tgtgtctgcc ccacccatta    7740
gttctgctgg gcgaggacca tgccgagact tcatgatgtg tcctccatcc ccagaaacac    7800
```

```
agcatgggct gagctgtgct tgttgaactg cattctcctt gtccttgtga agtacaaact    7860
taagtgttgg atgggttctt tgtcgttgtt gctattttttt tttttgagat ggggtctggc   7920
tgtgttgccc aggctggagt gcagtgtggc accacctcgg ctcactgcag cctctacctc    7980
ccaggctcaa gtgatccttc cacctcagcc tcccaagtag ctgggaccac aggagcacac    8040
caccatgccc agctaatttt ttgtattttt ggtagagatg gggtttcacc atgttgccca    8100
ggctggtctc caatgcccga ggtcaggcgc tttgccccgc cttggcctcc aaagtgttga    8160
gattacaggt gtgagccacc atatcagggc ctggatgggc tttttttttt tttttttaatt   8220
attttgattt cagtacctcc ttccagctcc ctcaaagcat ccaagatgct tattctagca    8280
tggaacatgt aacattttat attcagaaat ttttaaaaat gtcttttaag tgacaacagt    8340
gcaatatatt cttgtacgaa aacaaacaca aagttccctg tctcaactct cctcactgtc    8400
acctgctccc cacagaaaac cactgttaca gttgaatgtg tcccttagat attatctgta    8460
cataaacaga tgtttataca tcatcttaga cacatgggat tgtatgagat aaatattttt    8520
ttgcaaccta tcttgtttca cagtagaagg agagcgttca gcagatgaag atccaccccca   8580
ttcttataaa tgggtgcatt atatatgggt gttccataat ttaattctgc tgttagtgga    8640
catttaggcg atttctcatt attgcaacac tagcaaggct gtggtagata taatgtatct    8700
gtatcactga gggcttgcac cagtacctgc agcttttttca aatggagat gagggagttg    8760
gggaagaaaa caccttttaca atgatggtta taactggcct atcgatgtat gcatgtgtgt   8820
gtgtgtgtgc atggtatgag ggtccctcgc tgtgtagaca cagtgctgtc cctcaactca    8880
catgaatgag ggagacaagg aagcaatcaa gtccagacag gccaccaaca catcaattct    8940
tgctgtagat ggtagtttgc cattttgctc agcaccacca gcactgtatc aggagtgtca    9000
aatggccctg ctggccaaag gctacaatca acagggtggt aaggaagatg gctagacacg    9060
aaactgcact tgcccagtgg tggaagcact gagggggcca gagtcaacct ccacctatt     9120
ggatcttgag aatcaggccc ctgagtgtga tgatggccag atttggggggt gtactgcttt   9180
aaaatagact agttccatct tagtctcacg gaaatcagct tgggggcctt ctagccctgc    9240
agctcagaaa agtgtcagcc agtggggtgg cagcccctttt gtacagagca ccatgggggt   9300
tggggtgggg aggataaggc aacatgtcaa acccatcaag gaggctttgt gaccccagtg    9360
atattttttg cagaacgtgg tggattttcg atgtgaccac aatgacatcc gccttgcagt    9420
ggcagaacag atgcaattgc acaagttctg gagaaacttt ctgtagacca ggtgtgcaga    9480
gggctggggtt gggcctgtcc atcactgcca ggtaagttcc caaacccccac actgtagcac  9540
tgacttggga tggcatgaag aaatgtgaat gactgcactc ctttaagcaa gccccttatt    9600
taaaaaaata tccagaagta gatagagtaa gatagtaacc agtttctatg ctgatttaaa    9660
ctggtccatg gaaatggaaa actttaatgt agattaaaga catattcaaa atgcaaaacc    9720
gggcagagca gtggtaggaa atccatcagg gttctgtgcc actgctccta agacatgaac    9780
tgcagggaca acttggaatc atggctggga aattgcctgc tgtgtcccca tcgccaattc    9840
aggtctatgg agatgttact gttcttggaa ggagttagct tgtccagggc tagaaactct    9900
agagttatca gggcttgttt tatcttaatt ggaaatacca atcaatttgg cctcacttct    9960
gtcacctttc ttttcctcca ccccgagttc cccaagttca tctagctgct gtccttcttt   10020
cctggacttt tgcaatggcc tcttaactgg ccaaccccat ttctgctctg gtcccttcta   10080
gagaaaatct catcatgcca acccccctgct tcaacctgaa aggacttcct ggtgtccta   10140
```

```
gtagaatgtc ggggatccct aatgttgcct gtgaggccct gcacacttgg tttcatagtc   10200
tctgtcctct tgtctgtcac cttcttcact cctcctaggt tccgcatctc tcatttctca   10260
agcggaccct agtcctttcc acttcagagc cattaaacat gctattccct cagccaagaa   10320
tgttctcacc tctgctctct gcttaccaaa ctcctctccc ttaagaccca gctcaagcat   10380
ctccttcctg tggggtttag ctccttcccc ctcccactcc cagacagtac agaccacatc   10440
cttctcttct ctgtgtcacc cggaccttgg gtatctgcag actggagcac aatggtttgt   10500
ttgcctgtcc agcttgacaa ccaaacccdtt ggtcccttga ggaaggagcc ttgtccctct   10560 catgttttaca ccagggtgcc aaacagaggg cttggcacac acttgagtgg cacacactca   10620
agaaattctt gctcagtaaa agctaaagga aggtagaagt agggtacagc agaccagagg   10680
aggcttagat agttcattcc aagtaagagt ggtcaggaaa ggcttcacat atagttgggt   10740
ttgaagataa aggaagaatt aggagagagg ttgtttagaa tgaggcattt gatatgtctg   10800
atcaagatca gctgatacca tgctttaaca tatagcaatg gtatagttaa aaacaaaaga   10860
agaggaggaa ggggagaagg cagatgtact caaaagcaag ataaacgtct tcaaggatgt   10920
agttgcagga caatggctgg aatcaggggc tggcttgctg ggatctgttc ttagcaaacc   10980
attcttgggc ctgggtcttg agggtctgtt cttagtgtag aggcaccaag agtttgactc   11040
cttcagctaa cagagtttca cagtgctttg cctatagagg aaggctggag ccaggctctc   11100
tgcttgaaac agggatttgg atctgatttt ctcttgattg aaagagagcc cacagccacc   11160
catgtaaggc ctagttctga ctgtgggccc tggaaagtca gaggctactt taaaaaactc   11220
aggaaaagag agagtaaaga gaggaagaga ttttcaaaaa tttctattca agataaccct   11280
gcacacacac tcgaaattca aagtatacat aaaaaagact caacaagtgg aatgtgaatt   11340
cacttccaaa aagaggcaaa ttattgaaca atttgaaaaa tgtttaaaac aaagagaaca   11400
acaaatgtag aaaatgcaga aattaaagaa gaacagttga agatgataaa tactgagcat   11460
actggaaatg aacactctac atattaaaca aggatatact ctaggttgga catagttgaa   11520
gggataatta atgaattgga agctagcatt gagaaattca tagagaatgc aacacaggga   11580
gatgaagaca gaagcagttt gaaaaagctg ttgagatgta tattagcatg gtgaagtgtt   11640
taataggatt tcagaaaggg gagaacaaag ggaatgtgga gaagaaatat gggaagaaag   11700
catggctgaa aattttttcac aattaaagac aaacattctc agatcaaaaa tactcttagt   11760
gccaagtata aaaacatata catctttgca catatcaagg tgaattataa acatcaagag   11820
taaagagaag agggcatccc aggaagctag gatgttgaa atataattgg gagaatcctt   11880
gttgcagttt ggattgggca gagagggtaa gaagctgaac tgtaatgggg aaaaatatac   11940
acattttggt tacaccttgc attgactctc tgtcatcccc tcccttggtg ctgacacatg   12000
cttactgtaa aactgatcca atgatcccat agagttgatg tttgtggttt ctttgaataa   12060
acatataaat tgatccttgc cttcttaaaa cctgagaaag ttcatttgt cttatctgag   12120 ttcctttcta gggaaaccaa ctatcaggcc tcccagatgg tagcaatgag ctgaaactca   12180
ccagatcact tattatgaac aataagacgt cagactcttc acctggtatg atggcctaac   12240
taacctcctg tttcctgttg tccaactcct tttccttact cctcccaact tcctgttttc   12300
ccacacatga ttacatgtct tccctgctat ataaacccct taattttagt caggtcagag   12360
ggatggattt gagactgatc tcctatctcc ttggctgcag cacctgacta aattcttctt   12420
ccttggcaat acttgttgtc tcagtgattg gctttctgtg aggtgagcag aaggacctag   12480
atggatcccc cggtgtttcg gtaacaaaat tgttttggat cttaatctc agtaacactg   12540
```

```
aaacagaagc gttctgaatg caactggaga gccaggattt gagttcgaaa gaggggtcag   12600
ggctggggat gtagccttgg gaaggaggtg ataagttgtg agagtgggtg tcattgcaaa   12660
gggaggtggt gtggaaagaa catacagaag agtatatgga accttcaggg aaggctcgta   12720
ttgaagagca ggaaataaaa cattggcaag gaatccaggt agtgcaggaa attcagaatg   12780
gggcttgaga aggtggaaga acttcacagg ggaggtttgg gctataagag aagcacagag   12840
aggacatcaa agcctgtggc aggtagagat tgtaagctca tgtctgcccc tgacccacat   12900
gaggatgtcc cacatgtttg ccattggtgg atgataagat gaggaggact cacaggagaa   12960
aggccaacaa gggagggtag gggcagcatg gggacttgtg gagggcaatg tcagatgaag   13020
tgatgttgac ttctgaactt cattcattat tcactcattt aaatatttct gctattcact   13080
tttttaaaaa aaagttttga aaacatttta acatagaaca atatgtcaaa taatataaaa   13140
tgcccactct ttataagtgt tagcattttg tcgcattttcc ttcacatgaa cattacagat   13200
aaaactgtac cctcccaagt accacccccac ccgccttctc atgaaaagct aaatttggag   13260
ttttgttcat taattatgac agaaagatgg taagtttttt aattttttaat ctgttaacct   13320 ttcctatgga gctgagagag aaggatgccg aatgtccaat gagtgtggat ttgtctattt   13380
ctccttttaa ttcagttcat attttgtctc ctatattttg aagctttgtt attaggtgca   13440
tacacattta gaattgtgcc ttctggatga attcactctt ttatcattat gaatgttcg    13500 tctttacctc tgcctctggt aatactttgt tgtgaagtct accttttatt cataaggaac   13560 agagcttttct ttctttttttt ttttttttgag atggagtttc cctcttgttg ctcaggttgg   13620
agtgcaatgg cacgatgttg gctcaccgca acctccacct cccaggttca agctattctc   13680
ctgcctcagc ctcccgagta gctgggatta caggcatgca ccaccacgtc cggctaattt   13740 tgtatttta gtagagacag gtttctcca tgttggtcag gctggtctcg aactcccaac    13800
ctcaggtgat ccacctgcct cagcctccca aagtgctggg attacaggca tgagccactg   13860
tgcccggcca gaaacacaac tttcttatgc ttcccgtttg cataatgtat ctttttcctt   13920 ttctttttttt ttttttgaggc agagtctagc tctgttgccc aggctgcagt gcagtggtgc   13980
gatctcatct cactgcaacc tttgcctcca gggttcaagc aattcctctg tctcagcctc   14040
ctgagtagct aggactacag gtgcacggca ccatgcccag ctaattttta tatttttagt    14100
agagatgggg tttcactatg ttggccaggc tggttttgaa ctcctgacct caggcaatct   14160
gcccacctgg ccttccaaag tgctgggatt acaggcatga accactgtgc ccagcctgca   14220
taatgtatct ttttctatcc atttactttc aacttcccct tctctgtttt gaatgttta    14280 ctagatatgt atacatgtat atgtgtatat atatctataa atgctatata atttatttt     14340 ctgagagttt caaaatacag aaatgtcatc atattgtgtg tctttgagct atgttgatac   14400
atatagattt attttaaatg ctgtgtggtg tattatcctg tgaatgtgcc acagtttcat   14460
gttcagtggt tcttgaacca gagtgttcat ctctctggaa gtatatggag gctgtccttg   14520
gggatacaca taattttaag gaaattgttt tccagattct caactcccat tggttctctt   14580
ctcataaaat ggacctgccc aagaacaagt ccctgtgttt aggctttgtg ctcgttctcc   14640
tttctggcct attctttcat gattatttta tttcccactt taaaactgaa aggcaaactt   14700
cccgccctcc tgttccttac tatgctccag aggtgggcac gtaatcctct gggccaccaa   14760
taaaaagaca aatccaaaca ttttttcatgt aatttccatc cgttagaaat tgccaaagaa   14820
tgcatttctc ctgagcagag tccccagtat ccaggtagag tcatctgggg gccgggcacg   14880
```

```
gtggctcacg cttgtaatcc cagcactttg gaaggccgag gtgggcggat cacgaagtca      14940
ggagatcgag accatcctgg ctaacacggt gaaaccccat ctctaccaaa aatacaaaaa      15000
attagccggg cacggtggcg ggcgcctgta gtcccagcga ctcgggaggc tgcggcagga      15060
gaatggcttg aacccgggaa gtggagcttc cagtgagcca agatcacacc actgcactcc      15120
agcctgggcg acagagcgag actctgtctc aaaaaaaaaa gaaagaaaag agtcatctgg      15180
gagggatgca ggaggcagag tgcctcacag caggctttgg ggcctcatcc ctctactcag      15240
ctctctatca tcgagctaga attcagaggt gagacagtca ttatgaggat gcatattaac      15300
gtgttcatta tgattacaaa aggaatcaga attctttttt ttttttttaa cagaaattaa      15360
gtctgagttg ttaattggtt tgacattgaa gaccagcttt gccaatgagg ttaatggcag      15420
tattttaact ttccttgaat ctagtgagct aaatctttag ctccaaggtt ttgatgagaa      15480
tcaagtttag cgctaaagaa acagcttaga aaagaaaga aagaaaaca cttttaacaa      15540 gtttaaaatc tatgataaga taaaagcatt ttggccaggt gcggtggctc atgcctgtaa      15600
tcccagcact ctgggaggcc gcagtgggtg gatcacaagg tcaggagttt gagactagcc      15660
tggccaacat ggtgaaaccc cgtctctact aaaaatacaa agaaaattta gtcgggcatg      15720
gtggcaagcg cctgtaatcc cagctactca ggaggctgag gcaggagaat tgcttgaacc      15780
caggaggtgg aggtagcagt gagccgagat cacaccactg cactccagcc tgggcgacag      15840
aaaaaaaaaa aaagaaagaa aaaaaagat aaaaacatta tatcacaata ttgtttgtat      15900
tggaatttgt cttgaaatta aattaaaaat atttctaata ccccaacact ttccaagtta      15960
atcaatttca gcaatcgttt ttaagtgaaa gaagaatgat gtcattgatg gctacttggt      16020
aggcttcggt aaaacctagt ttagggcttc caaaacccaa gaaagtgaat aaatctaaaa      16080
atggtaacaa acccatgtgc aggtcagtgg ttcccaagtg tttgctttca acaaaattgg      16140
aagaaggcct tctagatttg gcaactatca caggttgaat tgtgtccccc caagtatatt      16200
tgttgaagtc ttatactcta gcatctcaga atgtgacctt atttggagac aaggtcctta      16260
cagaggtaat caagttcaaa tgaggccaat aggatgggtc ctaatccaat ataactggtg      16320
tccttgtgga aaggggcaat caggacacac acacagagaa catcatctga aaacaaggca      16380
gagatggggt gatgtttcta caagtcaagg aatgccaaag attgccagca actgactaga      16440
agctaggtga gaagcatgga acaaattcct tctgtagccc tcagaaggaa cacacccagc      16500
tgacaccttg atcctgaact tctagcttct agaactgtga ggcaataaat ttcttttgtt      16560
gaagccacct agtttgtggt actttgttaa aacagccctg gcaaactaat acagcaacta      16620
atagatcatt aaaattaatt tttgatgata gataacattg tctccctccc tccctgcctc      16680
cctcccttcc ttccttcctt ccctccttcc cgctctcttt ctctctctct ttttcccttt      16740 ctcccttct ctctctctct ctctttctcc cttggagaaa gggtcttgca ctttcgccca      16800
ggctggagtg cagtggagtc actgcagcct caacctcctg ggctcaaaca gtcctcccac      16860
ctcagcctcc caagtagctg ggactatggg tgcacaccat catacctggc taaattttg      16920 tagagatggg ggttcaccat gttgcccagg ctggtcttga actcctggac tcaaggaatc      16980
catccatcca ccttggcctc caaaatgctg ggattacaga cgtgagccac tgcacctggt      17040
tcatgctttt gtcttttga aaaaaaagg aaaagttaa aagatttagt gattctgctg      17100
taacaaagcc aactatttat ttatggagac aaaattctc agtacttaca ttgtatgaca      17160 aacaaagca aaacaaaatt aatactgaac tctgtctcat tctagcaatc aataaataaa      17220
ataaatcctg ttatttatg ggttcattaa ttaattggac cacaaaattc atttgtgggg      17280
```

```
ggtccatttc attaagagct gaattttccc ccaaaattat gttttaaaaa gcttttttg   17340
agataattgt agattgacat gcacatacaa gaaagggtac agagaattcc ataccttca    17400
cccagtttcc cctaacaaag gttactttta tatttattta tttattttta gagacagagc   17460
attcttctgt tgcccaggct ggagtgcagt ggtgtgatct gggcccactg caacctccgc   17520
ctcctggatt caagtgagtc tcttgcttca gcctccctag tagctgggat tacaggcacc   17580
cgccatcatg tctggctaat ttttgtattt ttagtagaga caggatttca ccatgttagc   17640
caggctggtc tcaaactcct gaactctagt aatctgcctg cctcggcctc ccaaagtgct   17700
gggattacag gtgtgagcca ccatgcctgg ccaaaggtta cttttaatgt tcattaattt   17760
tgaagacttg cagtttattt atgctataaa ggacaattgt gcactattaa tagtcgcaat   17820
gatgacataa tctaagactt ttaatattta gaaacttatg gttgcaggaa attaaaaatt   17880
catctcatgt gctttttttgg cagagaagta tgaaatattg atcaatataa ggtccttaag   17940
catatgcacc tattaaactt ttatggagga agtagaatag aattcataag tccatttgtt   18000
tttactcttt attttttga gacagagtct cactctgccg cccaggctgg accgcagtgg   18060
cacaatctcc actcactgca acctctgcct ccttggttca agtgattctc gtgtctcagc   18120
cacctgagta gctgggattg ctactcaggt gtgcaccacc acacccgact aatttttgta   18180
tttttagtag agatgggatt tcaccccttt ggccaggttg gtcttgaact cttggcctca   18240
agtgatctgc ctgccttggc ttcccaaaat gctgggatta caggtgtgaa ccatcgcgcc   18300
tggcctagaa ttcataagtt taaggagaaa aaggagtgat gaaaaatttc caaaagttaa   18360
gaacttttc ttgtatttta aaaatgagtg acggttgaaa caaaattgat atattattta   18420
tgtgctatta gaaataatta aaaagaataa ggttttcttt tttaaaaatc aacatttact   18480
ttggaaatta tgtcctttat agtgatgaaa atgtttgat gtcaagttaa aagtgagtaa    18540
agaagtacat tcattttata acagcatttt tcacagtagc taaaatgtgg tagcaaccca   18600
agtgtttatt actggatgaa tagataaaca aaatgtggac tcaggcatct ctcttctggg   18660
ctcatacccca aggaaatga aatcaccacc tcaccaaggt atctgtactc ctgtgtttat   18720
tgtagcatta ttcataataa ccaagatatg gagacaacct agacaaccat caatggacga   18780
atggtttaag aaattgtggt acggatatat acaagggaat tcagccttaa aaaggagga    18840
gatagcattt gccataacct agacgggcct ggaggacatt atgctaaatg aaagaagcca   18900
gacacagaaa aaaatattg cacgatctta cctgtatgtg gaatctttta tttatttatt    18960
ttcttagacg gagtctcact ctgttgccca cgctggagtg cagtggcgca attttggctc   19020
accgcaacct ctgcctcctg ggttcaagta attctcctgc ctcagcctcc tgagtagctg   19080
ggactacagg cacctgccac cacacctggc taattgtatt tttagtagat atggggtttt   19140
gccatgttgg ccaggctggt ctcaaactcc tgacctcaga tgatccacct gccttggcct   19200
cccaaagtgc tgggattaca ggtgtgagct accatgcctg gcctgtgaa tcttttaaaa    19260
aggtcaaata tatagagaat aaaacagtgg ttatcaagat tggagtagga gagaggaaat   19320
gggcagatgt aggcctaagg atacgaagta gcaaacatat aggatgaaca agtcaaataa   19380
agtacaatat gaagactaca attaataata gcatattatt ccaggatttt tgctagatga   19440
gcatagttgc ttttgctaca ggaggaaata aatgggtaac taagtgagat gatgcataag   19500
tcaatttgtt tcactatagt atccattcta ctaaatatgt gtgtcttata ccatgatgtt   19560
gtatataccct tatatataca caataaaaatt tatttaaaca aacaaaatgt ggtatataca   19620
```

```
tagagtggaa tattattcag ccttaaaaag gaagttctga cacatgccac aatatggatg     19680
aatcttgagg atattatgct aagtgaatta agccagtcac aaaaaaccaa atactgtatg     19740
attctatgta tttgaggtat ttaaagtagt caaaataata gagacagaaa gtagaatggt     19800
ggttgggaca ggctggggag agggaggagt gggagttatg tttaacggtt atagagtttt     19860
agtttttcta gatgaaaaga gttagagaga aggatggtgg tgaaggttgc acaacaatgt     19920
gcatgaactt aataccactg aactgtacac ttaaatgtta aaatggtaag attgttatgt     19980
gtattttgcc acaataaatt agtattatta ttttttttag agacagagtc tagctctgtc     20040
aaccaggttg agtgcattgg tgtgataaca gctcactgca gcctccaact cttgagcccc     20100
caactcctgg cctcaagcag tcctcctgcc tcagcctccc aaagtgctga gattacaggg     20160
gtgagccatt cactgttcct tgctaaatct tttttttttt tttttttttt tttttgagac     20220
agagtctcgc tctgtcaccc aggctggagt gcagtggtgc gatctcagct cgctgcaagc     20280
tccacctcct gggcttaaat gattttccta cttcagcttc ctgagtagct gggattacag     20340
gcacacgcca ccatgcctgg ctaattttttg tatttgtagt agagacagag ttttgccatg     20400
ttggccagac tggtctcgaa ctcctgacct caagtgatcc acctgcctaa gccttcctaa     20460
gtgttgggat tacaggcatg agccaccaca cctggcctaa attttttttt ttaatgagtg     20520
aaggagtcca tagtctttca tactttgggg tgatacaaga aaggaaaaa ggtttaatga     20580 caactgccac tttcatttat tcattccttt gttgatgtac ttttgggctg ggttttgctg     20640
ttataagcta aactacaatg gacatccttg tacacattcc ctagagtcca agtacaagat     20700
tttctctagg gtgttttcct ggaaaaggaa tgacttgagg agtatggcaa ccttgtgaga     20760
aatgactgat tcgaaagatg tgtcccatag cttttgatac attttctcc gaagtcatgg     20820 ttccagtcca cactcacacc agctgtggag gagttttcat ttacccacga gctttgttat     20880
ttctggtttt gtcagtcttt tcaattctgc caatctcata gggtgtgatg gtatctcgtt     20940
gtttaaacct gacttctctt gttaaggttg agaccgagca tctggcccca tgtttgctgg     21000
ctattcagct ttcctcttct gcagactgcc cgtttgtcca ctgctctgtt tcagtaactt     21060
ccatatacca agaactctct gccttccata actcacatca cttaaaatac gaattttttt     21120
gatgcttaga gaacctgatt tccttccaac caattgtgct ctcctaattc caacaaccaa     21180
atgaagcttc aactcttctt tttgttcaga gccctcctga gtcctgtcct actcacagta     21240
aaggctgtgg caaaataaat aaataagtaa ataaagggga aaaatacact gcatccaaaa     21300
aaggctcgtt tcttttttctt tcttttctctc tctctctttc ttttttctttt tctcttgttg     21360 tgacaattgt cacaacaaaa tgtgtatgtg acaatttgtt atcttaaaac agtttaccca     21420
aaatagaaac cttacaaagc cagtggaaac ttttctttttt gcataagttg gttaattctt     21480
ttgagtgctg gcctgggatc catgaaataa cctcaactcg accataaaac ttttcactcc     21540
cacgttatgc aaacggtgat gaccttgttg gtggcaagcc ccccgtgtga ctttccgagg     21600
ggatctgagt ggtgcaaggt ggaggacgca gtgatgaaa cattgcgaga gggaaggcgt     21660
ctgtttccac ccacttaccc tcagagcatg agggctgggc gaaggctctg actcctgtag     21720
ggggtgaccc atttctagga ctatagaagg agaggtgtgg acctgaaaa aggaaggaaa     21780 gaccacggca aggaaagtca agaagtggga gaagtcaagg gctctctcct cccttcctcc     21840
ttgtccttgg cctgcagcaa ctcctctttc tcttttgtg gggacagact gaagaggatt     21900
tcttagtatg gtttgtacct tcccagtaga gcaggaaaaa gaggaacgag ctgctcccctc     21960 cacacctcag acgctgaggt caactgccct ttgggcgggg cacgttggct cacgcatcta     22020
```

| | |
|---|---|
| atcccagcac tttgggaggc cgtgaggga gcatcacttg agcccaggag ttggagaccg | 22080 |
| gcctgggcca catagtgagg ccccatcctc cggcttgcac cactcaaatt ccctcgtaaa | 22140 |
| gtcacacggg gagcttgccc ccagcaaggt cgtcagtttg caaaacatgg gagtgaaaag | 22200 |
| ctttatggtg gagtgtaggt tatttcatgg atcccaggcc agcacccaaa agaattaacc | 22260 |
| atcttgtgca aaagaaaat tttccactac tttttaaag tttctatttt gggtaaatcg | 22320 |
| tttcaagata acaaattgga gagagaccta gagagaaatg agccttttta agatgcagtt | 22380 |
| tattttgccc catgatgttt ttgttttgt ttttgccaga gcctttactg tgagtaggac | 22440 |
| aggactcagg aggcctctga acaaaagaa gcgttgaagc ttcattggt tgttggaatt | 22500 |
| gggagagcac aattggttgg aaggaaatca ggttctctca aaaataaaa taaaataaaa | 22560 |
| taaaaaaaa agccagcgtg ctggcgcggg tccatggtcc aagctacttg ggaggctgag | 22620 |
| gtgggggat cgcttgagcc cggaagtcga ggctgtagtg agccgtgatt gcaccactgc | 22680 |
| actccagcct gggcgataga acaagaccct gtctcttaaa acaaacaaga aacaaaacaa | 22740 |
| aacaaacaac aaaaaaattc atttgggaat gtttctgcgc gtgcccataa gcagagccat | 22800 |
| gctataggat ctcccctgtg ccccaacaat cagcttctta cttggagggt agagaacggt | 22860 |
| gcttccccac gctgctgtgc aatggatagg agctatgtga agctggcgta tgggtggggt | 22920 |
| ttgcaggctt cgtccggctt catcgccggc tgctgacccg gcaccaattc ctgttctgca | 22980 |
| ggtctcaccg cagagggca cgccagccat gaggacagat gagggaacac gtgatgccac | 23040 |
| gatgggggtg ccaggatgag gtgggtgcgg tcgcggacag gcgcacgagg agcccagcgg | 23100 |
| agcgccaccc ggagcaggcg cggaggaggg ctggggaggg ccaccaaggc gacgagagcc | 23160 |
| ggtgtgcctg aatcagccta aaggagacg aggaggagtg tggtgggcgc aggggcaggg | 23220 |
| agctggggga agggcggggg gctagcccag gctgaaggca ggcaggagca gggccgcgat | 23280 |
| gtcagacaag aaacggcagc agtgtgtttg ggaacctagc accaaccgca ccggtggaga | 23340 |
| cagggtctgc tgtagaggag gtggggccgg gtcccagcta agtaaggcgg tggatcttgc | 23400 |
| agcccttcca tcctcagccg ctcattctgc gcaaatctcg gggccagcct tggtggagcc | 23460 |
| gtaaagcgtc caccagaacc tggatccctc cgccaccttt cccatgaatt cacctttctg | 23520 |
| tacacagcaa gcgcctgagc ggagacggcc gacacgtttc ccactgttac cccaggaaac | 23580 |
| cgcggctcct gagggggtca gggcctggc aggggcaga gctcagcgcg ccgtactgag | 23640 |
| gcagaaacgg ggtccagaga gggtgggtg ggggtacagg gaagggtcgc ccgaaggtcc | 23700 |
| ctggcgcagg gaggacagag gagggatcta gaattcgtag gggagaagag aactcagaaa | 23760 |
| agatccggcc cagcgcattt attttacaga g | 23791 |

<210> SEQ ID NO 3
<211> LENGTH: 692
<212> TYPE: DNA
<213> ORGANISM: Homo sapiens

<400> SEQUENCE: 3

| | |
|---|---|
| aaaggaagga aagaccacgg caaggaaagt caagaagtgg gagaagtcaa gggctctctc | 60 |
| ctcccttcct ccttgtcctt ggcctgcagc aactcctctt tctcttttg tggggacaga | 120 |
| ctgaagagga tttcttagta tggtttgtac cttcccagta gagcaggaaa aagaggaacg | 180 |
| agctgctccc tccacacctc agacgctgag gtcaactgcc ctttgggcgg ggcacgttgg | 240 |
| ctcacgcatc taatcccagc actttgggag gccgtgaggg gagcatcact tgagcccagg | 300 |

| | |
|---|---|
| agttggagac cggcctgggc cacatagtga ggccccatcc tccggcttgc accactcaaa | 360 |
| ttccctcgta aagtcacacg gggagcttgc ccccagcaag gtcgtcagtt tgcaaaacat | 420 |
| gggagtgaaa agctttatgg tggagtgtag gttatttcat ggatcccagg ccagcaccca | 480 |
| aaagaattaa ccatcttgtg caaaagaaa atttccact acttttttaa agtttctatt | 540 |
| ttgggtaaat cgtttcaaga taacaaattg agagagacc tagagagaaa tgagccttt | 600 |
| taagatgcag tttatttgc cccatgatgt ttttgttttt gttttgcca gagcctttac | 660 |
| tgtgagtagg acaggactca ggaggcctct ga | 692 |

<210> SEQ ID NO 4
<211> LENGTH: 16040
<212> TYPE: DNA
<213> ORGANISM: Homo sapiens

<400> SEQUENCE: 4

| | |
|---|---|
| agccccttag tcgaagcgcg tcctgctgcc agctactacc aagtccttag gccgagcccg | 60 |
| tttctctcct ggtgatgtga atcctcgttt tttgttgttg ttgttgtcgt ttactgaagt | 120 |
| cccgggctga ttagacacag caatggaagc tgggggtggc ctgggccgtg cattgaattt | 180 |
| gtgactttag caagtcccta aattcctctc tgcctcactt tgctgtctt ttttaggtta | 240 |
| aaaatatttt ggagaataga aaacagaaca aaacaaaaat aatggcttat agtgccaata | 300 |
| tggaattata gtcactccta acattttggt atattgtttt gcatttgctt tgtttctatt | 360 |
| ctatgcttat atatttttaa ttttttttcca tcactgtcat catatttcct attcaggtct | 420 |
| ccagcctgct ttaaaatttt tttaatcata aagttccata aaaattttat ttcagccaat | 480 |
| ttctttata acacgttctt catgaatctt atctgatatc tgcataatat tccactcata | 540 |
| ctttgcacaa ttagacatta aggtcgtgtg tacttttta attatgatac agcaatttct | 600 |
| aaatagtgta taattttcaat ttttgtttct tagttatcat aacagttctt aaaaggtgat | 660 |
| aacaaatttt taagtggata cattttttcc cccttctttg gtttataatt ttattgctct | 720 |
| gtggtctgag aatgtggctg tatttacgct ttttgaaatt gaagtttttg attgatggtt | 780 |
| gatttcgtaa ataagtttag gcacagtttt gtataaatga ttgggcacaa aattctttat | 840 |
| attagatcaa gctttgtaaa atgtattatc catatctgct atgtcttttt aaaatttta | 900 |
| tctacttgat ctaatttctg aaagagctgt aagttttta aatgtgtttg tggatttact | 960 |
| atttcttctt tatatatata tatatatata tatatatttt ttttttttt tttttttt | 1020 |
| ttttttttg agacggagtc tcgctctgtc gcccaggctg gagtgcagtg gcgtggtctc | 1080 |
| ggctcactgc aagctccgcc tcccgggttc acgccattct cctgcctcag cctcccgagt | 1140 |
| agctgtggtt actggcgccc accaccacac ccggctaatt ttttgtattt tttagtagag | 1200 |
| acggggtttc accgtgttag ccaggatggt ctgcatctcc tgacctcttg atccgcccac | 1260 |
| cccggcctcc caagtgctgg gattacaggc gtgagccacc gcgcctggcc tcttgtttat | 1320 |
| atttctaaca gtttgtgcat tatatatttt aaagtgatgt tatggagtat aaaaaccata | 1380 |
| tggctgttaa agtaataaac aaagaaacat tttggcttat atatcttttt gtgcatttga | 1440 |
| attattttct tggtttgaat ttttagaagg aaatggctct taaaggcaag ttggccttt | 1500 |
| aaagatttga cagatgtata ctgttggctg catcagagtt cttcttttcac taaccctcgg | 1560 |
| tcagccccag gaattaaaaa acaaattaca cacacacaca cacatacaca cagatacacg | 1620 |
| catatagtaa gtcttcactg tcatccatag gttcttggaa actgcaactt taagccaaac | 1680 |
| aacatataat aaaaccagtt tttcaatcaa cattgtaaca aaacaacatt gaatgaaaaa | 1740 |

```
atactttttg aggatctgct gtatgttatt ttgcttaaaa tcacagtttc caagaaccta   1800
tacatgatgt taagtgagga cttagtatgt gtggtgtgtg tgcgtgtgtg tgtgtgtgtg   1860
tgtgtgtaca tgcatcagtg ttattttggg agaagcaaga agtgggataa tttttacaat   1920
ctcctttgat ttttattgcg gttgacggtt tttctgtaga tctgtaatca cttgaatttt   1980
cttttttgtg tgtggattgt ctgttcttgt ccttttgtgc ttctgttttc taacttttaa   2040
ctgaaggagg ttaatgtctt tcagctctta acactgtagg aattacattg ctatttcttc   2100
taccacaaaa caccttattg aaaagaaaa actccagcac accaaacaga tgcctcaaat   2160
tcaccctgac tgcccctgct cccccctggat cttagcagaa atttcagtgt ggcaaacaaa   2220
gcagatagag ttcctatggg gcctaaagct tatgcaattt gggaaacttc tttaaccatt   2280 tttttttga gtagtgagat tttagcatat tttggctaaa atatggggaa aaataatgcc   2340
cagtgagatt acatgatttt cctgggattg atagattcat gtctcaattt ccatcagaga   2400
aagggagtgg ggtggtgagg aagggaaagt agtatggaga gttaggaccc tttgccttct   2460
ttcaggataa gaaagaaaag gaatagccga gcttgccata cacaagcggc cccattcatt   2520
tgtaatattc cttcggtatc cttttattgt ctgtgagatc catagtgatg atctctcttt   2580
tgtttctgat atgagtaatt tttgccttct ctcttttttc ttggttagat tgactagagg   2640
tttaccaatt ttactgatct tttcaaagaa atagcttttg ttttattttc tctattgttt   2700
cctgttttca gtttcattga tttctctaat ttttattatt tttattcttc tgcttgcttt   2760
aggcttgtat tgctcttcct tctcttgttt cctaaggtgg aatttagat ggtcaatttt   2820 agatctcttt tcaaaatatg tgtatttaat gctataagtt tccctcgaag tactgcattg   2880
ctgcatccca tgaattttga gaagttgcat tttcatttag ttcaaaatat tttaaaatat   2940
ctcttgagac gtcttctttg acccatgtgt tatttagaag catgttgttt aatcttcaaa   3000
tatttggaga cttttcagct ctcttttttgt tattaatttc tagtttaatt ctgttgtggt   3060
ctgacagcat actttatatg atttctgttc atttcagttt gttaaagtgt gttttatggg   3120
aaagaatgca atctcttttg gtaaatgttc catgtgaact tggaagaata tgtattttgt   3180
tgttggatag agtattctat aaatgtcaat tagatcaaac tggttgagag tgctgttgag   3240
gtcaattaaa tcattactga cttcctacct gctagattta tcaattattg agagagaagt   3300
attgaaatat ccaactataa tagtgacttt gtgtattttt ccttgcatac ctatcatttt   3360
ttctctcagg tattttgatg ctttgctaat acatgtatgc atgttaagga ttgttttgtc   3420
ttcttggaga attgaccctt ttaatattat gtaatgtcct tctttatccc tgatgatttt   3480
ccttgctatg aagtctgctt tgtctgaaat tagctactcc agctttcttt tgatagtgtt   3540
aacaagatat atctttctct attccttata acccatctga gtcttacatt taaggtgggt   3600
ttcttgtgga cagcatatgg ttaggccttg cttttttact actctgacaa tctctgtctt   3660
ttacttggat atatttagac cattcacatt gaaagtggtt attgatatag ttggattagt   3720
atctactatg ttcgtaactg ttttctattt gttacagttg ttttttgtct cttctttccc   3780
ctgtcccgtc cattgtaatg actgtttatc aacgttttcc caaagattgc ctgagctctc   3840
aaccagtatc atgtctatct ctgtgtgcag caaaatatac ttcctcatac ctgtgcataa   3900
taaggcaggt gcgaaggtgt tcatgcagca ctgcctttaa agtgggaaaa cccagtcttc   3960
atcaatgggg caataggaat ttaaattatg gttcaccgac ctacaggaat accaggaggc   4020
agtcaaacat aagccaatac atctatatgt cctggaatat agcaaattct gacatatatt   4080
```

```
gtcaagtaaa aaaagctagt tgcagaccaa tatatatatt ataactcttt taggtaaaaa    4140
tcgtgtgtgt gtgtgtgtgt ctgtgtgtga atgtctaaat gcacagaaaa atgtgtgtct    4200
aaatgcagag aaaaatctct aggtttatac aaactgtgtg ttttttacaaa ctgatggcag    4260 atttgggaaa gcaaagaaat attaattata tttttttctga caaaacttat attcatgtat    4320
ttgtaagctt taaacacaca cacacacaaa cacacacaca cacacacaca cacacgcaca    4380
acttatttaa gaccagactg gccaacatgg tgaaaccctg tctctacaaa aatacaaaat    4440
ttagccaggc atgatgccag gcgcctgtaa tcccagctac tggggaggct gaggtggaag    4500
aattgcttga acccgggaag gtggaggttg cagtgagcca agatcacacc accgcactcc    4560
agcctgggca acagagtgag actctgtctc aaaaaaaaaa aaaaaaaaaa agggctgggc    4620
atggtgctca tgcctataat cccaacattt tgggaggctg aggcaggcag gttgcttgag    4680
cccaggagct caaggccagc ctgggcaaca taaggagacc ccgtgtctac aataaataca    4740
aaaatttgcc aggtgtggtg gtgtgcacct gtagtctcag ctacccagga ggctgaggtg    4800
gaagaattgc ctgagcctgg gaggtcaacg ctagagtgag ccgtgattgc accactgcac    4860
tccagcctgg gtgacagagt gagaccttgt ctcaaaaata aaaaataaat taaaagtagg    4920
ccgggcctgg gtggttcatg cctgtaattc cagcactttg ggaggccgag gtggttgaat    4980
cacctgaggt caagggttcg agaccaacct ggccaaacat ggtgaaaccc cgtctctact    5040
aaaaatacaa aaattaacca tgtgtggtgg catgtgcctg tagtcccagc aggcagaggc    5100
aggagaatca cttgaaccca ggaggcagag attgtagtga gccaagatcg agtccctgca    5160
ctccagcctg ggtgacagcg agactccgtc tcaaaaatat ataataaat aaaaaaaata    5220 aattttaaa aagcaaagaa gcttaaaaac gctttccttc acaaggaaag aacatctgcc    5280
tgacataagt aaccctctct aacctcagca tttggcggct gttctgaaat gggtggtcca    5340
tactcatagt gatctggtgc tagagatgca ggaagcaaag atgttcccca gtacttgcca    5400
agctcaatgg ttcccttttc ccggtcttta ggattttggg caaatttatt caagatggat    5460
acatttggtt ccacaagggg gacactttgg ggttcacaag gatggggcc acagctcacc    5520 agggcagaac ttgagccccc tatgacttgg ggggttgatg gtggcagaga agtctctgct    5580
gggtgtgtgg gaggatccct ctgagcgagg gaggaatctg gtaaaagtag taaagatcca    5640
ctcatcagga cctgtgcttc ttgcctatgt tttcaggatc catgggttaa gcagcttctg    5700
tgaggttgta gtattgctgt agtatccatg caggcattgg gggacaaagg ttcctgatat    5760 accttccccct tgaggccttg caaaagaaa aacaagagag tctcaataca tgcaccaagt    5820
caaggtgttg gttacttatt aagtaatgac tgatttttttt ctgtgactca gtcgagtcag    5880
atgttgtgtc aaattcaaca cagaaagagc caggcatata gcacttgata ggcctagggt    5940
taccacagga tccaaccaca tttgattcag gatctcaaag ccagaaacct ctgtttctgt    6000
ttcttgtgat tccttctcag aaagaggaaa ccacacacag agaattacct gctcagttat    6060
tccccaaagt taatatcatt tgggaaagcg ggtgagggtt ttatccttcc ctcttgggca    6120
tcactgtcaa ttttattgcc atggttaatc aaggtgaatt tcaatagtgt ctgacctgca    6180
aattagtttt ctgccatttg gaatcaagga tgtacgggtc aacagctgca ggagacttca    6240
gagaggtccc catgcttaaa aaatttctct caggagagta gtaaggtagg gtggctattg    6300
tcatcacagg ttggaagaca agatggtcac aaatgttaga gaattattc tgatggaaac    6360 ttctcctccg gggtacttta taatggacat gaagactcaa cttcaggaag atgtaagttt    6420
tccccagtta atctacagat ccagtgcatt caaaatgcca accagatttt gctcacaagc    6480
```

```
tgattatcaa attcatatgg aagtataaag ggccaaaaat agctgaataa ttttgctgaa    6540
gggtaagggg gggacccatt attccacata tcatgattta taaactctag taatttaaac    6600
acaaatagaa caatgaaaga gagtagggggg cctagaaaat acagatgtga acatgttgga    6660
gatggctggg cactcctgtg ggtaaaggat tcgatcatta gtgctgtgac attggcttcc    6720
catgtgggaa aaacgtaaaa cttgaactct atctcaaacc attcacaaat gtatactcca    6780
gatagaataa atatgaaaag caaagtttca aaacttttt aaaaaatgtg ttttaagac     6840 agagacatga taaggcacag aatttcttgg tcaaaatata aaggacaag ccataaaagt     6900 gtgatgttac cattcgaaca tttgtttaaa gtatgcaggg caaaaaccaa tacaaagtta    6960
aaggacaagt ctcaaattag tagaagatat ttgcagtgca taaaagcaac agaagatctt    7020
tatccataac atatcagact ctcacaaagt aataagttaa agacagcaga attaaaaatg    7080
ggcaaagtac gtgaccaagc caatatccaa ataaaaagat gccaaacatt acttgaatca    7140
gtgagatgca aatgaaaaca accaatatca ttttatattc aaattagcaa aatgaacaag    7200
accaataaca tcaagcatga gggaggatat gaccaaataa ctgtgatgca gtgttgatgg    7260
ggatgtaaat tgttacaact gcagtggaga taatttggga tatctagtaa aaatatctat    7320
taaaaatgaa gatgctctgg ccccagaact tccacttcca gattcattgc tcagagaagt    7380
tttgatgtat aagagtgttc acagaagcac aaacaacaga aattggaaaa ttgtaataat    7440
aattataaac taatatctaa taggggaatg aataaaattg taatacatta ataaaatatg    7500
acacaataaa tgaactagat ccacaggcat caacacaggt aaatctcaaa aatatgttga    7560
atgaaataag caaattttaa aagtgcatgt acactctgac attatttata aaaaataaaa    7620
gcacatgcca tatattattc attattatgt cattgtttat agatacttac ataataagag    7680
aatcacaagt ataaaaaaag cctggaggca gaacccacaa atttcaagat agggtatgca    7740
gtatggagga tggaataggg gtgaagaagg ggtctcaaca caaacatttt attgcttgaa    7800
ataaaagact gaagcaaatt tggcaaaagt taaatttgct aaatctgaca gatttattta    7860
gcaaatctgc taatttgcta aataaacttg aagctagtat gttaccttca gtagttttct    7920
ttatatttgg cataattcat aattcatggg aggaggtaat tacatattaa aaatatatat    7980
tcactggctg ggtgcagtgg cttatgcctg taatcccagc actttgggag gccaagatgg    8040
gtagatcacc tgagttcagg agttcgagac cagcctggcc aacatgatga aaccctgttt    8100
ctactaaaaa tataaaaatt agccgggcgt ggtggcgggc acctgtggtc ccagctactc    8160
aggaggctga ggcaggagaa ttgcttgaac tgggagatgg aggttgctgt gagccgagac    8220
tgtaccactg cacttcagtc tgggtgacag agcgagactc catctcaaaa taaataaata    8280
aataaaaata aataaataaa gtatatattc ataattaaca gagtaactgt atgtaatgag    8340
tacctgctgt gttccaggca ctgtttaaag tacaggcata cctcatttta ttgcacttta    8400
tttttttatt gtgctgcacg gatgttgtat ttttagcaaa ttgaaagttt gtggcaaccc    8460
tgcctggagc aaatctatca atgctgtttt tcaatagcat gtgttgactt tgtgcctctg    8520
gatcaccttt taataattct tgcaataacct caaactttt cattattatt gtgtctgttc    8580
tggtgactgt aatcagttat ttttgatgtt actattttaa ttgttttagg gcaccatgaa    8640
ccatgcccat ttatgacagt gaacttgatc cataaatgtt gggtgtgttc tgactgctcc    8700
atgaccagcc attctgtatc tccttctcct taggcccccc tatgccctga ccacaaaaa     8760 tattaaaatt aggccaatta ataaccctac aatggtttct aagtgttcaa gggaaaggaa    8820
```

```
gaattgcgca tctctcactt taaatcaaaa gctagaaatg attaagttta gtgaggaagg    8880
gatgctgaaa gtggagacag gctgaaagct aggtctcttg tgtcaaataa tgagccaagt    8940
tgagaaggta gagaaaaagt tcttgaagga aattaaaagt actaatccag tgagcacatg    9000
aatgataaga aaacgaaata gccttattgc tgatatggag agagttttag tggtctgggt    9060
aaatcggaac agccacaaaa ttcccttaag caaaagccta atccagagca aagtcccaac    9120
tctcttaaat tttatgaaag ctgaagtggt gaggaagctg cagaagaaaa gtttgaagct    9180
aggagaggtt ggttgattca agtggtttaa gggaagatac catctcctta acatcaaaat    9240
gcaacgtgaa gaagcaggtg ctaatataga aactaatagg tgctgcagca cagcaggtta    9300
tccaaaagag cttcctaaga ttattgacaa aggtggctac actaaacaac agattttcaa    9360
tgtagacaaa acagccttat attggaagaa gatgctacta ggtctttcat agctagagag    9420
aagtcaatgc ctggcttcaa aggacagcct gcctctcttg ttaggggcta atgcagctgg    9480
tgactttaag ttgaagccaa tgctcattta ccattctaaa aacccctaagt cccttaagaa    9540 ttatgctaag tctactctac ttatactctg taaatggaat agcaaagcct ggatgacagc    9600
acatctgttt agagcatggt ttactgaata tttaaagccc actgttgaga ctcgctcagg    9660
aaaaaagatt cctttcaaaa tattactgct cattgaaaat gtgcctggtc acccaagaga    9720
tctgatggag atgtacaagg agattaatat tgttttcat gactggtaaa acaacattga    9780
ttttacatgg accaaggagt aattttgact ttcaattctt attaagaaat acatttcgta    9840
aggctagagc tgccacagat gatgattcct ctgatagatc tgggtgaaac cttctggaaa    9900 ggattccacca ttctagatgc aacaaagaac atttgtgatt catgggagca ggtataaata    9960
ccaacattag gaggagtttg gaagcaggtg attccaattc tcctggatga gttggaggag   10020
ttcaagactt cagtggagga agtaactgca agtatggtag aaatagcaag agaactagag   10080
atagaagtgg agtctgaaga cgtggctgaa ttgttgcaat cccgtgatca aacttaacac   10140
atgaggagtt tattctctct gatgagcaaa gaaggtggtt tcttgaaatg gaatctactc   10200
ctggtgaaga tggtgtgaac attgttgaaa tgacaacaga agatagagaa tgttacataa   10260
acttagttga gaaagaggcg tcagtatttg agaggagtga ctccaattt tgaatgctgtt   10320 ctactgtagg taaaatgcta tcaaacagca tcgcatgcta cagataaatc ttttgtgaaa   10380
ggaagagtca atcaatgtgg caagatttgt tgttgtccta ttttacgaaa ttggcacagc   10440
cacgccagcc tttggcaacc accattctga tcagtcagca gccattgaca tcaaggcaag   10500
atgccctcca tcagcaaaga aattatgact cactgaaagc tcaggtgatt ttagcatgta   10560
tttggtaata aattattttt tgattaagac gtactttttt tttcagacat aatgtctttg   10620
tacacttagt agactacctt ataggggtaaa cataaacttt atgtgcactg ggaaaccaaa   10680
aaatgaatgt aactggcttt attgtgatat ttgctttatt gtggtggtct ggaactgaac   10740
ctgagatatc tctgaggttt gcctatactg gaatttccaa ggttagtgaa acatcctttc   10800
tgcagcctga gtggtgagat ttaggctagt ctcaaaaata taaaaataa ctagaatata   10860 atgtaataac agtgatcatt aagataacaa tgctagcagc taccattgac tgagtagtat   10920
gtgccatgca ctctgcaagc actattttat taatgctcat gtgtgaggta gatattatca   10980
ttattcttgt tttatattca aggttcagag aggttaattc acttgctcag agtcacacag   11040
gtagcccaga tctgctatgt gccagcccta attactgagc catcctgtct gtcccacctt   11100
ttctgaccca actccccact tctgaaccac aggcggtgta gctggctttg aatataggtg   11160 ctcttttttat ataggtactc ttgaaaggat caacttact ttttttttt ttttcaaata   11220
```

```
atccaataac tttgactttt tattaggtta cactggcatt ctcccaagtt tttcatcaaa    11280
ctcatgaagc ctgctgctcc ttcaattctc aaggcgttgg agtgaggccg cctggggtga    11340
atcgaagctt tcggatttat caaatgtggt gtgatttcta agacgccatt gagccctgct    11400
aaaggagttg ctaatatcca cctcgttctg cggttaagaa accaacagga aaagaacgc     11460 acaactccca gcacagtgct ggcgcctgtg aggcactcag ccgacgggag ctttgttctt    11520
cgttgtattg tggcggggaa gcaacatggg gccttgtcct gcggacacac ttgagttaag    11580
atcacactgg ggctccttca ggccctgggc caagttgggg cacaggccga gttcggttgt    11640
tgctgtagcc tcagaaccac ccagagttga ctgaagacac tcgggggcct ccataactga    11700
gagcaggcag aggcattgtt tttaacccag tgtggacccc caaatggaac attttccttc    11760
cctaggtgaa cgccttcgga accctccgaa aatcgcagtt tcacttttag caaagagccc    11820
cgctgcagca ggggaaagcc cccacaaacc ccgtcctctc caagggaat gttccgagcc      11880 ccctgcttcc tccacccttc tcttcccct ggttaattcc ttcgctccag ctcgttctgc     11940
cttctttctt tctttgcctt ttcgaggccc gctcttctct gattttgaag ggctggcgca    12000
ggcttgggca cttctttcag gttctgtatt gtatgtctgc cctgtggctt ctccttttgc    12060
aactccgagc aactctgtgc ttggattgca gctcccaaca gtcctgccct gacttgcccc    12120
agtcacaggg cagagatgaa ccagggactg tacccagggt tttgagttcc tgccatattt    12180
atagcatcaa ctctccttta gctcttggga aaaagggttt taaagtgctg caatcttcta    12240
acacaaaatt atatcagtgc tgaaaatgtg ttttccactt ataccccagc aggaaaaaaa    12300
aaaaagatga tatctgtttc aggtaagagt catgatgacc tcagaaagca atatcagaag    12360
ctatcaaaat gtttatacct gtatattcag tagtccattc tggaacattt ctccagtgga    12420
tgtaatctta gtcttggcac aatagagtat gaacagagat gttaaatgtt aaaagcaatg    12480
gaaatgttca gaaataaagc aatatttaag taaacaatga taatgcattc aatataattt    12540
taggcattaa catgatgatg ttttagaatt atgaaaccta tggaaaggtt gacaaggaaa    12600
acgcagacag catgcttgat ataaacatac attcagcatg attataacta tgtaaaatgt    12660
aaaaaatgtt tttaaaacat tagaagaaaa tacaccaaga tgcgtttccc ttgctgttgt    12720
ttctagtggc taattttgc aatgtgtatt actgcagtta tatcacctt acaaatggaa      12780 agcttaaaaa taactcactt cccttcccag agagcaatgt tcagtgcaaa gccacactcc    12840
actccaggga tggccttcag cactggactt tttgggagcc agaatcaagc agtatgtgtc    12900
acttcttatc tcatgttgtt ggtgccactt actcatatgt tgtctcatca ttctgcagtt    12960
gtttaatgtg tttatatctt tctctacaac catttttttaa aagctatttt taaaattgtg    13020
gcaaaatgta tgcataacat aaatttacca ttttagtcat ttctaagtat acactccact    13080
ggcattaagt atatttatat ttttgtgcaa tcattaccac catgcatcca cagaactttt    13140
tcatcttcct aaactaaaac tctgtaccca ctaagcacca actccccatt cccctcccc     13200 cagttccagg taaccgctat gatattttca gtttctctga cgaattcaga gacaccactc    13260
ttggtacctc ctgcaagtag aatcatactg tatttaccttt tttgcacaat catttttttaa   13320 aacttaaaaa aaatttttaa ttaattttttt tgagacagtc tcactctgtc acccaggctg   13380
gttggtgttt gcagtggcac gatcatggct cactgtagcc ttcacctcgt gggctcaagt    13440
gatcttcaca tctcagactc ccgagtattt gggactacag gcaccacca cggtgcccgg     13500 ctaattttttt aattttttgt ggagatgagg tcttactatg ttgcccaggc tggtctcaaa   13560
```

```
ctcctaggcc caagggatcc tcctacttca gcctttcaaa gtgctgagat tacaaagcga   13620
gccacaagcc tcggcctgca caatcattat aaaaagctct ctgaggataa ggaccaaggc   13680
cctgatttgt tttcattgta aacataatgt tcatttgctc attgatttga tattgactgt   13740
gcacccacac gtgtgctggg cactgttcga ggcagggttt aagaaacgct caagaagcac   13800
atgtggtctc tcaaggggac ggtgtagtgg acagagataa caaagaaaaa cacagagaag   13860
aaagaatgac ggagagtgag aagtgctgta agtgcagtga cagacaccgc cccagggcct   13920
cctggacagg ctgcatgttt gtaggatgat ggggagtggt cctggagaag actgaggagg   13980
agccctgggg ggtccaggca gagagaggag gggcacagag ctggaggacg gaagggcctt   14040
tgtacagcat gtgtgtgtgt gtgtgtatgc tgggggacac gcagggagat ggcaggcctc   14100
agcactgggg agagctggag tgcattctag atgcagcagg gagctggagc agggaccctc   14160
ttctccctgc ctggcctgag agcagggaag gaggccctgg gctgtggctg attgcagtca   14220
acactgagga acaagtgcca atgcttcatg cagggcacaa cctctgccac acttttacct   14280
atgtgacctt ctgggccagg tactgtgagg tgcttcattt ctcagatagc aaggctgagg   14340
ctcagatcaa tgctgctttg cacacagctg gaagtggcca aatcagcccg aaaccccccat  14400 tttgttctgc atctttgtgc agggctgggt ggctgtgtgt gcaatgtctg ttgtgctgga   14460
catgcaacag gaaagcaatt gttacctcta attttagga ggccaaaggg caagaagcca    14520
cgtgctccag gccaaagagc agctaaggga atgaagagta aatctgtgat tgaatgaatg   14580
agcagatgaa aagagaaaaa gcctcccccct gcacaaacct gcaacccatt cccttcctgg   14640
ggtcctgtgg ggagggggct tttcatcagt gccctgggtc aggaagagaa gagggaggcc   14700
ttgtggtgga gggaagggga ggagagctca ccatcagagg tggaaagaag gttctagtcc   14760
ctccagagca cactcaggga tgctttcttg tgcttctgtc ccaaggcctt gtctcgacct   14820
tgcttactat aaacacagtg ctacatcctg cttttccttt acttcattgc ataaaccttc   14880
cctgaatcgc ttccagaatc tttagaacca ccgttttaa ggtttgaata cttgtatacc    14940
aagtaaatga ccacagctta ttgaaactcc tctttatagt caaccactta ggttgttcta   15000
ttgttatttc tagaacacat aactaatgcc aataaataat gatgatgcca cagattagta   15060
tttcctgagg atggatctct tgcgtgggtt ccaaagctct aagcaattta tatgggccct   15120
ggagtttcct ccacagctcc taaggcagct ctggcacatg aggaggctgg gaaaagagca   15180
ggggtgatgg gtgcatctgc cttggtaagt gaacttgttg gttctgtccc acgcagcttg   15240
ggtgtcggtg tggggggtgt gctgctgggg ttggagaggg gccgccctac ataacgtccc   15300
cacataaaag gggcaggtgt gcaggtggtc ccagggatgg cggcagctct gtctgactcc   15360
cccctactgg ggggctatgg gggctgtggg agtggagggt gaggatcacc gtcctccagg   15420
atcccccaac ccctccttgg ccattccctt tgacttcctt gggaaagagt ccaggcttca   15480
gaggattctt tgctcatttc aatctgaccc catttgaatc cccaagggtc gcagtaaacc   15540
ccaggcacac aaagacagag gcttgtggct ggcttgcggt tgctgtgatc acgatggaat   15600
cagacaacgg ctgccctggc aggcagcacc caggcacctc tcaggtggga aaagactgag   15660
ccaggtgaat gtcccagagc tccagccagc tcaggtcctt atgggtgata actgcactag   15720
acacctctcc gaagaagcca acagaaactg catgcagcgg caacatgagc aaagataagt   15780
gttgggaccc gttcttcgct gccacctcca agtctgaaca gcaggctcta agggggcat    15840 gggagccccct cagaaagggc cactgcccat gcctcacctc ctgcccgcca ctccactctt   15900
tattgtccta cctgactgta acaggctgca tgctcaacat ggtgtcagct gccccaaaga   15960
```

```
gcaccaggag agacagggg tgccattcgg acatgaacag gagctcctac ctgaatgtgc    16020
agacctccgc cactggagct                                              16040

<210> SEQ ID NO 5
<211> LENGTH: 464
<212> TYPE: DNA
<213> ORGANISM: Homo sapiens

<400> SEQUENCE: 5
cctgctgctc cttcaattct caaggcgttg gagtgaggcc gcctggggtg aatcgaagct    60
ttcggattta tcaaatgtgg tgtgatttct aagacgccat tgagccctgc taaaggagtt   120
gctaatatcc acctcgttct gcggttaaga aaccaacagg aaaaagaacg cacaactccc   180
agcacagtgc tggcgcctgt gaggcactca gccgacggga gctttgttct tcgttgtatt   240
gtggcgggga agcaacatgg ggccttgtcc tgcggacaca cttgagttaa gatcacactg   300
gggctccttc aggccctggg ccaagttggg gcacaggccg agttcggttg ttgctgtagc   360
ctcagaacca cccagagttg actgaagaca ctcggggcc tccataactg agagcaggca    420
gaggcattgt ttttaaccca gtgtggaccc ccaaatggaa catt                    464

<210> SEQ ID NO 6
<211> LENGTH: 475
<212> TYPE: DNA
<213> ORGANISM: Homo sapiens

<400> SEQUENCE: 6
ccacccagag ttgactgaag acactcgggg gcctccataa ctgagagcag gcagaggcat    60
tgtttttaac ccagtgtgga cccccaaatg gaacattttc cttccctagg tgaacgcctt   120
cggaaccctc cgaaaatcgc agtttcactt ttagcaaaga gccccgctgc agcagggggaa   180 agccccaca aaccccgtcc tctccaaagg gaatgttccg agcccctgc ttcctccacc    240 cttctcttcc ccctggttaa ttccttcgct ccagctcgtt ctgccttctt tctttctttg   300
ccttttcgag gcccgctctt ctctgatttt gaagggctgg cgcaggcttg ggcacttctt   360
tcaggttctg tattgtatgt ctgccctgtg gcttctcctt ttgcaactcc gagcaactct   420
gtgcttggat tgcagctccc aacagtcctg ccctgacttg ccccagtcac agggc        475

<210> SEQ ID NO 7
<211> LENGTH: 318
<212> TYPE: DNA
<213> ORGANISM: Homo sapiens

<400> SEQUENCE: 7
gggacagact gaagaggatt tcttagtatg gtttgtacct tcccagtaga gcaggaaaaa    60
gaggaacgag ctgctcccctc cacacctcag acgctgaggt caactgccct ttgggcgggg   120
cacgttggct cacgcatcta atcccagcac tttgggaggc cgtgagggga gcatcacttg   180
agcccaggag ttggagaccg gcctgggcca catagtgagg cccatcctc cggcttgcac    240 cactcaaatt ccctcgtaaa gtcacacggg gagcttgccc ccagcaaggt cgtcagtttg   300
caaaacatgg gagtgaaa                                               318

<210> SEQ ID NO 8
<211> LENGTH: 23
<212> TYPE: DNA
<213> ORGANISM: Homo sapiens
```

<400> SEQUENCE: 8
cctactactc cttcaattct caa                                        23

<210> SEQ ID NO 9
<211> LENGTH: 22
<212> TYPE: DNA
<213> ORGANISM: Homo sapiens

<400> SEQUENCE: 9
aatgttttat ttgggggttt at                                         22

<210> SEQ ID NO 10
<211> LENGTH: 22
<212> TYPE: DNA
<213> ORGANISM: Homo sapiens

<400> SEQUENCE: 10
ccacccaaaa ttaactaaaa ac                                         22

<210> SEQ ID NO 11
<211> LENGTH: 20
<212> TYPE: DNA
<213> ORGANISM: Homo sapiens

<400> SEQUENCE: 11
gttttgtgat tggggtaagt                                            20

<210> SEQ ID NO 12
<211> LENGTH: 22
<212> TYPE: DNA
<213> ORGANISM: Homo sapiens

<400> SEQUENCE: 12
gggatagatt gaagaggatt tt                                         22

<210> SEQ ID NO 13
<211> LENGTH: 23
<212> TYPE: DNA
<213> ORGANISM: Homo sapiens

<400> SEQUENCE: 13
tttcactccc atattttaca aac                                        23

<210> SEQ ID NO 14
<211> LENGTH: 27
<212> TYPE: DNA
<213> ORGANISM: Homo sapiens

<400> SEQUENCE: 14
ggttaagaaa ttaataggaa aaagaat                                    27

<210> SEQ ID NO 15
<211> LENGTH: 21
<212> TYPE: DNA
<213> ORGANISM: Homo sapiens

<400> SEQUENCE: 15
cttccccacc acaatacaac a                                          21

<210> SEQ ID NO 16
<211> LENGTH: 27
<212> TYPE: DNA
<213> ORGANISM: Homo sapiens

```
<400> SEQUENCE: 16
ggttaagaaa ttaataggaa aaagaac                                           27

<210> SEQ ID NO 17
<211> LENGTH: 18
<212> TYPE: DNA
<213> ORGANISM: Homo sapiens

<400> SEQUENCE: 17
ccccatatta cttccccg                                                     18

<210> SEQ ID NO 18
<211> LENGTH: 33
<212> TYPE: DNA
<213> ORGANISM: Homo sapiens

<400> SEQUENCE: 18
tgtttgtgag gtatttagtt gatgggagtt ttg                                    33

<210> SEQ ID NO 19
<211> LENGTH: 28
<212> TYPE: DNA
<213> ORGANISM: Homo sapiens

<400> SEQUENCE: 19
cgtttgtgag gtatttagtc gacgggag                                          28

<210> SEQ ID NO 20
<211> LENGTH: 27
<212> TYPE: DNA
<213> ORGANISM: Homo sapiens

<400> SEQUENCE: 20
ggttaagaaa ccaacaggaa aaagaac                                           27

<210> SEQ ID NO 21
<211> LENGTH: 21
<212> TYPE: DNA
<213> ORGANISM: Homo sapiens

<400> SEQUENCE: 21
cgttgtattg tggcggggaa g                                                 21

<210> SEQ ID NO 22
<211> LENGTH: 27
<212> TYPE: DNA
<213> ORGANISM: Homo sapiens

<400> SEQUENCE: 22
ggttaagaaa ccaacaggaa aaagaac                                           27

<210> SEQ ID NO 23
<211> LENGTH: 18
<212> TYPE: DNA
<213> ORGANISM: Homo sapiens

<400> SEQUENCE: 23
cggggaagca acatgggg                                                     18

<210> SEQ ID NO 24
<211> LENGTH: 33
<212> TYPE: DNA
<213> ORGANISM: Homo sapiens
```

```
<400> SEQUENCE: 24
cgcctgtgag gcactcagcc gacgggagct ttg                          33

<210> SEQ ID NO 25
<211> LENGTH: 28
<212> TYPE: DNA
<213> ORGANISM: Homo sapiens

<400> SEQUENCE: 25
cgcctgtgag gcactcagcc gacgggag                                28
```